US010766863B2

(12) United States Patent
Sandanayaka et al.

(10) Patent No.: US 10,766,863 B2
(45) Date of Patent: Sep. 8, 2020

(54) MONOCARBOXYLATE TRANSPORT MODULATORS AND USES THEREOF

(71) Applicant: NIROGYONE THERAPEUTICS, INC., Northboro, MA (US)

(72) Inventors: Vincent Sandanayaka, Northboro, MA (US); Qiong Wu, Shrewsbury, MA (US)

(73) Assignee: NIROGYONE THERAPEUTICS, INC., Natrick, MA (US)

(*) Notice: Subject to any disclaimer, the term of this patent is extended or adjusted under 35 U.S.C. 154(b) by 0 days.

(21) Appl. No.: 15/527,137

(22) PCT Filed: Nov. 17, 2015

(86) PCT No.: PCT/US2015/061101
§ 371 (c)(1),
(2) Date: May 16, 2017

(87) PCT Pub. No.: WO2016/081464
PCT Pub. Date: May 26, 2016

(65) Prior Publication Data
US 2018/0290978 A1    Oct. 11, 2018

Related U.S. Application Data

(60) Provisional application No. 62/080,703, filed on Nov. 17, 2014.

(51) Int. Cl.
| | | |
|---|---|---|
| A61K 31/4709 | (2006.01) | |
| A61K 31/47 | (2006.01) | |
| C07D 215/56 | (2006.01) | |
| C07D 401/12 | (2006.01) | |
| C07D 405/12 | (2006.01) | |
| C07D 413/12 | (2006.01) | |
| C07D 417/12 | (2006.01) | |
| C07D 471/04 | (2006.01) | |
| C07D 409/12 | (2006.01) | |
| C07D 401/14 | (2006.01) | |
| C07D 401/06 | (2006.01) | |

(52) U.S. Cl.
CPC ......... *C07D 215/56* (2013.01); *C07D 401/06* (2013.01); *C07D 401/12* (2013.01); *C07D 401/14* (2013.01); *C07D 405/12* (2013.01); *C07D 409/12* (2013.01); *C07D 413/12* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | | | | |
|---|---|---|---|---|---|
| 3,472,859 | A | * | 10/1969 | Lesher | C07D 215/56 546/153 |
| 7,402,674 | B2 | * | 7/2008 | Defossa | C07D 215/56 546/123 |
| 2006/0148806 | A1 | | 7/2006 | Watanuki et al. | |
| 2010/0267768 | A1 | | 10/2010 | DeMattei et al. | |
| 2012/0093917 | A1 | * | 4/2012 | Hromas | A61K 31/38 424/450 |

FOREIGN PATENT DOCUMENTS

| | | | |
|---|---|---|---|
| CN | 1692101 A | 11/2005 | |
| CN | 1826321 A | 8/2006 | |
| CN | 1914206 A | 2/2007 | |
| EP | 1564210 A1 | 8/2005 | |
| EP | 1650192 A1 | 4/2006 | |
| GB | 1070333 | * 4/1964 | ............ C07D 33/62 |
| JP | S61122273 | 6/1986 | |
| WO | 0136408 A1 | 5/2001 | |

OTHER PUBLICATIONS

Database Registry Chemical Abstracts Service, Columbus, Ohio, Accession No. RN 641992-79-2, Entered STN: Jan. 27, 2004.*
Khalil, O. M. New 7-substituted fluoroquinolones. Department of Organic Chemistry. 2002, 40(3), 89-96.*
Hu, Liming. Design, Practical Synthesis, and Biological Evaluation of Novel 6-(Pyrazolylmethyl)-4-quinoline-3-carboxylic Acid Derivatives as HIV-1 Integrase Inhibitors. Molecules. 2012, 17, 10652-10666.*
Database Registry Chemical Abstracts Service, Columbus, Ohio, Accession No. RN 1026940-33-9, Entered STN: Jun. 10, 2008.*
Georg Hiltensperger et al: Synthesis and Structure-Activity Relationships of New Quinolone-Type Molecules against Trypanosoma brucei, Journal of Medicinal Chemistry, vol. 55, No. 6, Mar. 12, 2012 (Mar. 12, 2012), pp. 2538-2548.
Liming Hu et al: "Design, Practical Synthesis, and Biological Evaluation of Novel 6-(Pyrazolylmethyl)-4-quinoline-3-carboxylic Acid Derivatives as HIV-1 Integrase Inhibitors", Molecules Online, vol. 17, No. 9, Sep. 6, 2012 (Sep. 6, 2012), pp. 10652-10666.
Motohide Sato et al: "Quinolone Carboxylic Acids as a Novel Monoketo Acid Class of Human Immunodeficiency Virus Type 1 Integrase Inhibitors", Journal of Medicinal Chemistry, vol. 52, No. 15, Aug. 13, 2009 (Aug. 13, 2009), pp. 4869-4882.

(Continued)

*Primary Examiner* — Samantha L Shterengarts
(74) *Attorney, Agent, or Firm* — Mintz Levin Cohn Ferris Glovsky and Popeo PC

(57) ABSTRACT

The invention generally relates to the field of monocarboxylate transport modulators, e.g., monocarboxylate transport inhibitors, and more particularly to new substituted-quinolone compounds, the synthesis and use of these compounds and their pharmaceutical compositions, e.g., in treating, modulating, forestalling and/or reducing physiological conditions associated with monocarboxylate transport activity such as in treating cancer and other neoplastic disorders, inflammatory diseases, disorders of abnormal tissue growth and fibrosis including cardiomyopathy, obesity, diabetes, cardiovascular diseases, tissue and organ transplant rejection, and malaria.

12 Claims, No Drawings

(56) References Cited

OTHER PUBLICATIONS

Hui Wang et al: "Synthesis and Structure-Activity Relationships of Pteridine Dione and Trione Monocarboxylate Transporter 1 Inhibitors", Journal of Medicinal Chemistry, vol. 57, No. 17, Sep. 11, 2014 (Sep. 11, 2014), pp. 7317-7324.

Thakur Anuradha et al: "Coumarins as anticancer agents: A review on synthetic strategies, mechanism of action and SAR studies", European Journal of Medicinal Chemistry, Editions Scientifique Elsevier, Paris, FR, vol. 101, Jul. 10, 2015 (Jul. 10, 2015), pp. 476-495.

Extended European Search Report issued in European Application No. 15861509.6, dated May 23, 2018.

Pubchem—CID 82244440, create date Oct. 20, 2014.

Pubchem—CID 11550914, create date Oct. 26, 2006.

International Search Report and Written Opinion issued in PCT/US2015/061101, dated Mar. 17, 2016.

Xuebau, Acta Pharmaceutica, vol. 25(9), pp. 670-676 1990.

Frank, et al., A Simple Inexpensive Apparatus for Performance of Preparative Scale Solution Phase Multiple Parallel Synthesis of Drug Analogs. I. Preparation of a Retrospective Library fo Quinolone Antiinfective Agents, Combinational Chemistry and High Throughput Screening, vol. 1(2), pp. 73-87 1998.

Klopman, et al., Anti-Mycobacterium avium Activity of Quinolones: In Vitro Activities, Antimicrobial Agents and Chemotherapy, vol. 37(9), pp. 1799-1806 1993.

Zhang, et al., Synthesis and antibacterial evaluation of 1-(4-thiazolylmethyl)- and 7-(4-thiazolylmethyl)amino-substituted quinolones, Eurupean Journal of Medicinal Chemistry, vol. 26(3), pp. 331-334 1991.

Notification of the First Examination Report in Chinese Application No. 201580073081.0 dated Sep. 27, 2019 with translation. Sep. 27, 2019.

Ziegler et al. "Synthesis and Antibacterial Activity of Some 7-Substituted 1-Ethyl-6-fluoro-1,4-dihydro-4-oxoquinoline-3-carboxylic Acids: Ethers, Secondary Amines and Sulfides as C-7 Substituents" J. Heterocyclic Chem., vol. 26, pp. 1141-1145. Jan. 24, 1989.

SAS Registration No. 836619-99-9 recorded into the database on Apr. 28, 2005.

SAS Registration No. 849443-51-2 recorded into the database on Apr. 28, 2005.

SAS Registration No. 849443-52-3 recorded into the database on Apr. 28, 2005.

\* cited by examiner

MONOCARBOXYLATE TRANSPORT MODULATORS AND USES THEREOF

CROSS REFERENCE TO RELATED APPLICATIONS

This application is a national phase filing under 35 U.S.C. § 371 of International Application No. PCT/US2015/061101, filed Nov. 17, 2015, and published on May 26, 2016, as WO/2016/081464A1. PCT/US2015/061101 claimed priority from U.S. provisional application 62/080,703, filed Nov. 17, 2014. The entire contents of each of the prior applications are incorporated herein by reference.

FIELD OF THE INVENTION

The present invention relates to compounds useful as monocarboxylate transport modulators. The invention also provides pharmaceutically acceptable compositions comprising compounds of the present invention and methods of using said compositions in the treatment of various disorders.

BACKGROUND

It has been well demonstrated that tumors display altered cellular metabolism, in which cancer cells exhibit high rate of glucose consumption. Tumors contain well oxygenated (aerobic), and poorly oxygenated (hypoxic) regions. Compared to normal cells, cancer cells are heavily dependent upon either aerobic glycolysis (Warburg effect, 1956) or anerobic glycolysis (in hypoxic regions) for energy (ATP) production. This glycolytic switch by highly proliferating and hypoxic cancer cells provides the energy and biosynthetic needs for cancer cell survival. To maintain this metabolic phenotype, cancer cells up regulate a series of proteins, including glycolytic enzymes and pH regulators; monocarboxylate transporters (MCTs) that will facilitate the efflux of lactate co-transported with a proton. This fundamental difference between normal cells and cancer cells has been applied for cancer diagnosis, but has not been applied for cancer therapy.

MCTs mediate influx and efflux of monocarboxylates such as lactate, pyruvate, ketone bodies (acetoacetate and beta-hydroxybutyrate) across cell membranes. These monocarboxylates play essential roles in carbohydrate, amino acid, and fat metabolism in mammalion cells, and must be rapidly transported across plasma membrane of cells. MCTs catalyse the transport of these solutes via a facilitative diffusion mechanism that requires co-transport of protons. Monocarboxylates such as lactate, pyruvate, and ketone bodies play a central role in cellular metabolism and metabolic communications among tissues. Lactate is the end product of aerobic glycolysis. Lactate has recently emerged as a critical regulator of cancer development, invasion, and metastasis. Tumor lactate levels correlate well with metastasis, tumor recurrence, and poor prognosis (MCT Lactate Meta_JClinInvest_2013).

MCTs are 12-span transmembrane proteins with N- and C-terminus in cytosolic domain, and are members of solute carrier SLC16A gene family. MCT family contains 14 members, and so far MCT1, MCT2, MCT3, and MCT4 are well characterized [Biochemical Journal (1999), 343:281-299].

Regulation and function of MCT1 and MCT4 are dependent upon interaction of other protein such as the chaperone CD147 (basigin, EMMPRIN), a member of immunoglobulin super family with a single transmembrane helix. Many studies have shown the tight association of CD147 and MCT1 and MCT4 [Future Oncology (2010), (1), 127]. CD147 acts as a chaperone to bring MCT1 and MCT4 to the plasma membrane and remain closely associated for the essential function of MCTs.

Malignant tumors contain aerobic and hypoxic regions, and the hypoxia increases the risk of cancer invasion and metastasis. Tumor hypoxia leads to treatment failure, relapse, and patient mortality as these hypoxic cells are generally resistant to standard chemo- and radiation therapy. In regions of hypoxia, cancer cells metabolize glucose into lactate whereas nearby aerobic cancer cells take up this lactate via the MCT1 for oxidative phosphorylation (OX-PHOS). Under hypoxic conditions, cancer cells up regulate glucose transporters and consume large quantities of glucose. Cancer cells also up regulate glycolytic enzymes and convert glucose into lactate, which is then efflux out of cell via MCT4. The nearby aerobic cancer cells take up this lactate via MCT1 for energy generation through OXPHOS. Thus, the limited glucose availability to the tumor is used most efficiently via synergistic metabolic symbiosis. This utilization of lactate as an energy substitute for survival prevents the aerobic cells from consuming large quantities of glucose.

SUMMARY OF THE INVENTION

In one aspect, the invention relates to compounds that are effective as monocarboxylate transport modulators. Such compounds have of formula I:

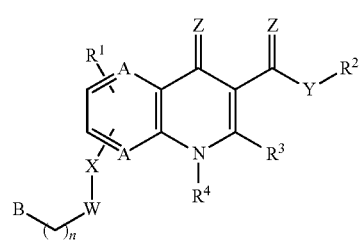

or a pharmaceutically acceptable salt thereof, wherein:
n is , 0, 1, or 2;
W is a bond, C=O, or $SO_2$;
Z is selected from O, S, N—CN, and $NR^-$;
$R^1$ is selected from the group consisting of hydrogen, halogen, —$CHF_2$, —$CF_3$, —$NO_2$, —CN, —C(O)R", —C(O)OR", —$SO_2$R", —C(O)NR"$_2$, —C(O)N(OR")R" and

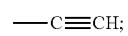

R" is hydrogen or an optionally substituted group selected from:
(a) $C_{1-6}$ alkyl or $C_{1-6}$ cycloalkyl;
(b) a 3-8 membered saturated or partially unsaturated cycloalkyl ring formed from two R";
(c) a 3-8 membered saturated or partially unsaturated heterocycloalkyl ring formed from two R" having 1-2 heteroatoms independently selected from nitrogen, oxygen, and sulfur;

(d) phenyl; and
(e) a 5-6 membered heteroaryl ring having 1-4 heteroatoms independently selected from nitrogen, oxygen, and sulfur;

X is chosen from O, S, S(O), $SO_2$, —$C_2$, and NR″;
Y is chosen from O, S, and $NR^2$;
$R^2$ is selected from the group consisting of
(a) hydrogen, —OH, —C(O)R″, —O(CH$_2$)$_{0-4}$R″, —(CH$_2$)$_{0-4}$C(O)R″, —(CH$_2$)$_{0-4}$C(O)OR″, —NR″$_2$, —(CH$_2$)$_{0-4}$C(O)NR″$_2$, —(CH$_2$)$_{0-4}$S(O)R″, —(CH$_2$)$_{0-4}$S(O)$_2$R″, or —N(OR″)R″; and
(b) an optionally substituted group selected from
(1) $C_{1-6}$ alkyl;
(2) 3-8 membered saturated or partially unsaturated cycloalkyl ring;
(3) 3-8 membered saturated or partially unsaturated heterocycloalkyl ring having 1-2 heteroatoms independently selected from nitrogen, oxygen, and sulfur;
(4) phenyl, and
(5) a 5-6 membered heteroaryl ring having 1-4 heteroatoms independently selected from nitrogen, oxygen, or sulfur;

A is nitrogen or a carbon atom optionally substituted by H or an R′ substituent;
B is a ring selected from
(a) a 3-8 membered saturated or partially unsaturated monocyclic carbocyclic ring;
(b) phenyl;
(c) an 8-10 membered bicyclic aryl ring;
(d) a 3-8 membered saturated or partially unsaturated monocyclic or bicyclic heterocyclic ring having 1-2 heteroatoms independently selected from nitrogen, oxygen, and sulfur;
(e) a 5-6 membered monocyclic heteroaryl ring having 1-4 heteroatoms independently selected from nitrogen, oxygen, and sulfur; and
(f) an 8-10 membered bicyclic heteroaryl ring having 1-4 heteroatoms independently selected from nitrogen, oxygen, and sulfur;
wherein B is optionally substituted with one or more R′ substituents;
R′ is chosen from
(a) hydrogen, halogen, —CHF$_2$, —CF$_3$, —NO$_2$, —CN, —OH, —C(O)R″, —C(O)OR″, —SO$_2$R″, —C(O)NR″$_2$, —C(O)N(OR″)R″ and

—C≡CH, and
(b) an optionally substituted group selected from
(1) $C_{1-6}$ alkyl;
(2) a 3-8 membered saturated or partially unsaturated cycloalkyl ring;
(3) a 3-8 membered saturated or partially unsaturated heterocycloalkyl ring having 1-2 heteroatoms independently selected from nitrogen, oxygen, and sulfur;
(4) phenyl; and
(5) a 5-6 membered heteroaryl ring having 1-4 heteroatoms independently selected from nitrogen, oxygen, or sulfur;

$R^3$ is chosen from
(a) hydrogen, halogen, —O(CH$_2$)$_{0-4}$R″, —(CH$_2$)$_{0-4}$C(O)R″, and (b) an optionally substituted group selected from
(1) $C_{1-6}$ alkyl,
(2) a 3-8 membered saturated or partially unsaturated cycloalkyl ring,
(3) a 3-8 membered saturated or partially unsaturated heterocycloalkyl ring having 1-2 heteroatoms independently selected from nitrogen, oxygen, and sulfur,
(4) phenyl, and
(5) a 5-6 membered heteroaryl ring having 1-4 heteroatoms independently selected from nitrogen, oxygen, and sulfur;

$R^4$ is selected from the group consisting of
(a) hydrogen, —C(O)R″, —O(CH$_2$)$_{0-4}$R″, —(CH$_2$)$_{0-4}$C(O)R″, —(CH$_2$)$_{0-4}$C(O)OR″, —NR″$_2$, —(CH$_2$)$_{0-4}$C(O)NR″$_2$, —(CH$_2$)$_{0-4}$S(O)R″, —(CH$_2$)$_{0-4}$S(O)$_2$R″, —N(OR″)R″; and
(b) an optionally substituted group selected from
(1) $C_{1-6}$ alkyl,
(2) a 3-8 membered saturated or partially unsaturated cycloalkyl ring,
(3) a 3-8 membered saturated or partially unsaturated heterocycloalkyl ring having 1-2 heteroatoms independently selected from nitrogen, oxygen, and sulfur,
(4) phenyl, and
(5) a 5-6 membered heteroaryl ring having 1-4 heteroatoms independently selected from nitrogen, oxygen, and sulfur.

In another aspect the invention relates to methods for inhibiting monocarboxylate transport. The methods comprise contacting a monocarboxylate transporter with an effective amount of a compound described herein.

In another aspect, the invention relates to a method for treating a disorder associated with monocarboxylate transport comprising administering a compound described herein. Such disorders include cancer and other neoplastic disorders, inflammatory diseases, disorders of abnormal tissue growth, metabolic disorders, diabetes, obesity, malaria, and tissue and organ rejection.

DETAILED DESCRIPTION OF THE INVENTION

In certain embodiments, the present invention relates to a compound of formula I:

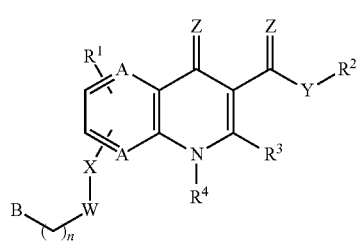

I or a pharmaceutically acceptable salt thereof, wherein:
n is 0, 1, or 2;
W is a bond, C═O, or SO$_2$;
Z is selected from O, S, N—CN, and NR″;
$R^1$ is independently selected from the group consisting of hydrogen, halogen (Br, F, I, Cl), —CHF$_2$, —CF$_3$, —NO$_2$, —CN, —C(O)R″, —C(O)OR″, —SO$_2$R″, —C(O)NR″$_2$, —C(O)N(OR″)R″ and

R" is hydrogen or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

X is either O, S, S(O), S(O)$_2$, or NR";

Y is either O, S, or NR$^2$;

R$^2$ is independently selected from the group of hydrogen, —OH, —C(O)R, —O(CH$_2$)$_{0-4}$R", —(CH$_2$)$_{0-4}$C(O)R", —(CH$_2$)$_{0-4}$C(O)OR", —NR"$_2$, —(CH$_2$)$_{0-4}$C(O)NR"$_2$, —(CH$_2$)$_{0-4}$S(O)R", —(CH$_2$)$_{0-4}$S(O)$_2$R", —N(OR")R", or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

A is a nitrogen (N) or a carbon (C) atom optionally substituted by H or R' substituent;

B is a ring selected from a 3-8 membered saturated or partially unsaturated monocyclic carbocyclic ring, phenyl, an 8-10 membered bicyclic aryl ring, a 3-8 membered saturated or partially unsaturated monocyclic or bicyclic heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur, wherein B is optionally substituted with one or more R' substituents;

R' is hydrogen, halogen (Br, F, I, Cl), —CHF$_2$, —CF$_3$, —NO$_2$, —CN, —OH, —C(O)R", —C(O)OR", —SO$_2$R", —C(O)NR"$_2$ and —C(O)N(OR")R";

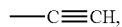

or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur.

R$^3$ is hydrogen, halogen (Br, F, I, Cl), —O(CH$_2$)$_{0-4}$R", —(CH$_2$)$_{0-4}$C(O)R", or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

R$^4$ is independently selected from the group of hydrogen, —C(O)R", —O(CH$_2$)$_{0-4}$R", —(CH$_2$)$_{0-4}$C(O)R", —(CH$_2$)$_{0-4}$C(O)OR", —NR"$_2$, —(CH$_2$)$_{0-4}$C(O)NR"$_2$, —(CH$_2$)$_{0-4}$S(O)R", —(CH$_2$)$_{0-4}$S(O)$_2$R", —N(OR")R", or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur.

Compounds described herein and pharmaceutically acceptable compositions thereof, are useful for treating a variety of diseases, disorders or conditions, associated with abnormal cellular responses triggered by altered cellular metabolism. Such diseases, disorders, or conditions include those described below.

Compounds provided by this invention are also useful for the study of monocarboxylate transport modulation in biological and pathological phenomena; the study of intracellular and intercellular signal transduction pathways mediated by lactate and other monocarboxylates, and the comparative evaluation of new monocarboxylate transport modulatorsThe novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

As used herein, the following definitions shall apply unless otherwise indicated. For purposes of this invention, the chemical elements are identified in accordance with the Periodic Table of the Elements CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

Generally, reference to a certain element such as hydrogen or H is meant (if appropriate) to include all isotopes of that element, for example, deuterium and tritium for hydrogen.

The term "alkyl" as used herein means a straight- or branched-chain hydrocarbon having from one to eight carbon atoms, and includes, for example, and without being limited thereto, methyl, ethyl, propyl, isopropyl, t-butyl and the like. Substituted alkyl includes, for example, and without being limited thereto, haloalkyl, hydroxyalkyl, cyanoalkyl, and the like. This is applied to any of the groups mentioned herein, such as substituted "alkenyl", "alkynyl", "aryl", etc.

The term "alkenyl" as used herein means a straight- or branched-chain aliphatic hydrocarbon having at least one double bond. The alkene may have from two to eight carbon atoms, and includes, for example, and without being limited thereto, ethenyl, 1-propenyl, 1-butenyl and the like. The term "alkenyl" encompass radicals having "cis" and "trans" orientations, or alternatively, "E" and "Z" orientations.

The term "alkynyl" as used herein means a straight- or branched-chain aliphatic hydrocarbon having at least one triple bond. The alkyne may have from two to eight carbon atoms, and includes, for example, and without being limited thereto, 1-propynyl (propargyl), 1-butynyl and the like.

The term "cycloalkyl" as used herein means an aliphatic carbocyclic system (which may be unsaturated) containing one or more rings wherein such rings may be attached together in a pendent manner or may be fused. In one aspect, the ring(s) may have from three to seven carbon atoms, and includes, for example, and without being limited thereto, cyclopropyl, cyclohexyl, cyclohexenyl and the like.

The term "heterocycloalkyl" as used herein means a heterocyclic system (which may be unsaturated) having at least one heteroatom selected from N, S and/or O and containing one or more rings wherein such rings may be attached together in a pendent manner or may be fused. In one aspect, the ring(s) may have a three- to seven-membered cyclic group and includes, for example, and without being limited thereto, piperidinyl, piperazinyl, pyrrolidinyl, tetrahydrofuranyl, tetrahydropyranyl and the like.

The term "heteroatom" means one or more of oxygen, sulfur, nitrogen, phosphorus, or silicon.

The term "unsaturated", as used herein, means that a moiety has one or more units of unsaturation.

The term "alkoxy" as used herein means a straight- or branched-chain oxygen-containing hydrocarbon; in one aspect, having from one to eight carbon atoms and includes, for example, and without being limited thereto, methoxy, ethoxy, propyloxy, isopropyloxy, t-butoxy and the like.

The term "halo" or "halogen" includes, for example, and without being limited thereto, fluoro, chloro, bromo, and iodo, in both radioactive and non-radioactive forms.

The term "alkylene" as used herein means a difunctional branched or unbranched saturated hydrocarbon; in one aspect, having one to eight carbon atoms, and includes, for example, and without being limited thereto, methylene, ethylene, n-propylene, n-butylene and the like.

The term "aryl", alone or in combination, as used herein means a carbocyclic aromatic system containing one or more rings. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl or acenaphthyl. The "aryl" group may have 1 to 4 substituents such as lower alkyl, hydroxyl, halo, haloalkyl, nitro, cyano, alkoxy, lower alkylamino and the like.

The term "heteroaryl", alone or in combination, as used herein means an aromatic system having at least one heteroatom selected from N, S and/or O and containing one or more rings. In particular embodiments, heteroaryl is one, two or three rings. In one aspect, the heteroaryl has five to twelve ring atoms. The term "heteroaryl" encompasses heteroaromatic groups such as triazolyl, imidazolyl, pyrrolyl, tetrazolyl, pyridyl, indolyl, furyl, benzofuryl, thienyl, benzothienyl, quinolyl, oxazolyl, thiazolyl and the like. The "heteroaryl" group may have 1 to 4 substituents such as lower alkyl, hydroxyl, halo, haloalkyl, nitro, cyano, alkoxy, lower alkylamino and the like.

It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon or on different carbons, as long as a stable structure results.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$;)$-(CH_2)_{0-4}CH(OR^\circ)_2$, $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ C(O)R^\circ;)-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-40}C(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)^\circ_2$; $-OP(O)(OR^\circ_2$; $SiR^\circ_3$; $-(C_{1-4}$ straight or branched)alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6- membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12- membered saturated, partially unsaturated, or aryl mono—or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, —$(CH_2)_{0-2}R^•$, -(halo$R^•$), —$(CH_2)_{0-2}OH$, —$(CH_2)_{0-2}OR^•$, —$(CH_2)_{0-2}CH(OR^{108})_2$; —O(halo$R^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$C(O)SR^•$, —$(C_{1-4}$ straight or branched alkylene)$C(O)OR^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include =O and =S.

Suitable divalent substituents on a saturated carbon atom of an "optionally substituted" group include the following: =O, =S, =$NNR^*_2$, =NNHC(O)$R^*$, =NNHC(O)O$R^*$, =NNHS(O)$_2R^*$, =$NR^*$, =NO$R^*$, —O(C($R^*_2$))$_{2-3}$O—, or —S(C($R^*_2$))$_{2-3}$S—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(C$R^*_2$)$_{2-3}$O—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^•$, -(halo$R^•$), —OH, —$OR^•$, —O(halo$R^•$), —CN, —C(O)OH, —C(O)O$R^•$, —$NH_2$, —NH$R^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —C(O)$R^†$, —C(O)O$R^†$, —C(O)C(O)$R^\backslash$, —C(O)$CH_2$C(O)$R^\backslash$, —S(O)$_2R^†$, —S(O)$_2NR^†$, —C(S)$NR^†_2$, —C(NH)$NR^†_2$, or —N($R^†$)S(O)$_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono—or bicyclic ring having 0-4 heteroatoms independently selected from nitrogen, oxygen, or sulfur.

Suitable substituents on the aliphatic group of $R^†$ are independently halogen, —$R^•$, —(halo$R^•$), —OH, —$OR^•$, —O(halo$R^•$), —CN, —C(O)OH, —C(O)O$R^•$, —$NH_2$, —NH$R^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p—toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The term "pharmaceutically acceptable salt" means either an acid addition salt or a basic addition salt which is compatible with the treatment of patients. In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed and such salts can exist in either a hydrated, solvated or substantially anhydrous form. In general, the acid addition salts of these compounds are more soluble in water and various hydrophilic organic solvents, and generally demonstrate higher melting points in comparison to their free base forms. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to inhibit or slow the appearance of symptoms of the named disorder or condition. The term "therapeutically effective amount" means an amount of the compound which is effective in treating or lessening the severity of one or more symptoms of a disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is pharmaceutically acceptable oil typically used for parenteral administration.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

According to one aspect, the present invention relates to a compound of formula II,

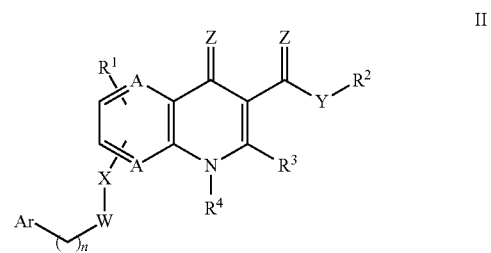

or a pharmaceutically acceptable salt thereof. In some embodiments, the compound has the following structure:

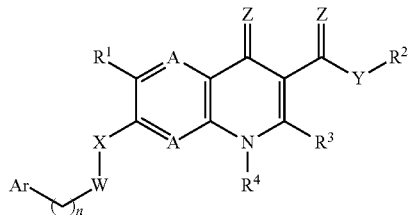

or a pharmaceutically acceptable salt thereof, wherein:
n is 0, 1, or 2;
W is a bond, C=O, or $SO_2$;
Z is selected from O, S, N—CN, and NR";
$R^1$ is independently selected from the group consisting of hydrogen, halogen (Br, F, I, Cl), —$CHF_2$, —$CF_3$, —$NO_2$, —CN, —C(O)R", —C(O)OR", —$SO_2$R", —C(O)NR"$_2$, and —C(O)N(OR")R",

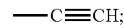

R" is hydrogen or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;
X is either O, S, S(O), $SO_2$, or NR";
Y is either O, S, or $NR^2$;
$R^2$ is independently selected from the group of hydrogen, —OH, —C(O)R", —O($CH_2$)$_{0-4}$R", —($CH_2$)$_{0-4}$C(O)R", —($CH_2$)$_{0-4}$C(O)OR", —NR"$_2$, —($CH_2$)$_{0-4}$C(O)NR"$_2$, —($CH_2$)$_{0-4}$S(O)R", —($CH_2$)$_{0-4}$S(O)$_2$R", —N(OR")R", or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

A is a nitrogen (N) or a carbon (C) atom optionally substituted by H or R' substituent;

B is a ring selected from a 3-8 membered saturated or partially unsaturated monocyclic carbocyclic ring, phenyl, an 8-10 membered bicyclic aryl ring, a 3-8 membered saturated or partially unsaturated monocyclic or bicyclic heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur, wherein B is optionally substituted with one or more R' substituents;

R' is hydrogen, halogen (Br, F, I, Cl), —CHF$_2$, —CF$_3$, —NO$_2$, —CN, —OH, —C(O)R", —C(O)OR", —SO$_2$R", —C(O)NR"$_2$ and —C(O)N(OR")R";

—C≡CH, or an optionally substituted group selected from C$_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur.

R$^3$ is hydrogen, halogen (Br, F, I, Cl), —O(CH$_2$)$_{0-4}$R", —(CH$_2$)$_{0-4}$C(O)R", or an optionally substituted group selected from C$_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

R$^4$ is independently selected from the group of hydrogen, —C(O)R", —O(CH$_2$)$_{0-4}$R", —(CH$_2$)$_{0-4}$C(O)R", —(CH$_2$)$_{0-4}$C(O)OR", —NR"$_2$, —(CH$_2$)$_{0-4}$C(O)NR"$_2$, —(CH$_2$)$_{0-4}$S(O)R", —(CH$_2$)$_{0-4}$S(O)$_2$R", —N(OR")R", or an optionally substituted group selected from C$_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur; and Ar is aryl, heteroaryl, substituted aryl or substituted heteroaryl.

In some embodiments, the compound has the following structure III:

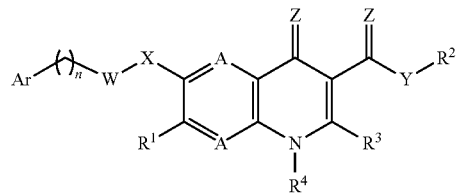

or a pharmaceutically acceptable salt thereof, wherein:

n is 0, 1, or 2;

W is a bond, C=O, or SO$_2$;

Z is selected from O, S, N—CN, and NR";

R$^1$ is independently selected from the group consisting of hydrogen, halogen (Br, F, I, Cl), —CHF$_2$, —CF$_3$, —NO$_2$, —CN, —C(O)R", —C(O)OR", —SO$_2$R", —C(O)NR"$_2$, and —C(O)N(OR")R",

—C≡CH;

R" is hydrogen or an optionally substituted group selected from C$_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

X is either O, S, S(O), SO$_2$, or NR";

Y is either O, S, or NR$^2$;

R$^2$ is independently selected from the group of hydrogen, —OH, —C(O)R, —O(CH$_2$)$_{0-4}$R", —(CH$_2$)$_{0-4}$C(O)R", —(CH$_2$)$_{0-4}$C(O)OR", —NR"$_2$, —(CH$_2$)$_{0-4}$C(O)NR"$_2$, —(CH$_2$)$_{0-4}$S(O)R", —(CH$_2$)$_{0-4}$S(O)$_2$R", —N(OR")R", or an optionally substituted group selected from C$_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

A is a nitrogen (N) or a carbon (C) atom optionally substituted by H or R' substituent;

B is a ring selected from a 3-8 membered saturated or partially unsaturated monocyclic carbocyclic ring, phenyl, an 8-10 membered bicyclic aryl ring, a 3-8 membered saturated or partially unsaturated monocyclic or bicyclic heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur, wherein B is optionally substituted with one or more R' substituents;

R' is hydrogen, halogen (Br, F, I, Cl), —CHF$_2$, —CF$_3$, —NO$_2$, —CN, —OH, —C(O)R", —C(O)OR", —SO$_2$R", —C(O)NR"$_2$ and —C(O)N(OR")R",

—C≡CH, or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur.

$R^3$ is hydrogen, halogen (Br, F, I, Cl), —O(CH$_2$)$_{0-4}$R", —(CH$_2$)$_{0-4}$C(O)R", or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur;

$R^4$ is independently selected from the group of hydrogen, —C(O)R", —O(CH$_2$)$_{0-4}$R", —(CH$_2$)$_{0-4}$C(O)R", —(CH$_2$)$_{0-4}$C(O)OR", —NR"$_2$, —(CH$_2$)$_{0-4}$C(O)NR"$_2$, —(CH$_2$)$_{0-4}$S(O)R", —(CH$_2$)$_{0-4}$S(O)$_2$R", —N(OR")R", or an optionally substituted group selected from $C_{1-6}$ alkyl, 3-8 membered saturated or partially unsaturated cycloalkyl ring, 3-8 membered saturated or partially unsaturated heterocycloalkyl ring having 1-2 heteroatoms independently selected from nitrogen, oxygen, or sulfur, phenyl, or a 5-6 membered heteroaryl ring having 1-4 heteroatoms independently selected from nitrogen, oxygen, or sulfur; and Ar is aryl, heteroaryl, substituted aryl or substituted heteroaryl.

In one embodiment of structures I, II and III, Z is oxygen. In another embodiment, A is carbon. In other embodiment, n is equal to 0. In some embodiments, $R^3$ is hydrogen, Y is oxygen, and $R^2$ is hydrogen. In a further embodiment, the base addition salt is formed from sodium, potassium, magnesium, calcium.

In some embodiments, the compound has the following structure:

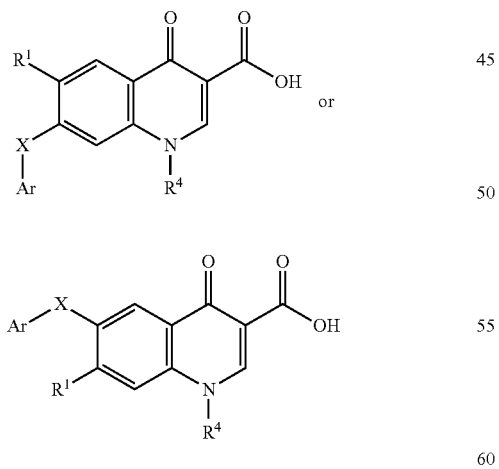

or a pharmaceutically acceptable salt thereof, wherein each of $R^1$, $R^4$, X, and Ar is as defined above and described herein. In some embodiments, $R^1$ is a —C(O)R°. In some embodiments, X is a methylene or substituted methylene.

In some embodiments, the compound has the following structure:

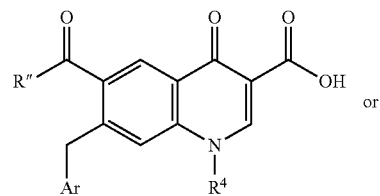

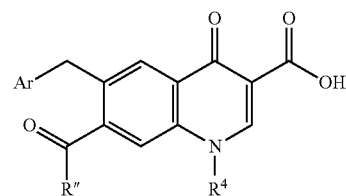

wherein each of R", Ar, and $R^4$ is as defined above and described herein.

In some embodiments, R" is an amine (e.g., azetidine). In some embodiments, Ar is substituted phenyl (e.g. trifluoromethyl phenyl) and the other is substituted pyrazole (e.g. dimethyl pyrazole). In some embodiments, $R^4$ is substituted or unsubstituted alkyl (e.g., isopropyl, isobutyl, cyclopropyl).

In some embodiments, the compound is selected from;

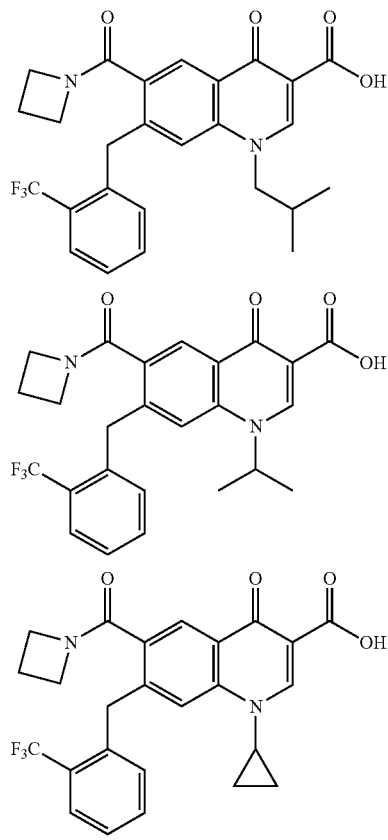

-continued

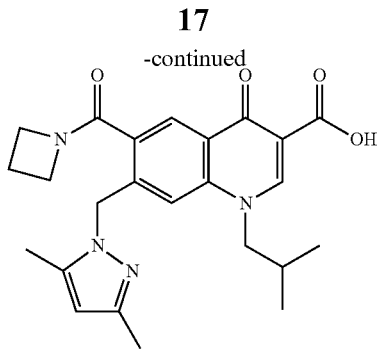

In some embodiments, the compound has the following structure:

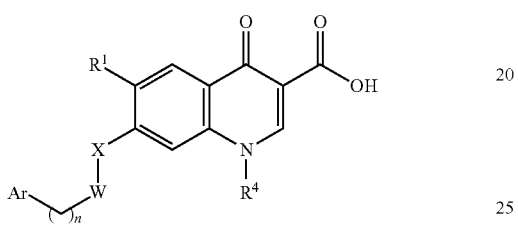

wherein each of $R^1$, $R^4$, X, n, W, and Ar is as defined above and described herein. In one embodiment, X is nitrogen. In another embodiment, n is equal to 1. In a further embodiment, W is a bond, and a base addition salt is formed from sodium, potassium, magnesium, or calcium.

In some embodiments, the compound has the following structure:

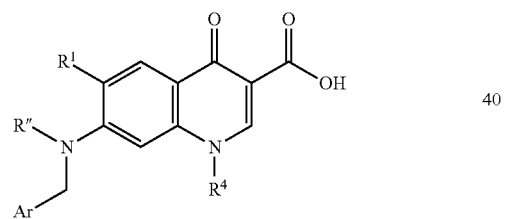

wherein each of R", $R^1$, Ar, and $R^4$ is as defined above and described herein. In some embodiments, R" is an alkyl (e.g., methyl). In some embodiments, $R^1$ is a halogen (e.g., fluoro). In some embodiments, $R^1$ is an amide (e.g., azetidino amide). In some embodiments, Ar is unsubstituted or substituted phenyl (e.g. p-chlorophenyl). In some embodiments, $R^4$ is substituted or unsubstituted alkyl (e.g., isopropyl, isobutyl, ethyl, benzyl).

In some embodiments, the compound is selected from:

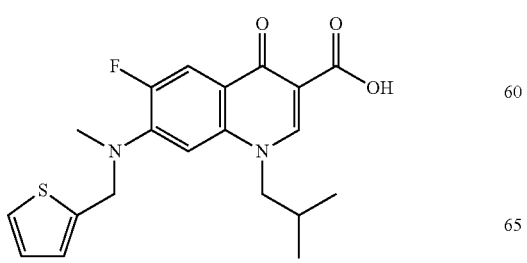

-continued

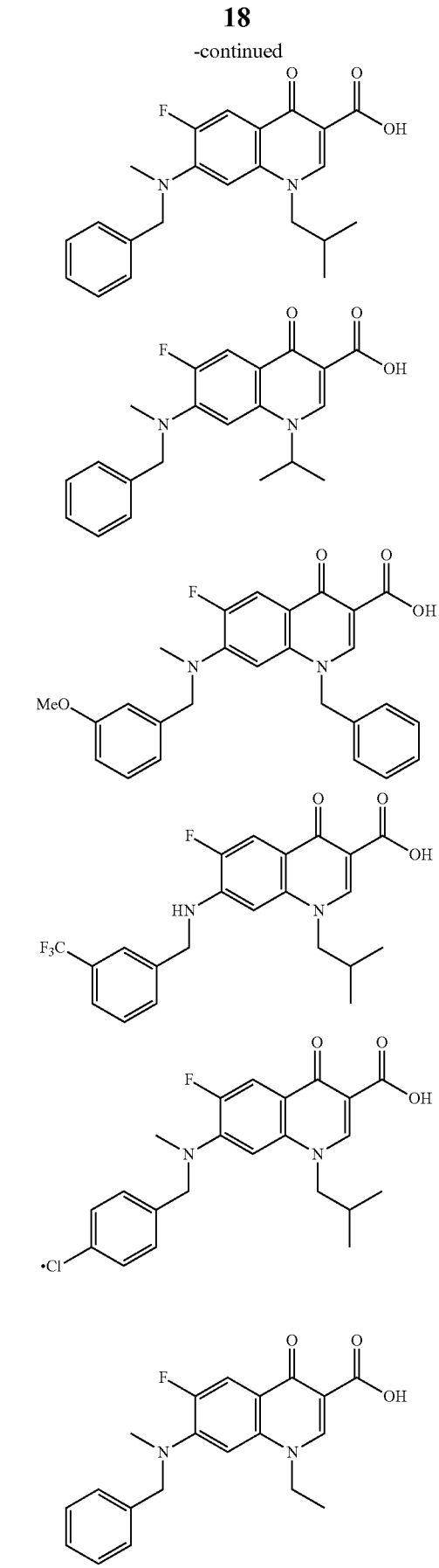

-continued

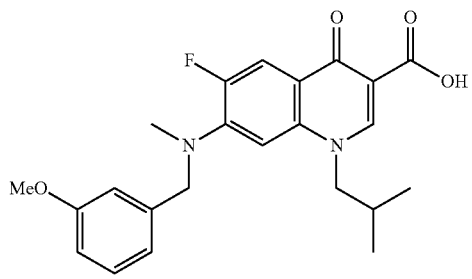

In some embodiments, the compound has the following structure:

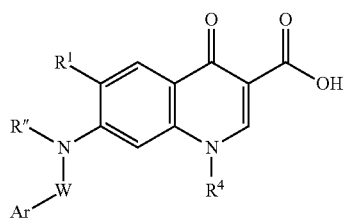

wherein each of R", Ar, W, and R⁴ is as defined above and described herein. In some embodiments, R" is an alkyl (e.g., methyl). In some embodiments, $R^1$ is a halogen (e.g., fluoro). In some embodiments, W is a carboxy (e.g., carbonyl). In some embodiments, Ar is unsubstituted or substituted phenyl (e.g. phenyl). In some embodiments, R⁴ is substituted or unsubstituted alkyl (e.g., isobutyl, benzyl).

In some embodiments, the compound is selected from;

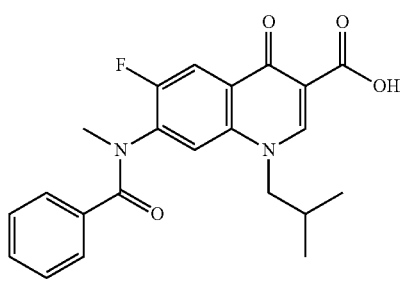

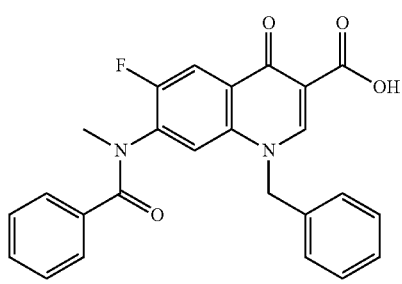

-continued

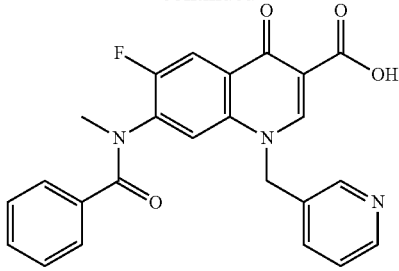

In some embodiments, the compound has the following structure:

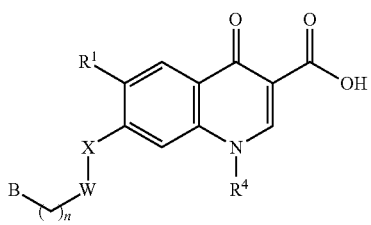

wherein each of $R^1$, $R^4$, X, n, W, B, and Ar is as defined above and described herein. In one embodiment, X is nitrogen. In another embodiment, n is equal to 1. In a further embodiment, W is a bond, and a base addition salt is formed from sodium, potassium, magnesium, or calcium.

In some embodiments, the compound has the following structure:

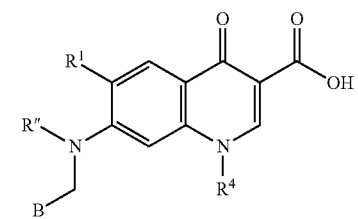

wherein each of R", $R^1$, B, and $R^4$ is as defined above and described herein. In some embodiments, R" is an alkyl (e.g., methyl). In some embodiments, $R^1$ is a halogen (e.g., fluoro). In some embodiments, B is unsubstituted or substituted cycloalkyl (e.g. cyclohexyl, piperidinyl). In some embodiments, R⁴ is substituted or unsubstituted alkyl (e.g., isopropyl, isobutyl, ethyl, benzyl).

In some embodiments, the compound is selected from:

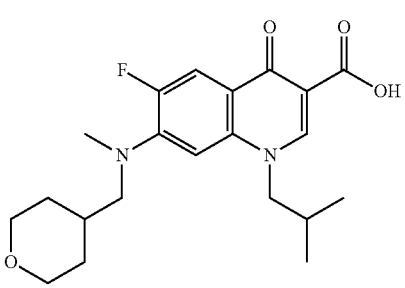

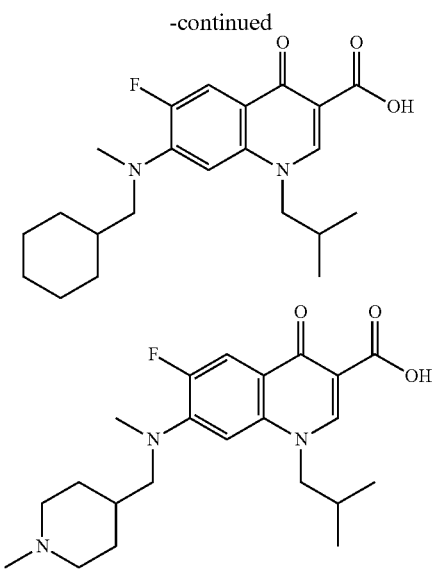

In one aspect, the invention relates to a method of treating a neoplastic or inflammatory or metabolic disorder in a subject, comprising administering a pharmaceutically effective amount of a compound or composition described herein.

Also provided herein are methods of treating a disease associated with expression or activity of MCT1, MCT2, MCT3, MCT4, CD147, NFkB, p53 in a subject comprising administering to the patient a therapeutically effective amount of a compound described herein. For example, provided herein are methods of treating various cancers in mammals specifically including humans, dogs, cats, and farm animals, including hematologic malignancies (leukemias, lymphomas, myelomas, myelodysplastic and myeloproliferative syndromes) and solid tumors (carcinomas such as prostate, breast, lung, colon, pancreatic, renal, brain, —CNS, skin, cervical, ovarian as well as soft tissue and osteo- sarcomas, and stromal tumors), inflammatory disorders such as rheumatoid arthritis, osteoarthritis, psoriatic arthritis, multiple scelorisis, systemic lupus, systemic sclerosis, vasculitis syndromes (small, medium and large vessel),atherosclerosis, psoriasis and other dermatological inflammatory disorders (such as pemphigous, pemphigoid, allergic dermatitis),and urticarial syndromes comprising administering a compound represented by formula I.

Also provided are compounds represented by formula I for use in therapy and/or for the manufacture of a medicament for the treatment of a disease associated with expression or activity of MCT1, MCT2, MCT3, MCT4, CD147, NFkB, p53 in a subject.

The compounds and compositions described herein may be administered intravenously, intraperitoneally, or orally.

In some embodiments, the present invention provides a compound selected from:
7-(benzyl(methyl)amino)-6-fluoro-1-isobutyl-4-oxo-1,4-dihydroquinoline-3-carboxylic acid 7-(benzyl(methyl)amino)-6-fluoro-1-isopropyl-4-oxo-1,4-dihydroquinoline-3-carboxylic acid
7-(benzyl(methyl)amino)-1-ethyl-6-fluoro-4-oxo-1,4-dihydroquinoline-3-carboxylic acid 1-benzyl-6-fluoro-743-methoxybenzyl)(methyl)amino)-4-oxo-1,4-dihydroquinoline-3-carboxylic acid 6-fluoro-1-isobutyl-7-(methyl(thiophen-2-ylmethyl)amino)-4-oxo-1,4-dihydroquinoline-3-carboxylic acid
6-(azetidine-1-carbonyl)-1-isobutyl-4-oxo-7-(2-(trifluoromethyl)benzyl)-1,4-dihydroquinoline-3-carboxylic acid
6-(azetidine-1-carbonyl)-1-isopropyl-4-oxo-7-(2-(trifluoromethyl)benzyl)-1,4-dihydroquinoline-3-carboxylic acid
6-(azetidine-1-carbonyl)-1-cyclopropyl-4-oxo-7-(2-(trifluoromethyl)benzyl)-1,4-dihydroquinoline-3-carboxylic acid
6-(azetidine-1-carbonyl)-7-((3,5-dimethyl-1H-pyrazol-1-yl)methyl)-1-isobutyl-4-oxo-1,4-dihydroquinoline-3-carboxylic acid
7-((4-chlorobenzyl)(methyl)amino)-6-fluoro-1-isobutyl-4-oxo-1,4-dihydroquinoline-3-carboxylic acid
6-fluoro-1-isobutyl-4-oxo-7-((3-(trifluoromethyl)benzyl)amino)-1,4-dihydroquinoline-3-carboxylic acid
6-fluoro-1-isobutyl-743-methoxybenzyl)(methyl)amino)-4-oxo-1,4-dihydroquinoline-3-carboxylic acid
6-fluoro-1-isobutyl-7-(N-methylbenzamido)-4-oxo-1,4-dihydroquinoline-3-carboxylic acid
1-benzyl-6-fluoro-7-(N-methylbenzamido)-4-oxo-1,4-dihydroquinoline-3-carboxylic acid
6-fluoro-1-isobutyl-7-(methyl((1-methylpiperidin-4-yl)methyl)amino)-4-oxo-1,4-dihydroquinoline-3-carboxylic acid
6-fluoro-1-isobutyl-7-(methyl((tetrahydro-2H-pyran-4-yl)methyl)amino)-4-oxo-1,4-dihydroquinoline-3-carboxylic acid
7-((cyclohexylmethyl)(methyl)amino)-6-fluoro-1-i sobutyl-4-oxo-1,4-dihydroquinoline-3-carboxylic acid
6-fluoro-7-((3-fluorobenzyl)(methyl)amino)-1-isobutyl-4-oxo-1,4-dihydroquinoline-3-carboxylic acid
6-fluoro-1-isopropyl-7-(methyl(pyridin-3-ylmethyl)amino)-4-oxo-1,4-dihydroquinoline-3-carboxylic acid
6-fluoro-74(4-fluorobenzyl)(methyl)amino)-1-isopropyl-4-oxo-1,4-dihydroquinoline-3-carboxylic acid
bis(trifluoromethyl)benzyl)(methyl)amino)-6-fluoro-1-isobutyl-4-oxo-1,4-dihydroquinoline-3-carboxylic acid
6-fluoro-1-isobutyl-7-(methyl(thiazol-5-ylmethyl)amino)-4-oxo-1,4-dihydroquinoline-3-carboxylic acid
6-fluoro-1-isobutyl-7-(methyl(oxazol-5-ylmethyl)amino)-4-oxo-1,4-dihydroquinoline-3-carboxylic acid
6-fluoro-7-(N-methylbenzamido)-4-oxo-1-(pyridin-3-ylmethyl)-1,4-dihydroquinoline-3-carboxylic acid or a pharmaceutically-acceptable salt thereof.

In one aspect, the invention relates to a composition comprising a compound described herein, or a pharmaceutically acceptable derivative thereof, and a pharmaceutically acceptable carrier, adjuvant, or vehicle. The amount of compound in compositions will normally be an amount effective to measurably inhibit monocarboxylate transport, in a biological sample or in a patient. However, compositions containing a fraction of the effective amount may be employed for multiple dosing. In some embodiments, a composition of this invention is formulated for oral administration, intravenous, subcutaneous, intraperitoneal or dramatological application to a patient.

The term "patient", as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

Compounds and compositions described herein are generally useful for the inhibition of monocarboxylate transport. The activity of a compound may be assayed in vitro, in vivo or in a cell line. Detailed conditions for assaying a compound utilized as an inhibitor of monocarboxylate transport are set forth in the Examples below. The compounds and compositions described herein can be administered to cells in culture, e.g. in vitro or ex vivo, or to a subject, e.g., in vivo, to treat and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to reduce at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, "a prophylactically effective amount" of the compound refers to an amount effective, upon single- or multiple-dose administration to the subject, in reducing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc, and companion animals (dog, cat, horse etc).

Provided compounds are inhibitors of monocarboxylate transport and are therefore useful for treating one or more disorders associated with activity of monocarboxylate transport. Thus, in certain embodiments, the present invention provides a method for treating a monocarboxylate transport-mediated disorder comprising the step of administering to a patient in need thereof a compound of the present invention, or pharmaceutically acceptable composition thereof.

The term "monocarboxylate transport-mediated" disorder or condition, as used herein, means any disease or other deleterious condition in which monocarboxylate transport is known to play a role. Accordingly, another embodiment of the present invention relates to treating or lessening the severity of one or more diseases in which monocarboxylate transport is known to play a role. Specifically, the present invention relates to a method of treating or lessening the severity of a proliferative disorder. Disorders are set forth in detail below.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast, cervical, ovarian, liver, melanoma, brain, —CNS, head and neck, osteosarcoma, gastrointestinal, pancreatic, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS- Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non- Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, kinase inhibitors, immunotherapy, cancer metabolism therapies, hormonal therapy, and anti-angiogenic therapies.

Anti-Angiogenic Therapy

Compounds and methods described herein may be used to treat a disease or disorder associated with angiogenesis. Diseases associated with angiogenesis include cancer, cardiovascular diseases and mascular degeneration. Angiogenesis is the physiological processes involving the growth of new vessels from pre-existing blood vessels. Angiogenesis is the normal and vital process in growth and development, as well as in wound healing and in granular tissue. However, it is also a fundamental step in the transition of tumors from a dormant state to a malignant one. Angiogenesis may be a target for combating diseases characterized by either poor vascularization or abnormal vasculature. Application of specific compounds that may inhibit the creation of new blood vessels in the body may help combat such diseases. The presence of blood vessels where there should be none may affect the normal properties of a tissue, increasing the likelihood of failure. The absence of blood vessels in a repairing or otherwise metabolically active tissue may inhibit repair or other essential functions. Several diseases such as ischemic chronic wounds are the results of failure or insufficient blood vessel formation and may be treated by a local expansion of blood vessels, thus bringing new nutrients to the site, facilitating repair. Other diseases such as age-related macular degeneration may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment for vascular injuries. In vitro studies clearly demonstrated that VEGF is a potent stimulator of angiogenensis because, in the presence of this growth factor, plated endothelial cells will proliferate and migrate, eventually forming tube structures resembling capillaries.

Tumors induce blood vessel growth by secreting various growth factors (e.g. VEGF). Growth factors such as bFGF and VEGF can induce capillary growth into the tumor, which may supply required nutrients allowing for tumor expansion. Angiogenesis therefore represents an attractive target for the treatment of cancer and cardiovascular diseases. It is a potent physiological process that underlies the natural manner in which our bodies responds to a diminution of blood supply to vital organs, namely the production of new collateral vessels to overcome the ischemic insult. Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina causing loss of vision. Antiangiogenic therapy can include kinase inhibitors targeting vascular endothelial growth factor (VEGF) such as sutinib, sorafenib, or monoclonal antibodies or recerptor "decoys" to VEGF or VEGF-Trap or thalidomide or its analogs (lenalidimide, pomalidomide), or agents targeting non-VEGF angiogenic targets such as fibroblast growth factor (FGF), angiopoietins, or angiostatin, or ensostatin.

Immunosuppression

The body immune system detects foreign objects and organisms such as bacteria, virus, and other pathogens, and protects the body by eliminating those harmful matters. Sometimes, those immune system responses against foreign pathogens or tissues become more harmful to the host, for example, allergies to food and extrinsic antigens such as pollen and respiratory diseases such as asthma. In addition, strong responses against transplant tissues or organs occur, leading to the rejection of them. In such cases, immunosuppressive drugs are needed to avoid those complications. Additionally, the body's immune system does not exert responses against self-tissues or self-antigens under normal circumstances. However, in some cases, body exerts a strong immune response against self-tissues aggressively leading to a variety of autoimmune diseases such as rheumatoid arthritis, multiple sclerosis, type I diabetes, etc. Most immune responses are initiated and controlled by T helper lymphocytes, which respond to antigens.

A number of immunosuppressive therapies have been developed over the last decades. These include rapamycin, which disrupts the cytokine such as IL-2-driven T-cell proliferation by intereferring with TOR (Target of Rapamycin) function. However, rapamycin has been shown to cause significant side effects including hyperlipidemia (Hong et al, Semin. Nephrol., 10(2); 108-125, 2000).

MCTs may act as biomarkers and compounds and compositions described herein may also be used to treat selectively sub-population of patients who express either MCT1 or MCT4 or both. It is known that a patient's response to a drug may be dependent upon patient's genetic profile and/or the type of the disease. It has been demonstrated that MCT4 is a biomarker that predicts poor overall survival of aggressive triple negative breast cancer patients.

Abbreviations:
atm Atmosphere
aq. Aqueous
BINAP 2,2'-bis(diphenylphosphino)-1,1'-binaphthyl
Boc tert-butoxycarbonyl
CDI N,N'-Carbonyldiimidazole
DCC N,N-Dicyclohexylcarbodiimide
DCM Dichloromethane
DBU Diaza(1,3)bicyclo[5.4.0]undecane
DEA N,N-Diisopropyl ethylamine
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
EA Ethyl acetate
EDCI N[3-(dimethylamino)propyl]N'-ethylcarbodiimide hydrochloride
EDC 1-Ethyl-3 -(3 -dimethyl aminopropyl)carbodiimide
Et$_2$O Diethylether
EtOAc Ethyl acetate
EtOH Ethanol
EtI Iodoethane
Et Ethyl
Fmoc 9-fluorenylmethyloxycarbonyl
h hour(s)
HetAr Heteroaryl
HOBt N-Hydroxybenzotriazole
HBTU O-(Benzotriazol-1-yl)-N,N,N',N'-tetramethyluronium hexafluorophosphate
HPLC High performance liquid chromatography
LAH Lithium aluminium hydride
LCMS HPLC mass spec
MCPBA m-Chlorbenzoic acid
MeCN Acetonitrile
MeOH Methanol
min Minutes
MeI Iodomethane
MeMgCl Methyl magnesium chloride
Me Methyl
MTS 3-(4,5-dimethylthiazol-2-yl)-5-(3-carb oxymethoxyphenyl)-2-(4-sulfophenyl)-2H-tetrazolium
MTT 3-(4,5-dimethylthiazol-2-yl)-2,5-diphenyltetrazolium bromide
n-BuLi 1-Butyllithium
NaOAc Sodium acetate
NMR Monocarboxylate magnetic resonance
NMP N-Methyl pyrrolidinone
nBuLi 1-Butyl lithium
o.n. Over night
Ph phenyl
RT, rt, r.t. Room temperature
TEA Triethylamine
THF Tetrahydrofurane
nBu normal Butyl
OMs Mesylate or methane sulfonate ester
OTs Tosylate, toluene sulfonate or 4-methylbenzene sulfonate ester
PCC Pyridinium chlorochromate
PPTS Pyridinium p-toluenesulfonate
TBAF Tetrabutylammonium fluoride
pTsOH p-Toluenesulfonic acid
SPE Solid phase extraction (usually containing silica gel for mini-chromatography)
sat. Saturated
PG Protecting group
mins minutes Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations —A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

General Synthetic Methods

Several general methods for preparing compounds of Formula I are illustrated in the following Schemes and Examples. Starting materials and the requisite intermediates are in some cases commercially available or can be prepared according to literature procedures (Bioorg. Med. Chem. 16, 2008, 9487-9497; Bioorg. Med. Chem. 16, 2008, 10031-10310; Synthetic Comm. 35, 2005, 761-764) or as illustrated herein. In the steps where product was obtained as a mixture of isomers, pure isomers can be easily separated using chromatographic methods in the literature.

It is understood that the functional groups present in compounds described in the Schemes below can be further manipulated, when appropriate, using the standard functional group transformation techniques available to those skilled in the art, to provide desired compounds described in this invention. Other variations or modifications, which will be obvious to those skilled in the art, are within the scope and teachings of this invention.

Certain quinolone carboxylic acid compounds of Formula I, wherein the $R^4$ group is an alkyl, B is an aryl or heteroaryl group, and $R^1$ group is hydrogen, fluorine, or optionally substituted carboxylic acid, carboxylic ester, carboxy amides, cyano, etc., can be prepared in accordance with general Scheme 1.

Scheme 1

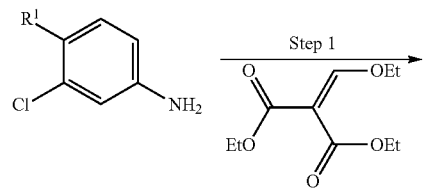

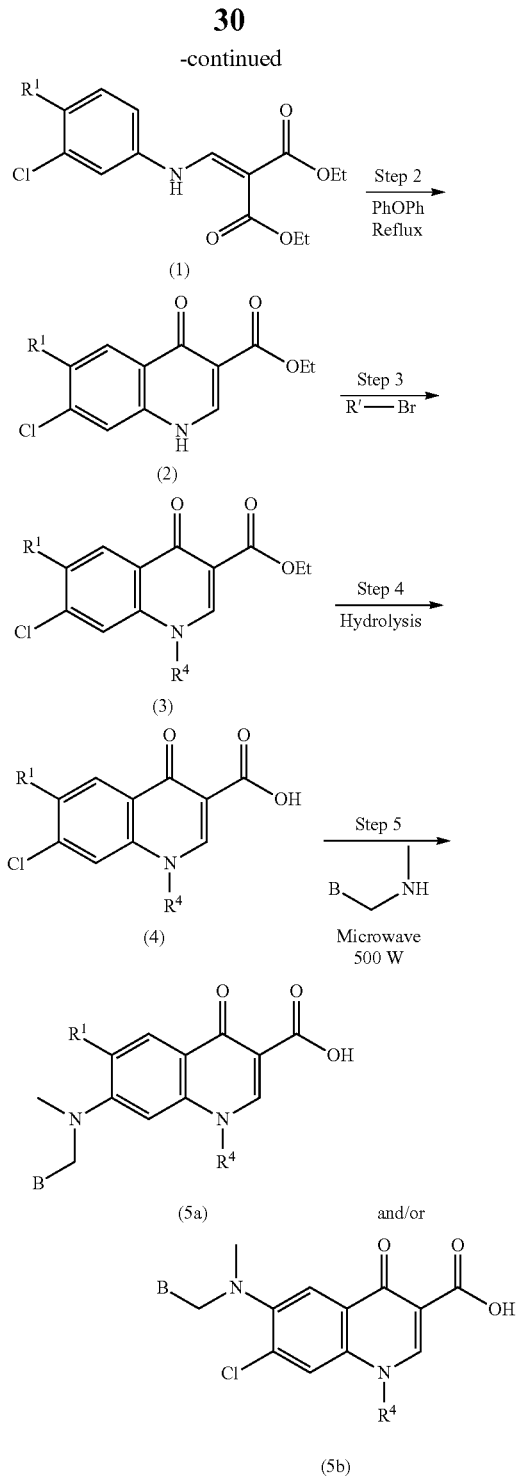

In Scheme 2, the group Ar is selected from aryl and heteroaryl optionally substituted with one or more substituents and, the X is an alkyl group, and the $R^4$ group is an alkyl, and $R^1$ group is hydrogen, fluorine, or optionally substituted amine, carboxylic acid, carboxylic ester, carboxy amides, cyano, etc., can be prepared in accordance with general Scheme 2.

Scheme 2
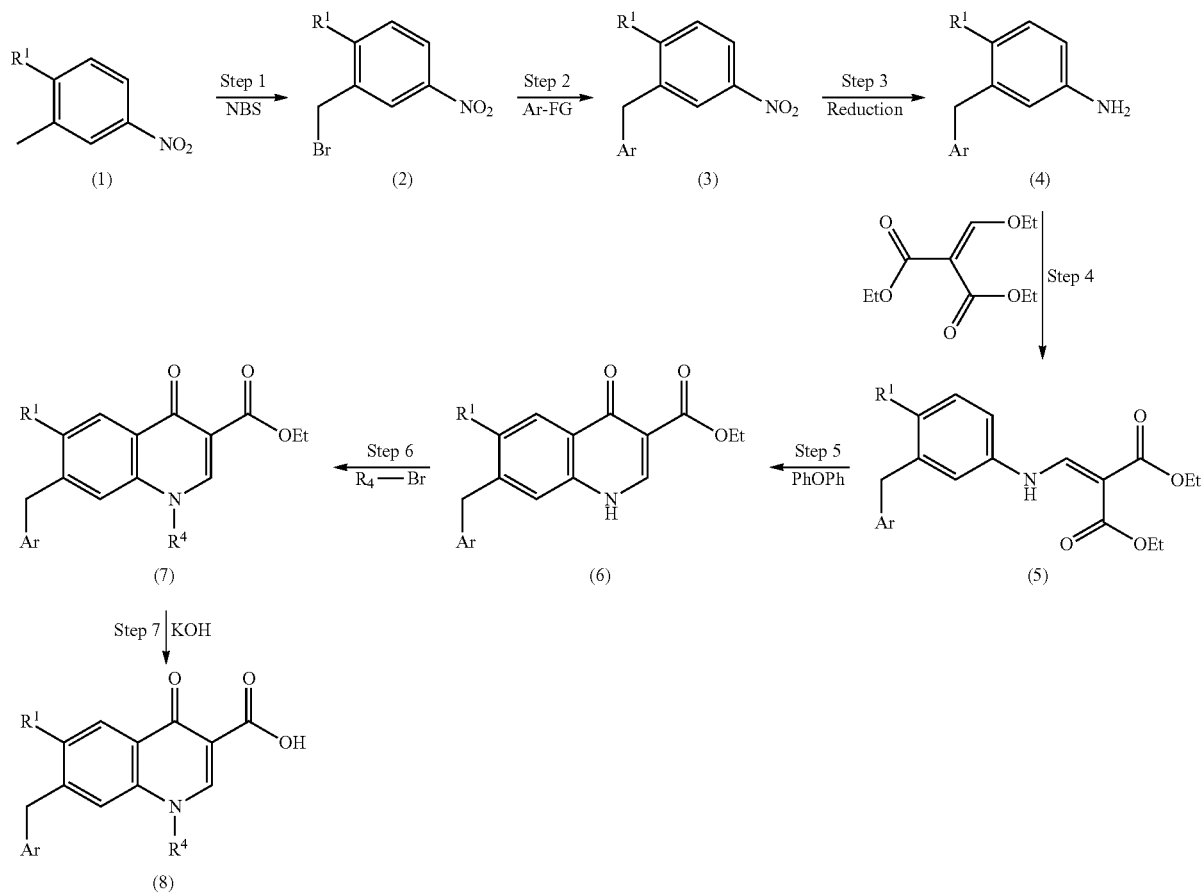
In Scheme 3 and Scheme 5, a general method is described for the preparation of certain napthyridone compounds of Formula I, wherein the $R^4$ group is an alkyl.
Scheme 3
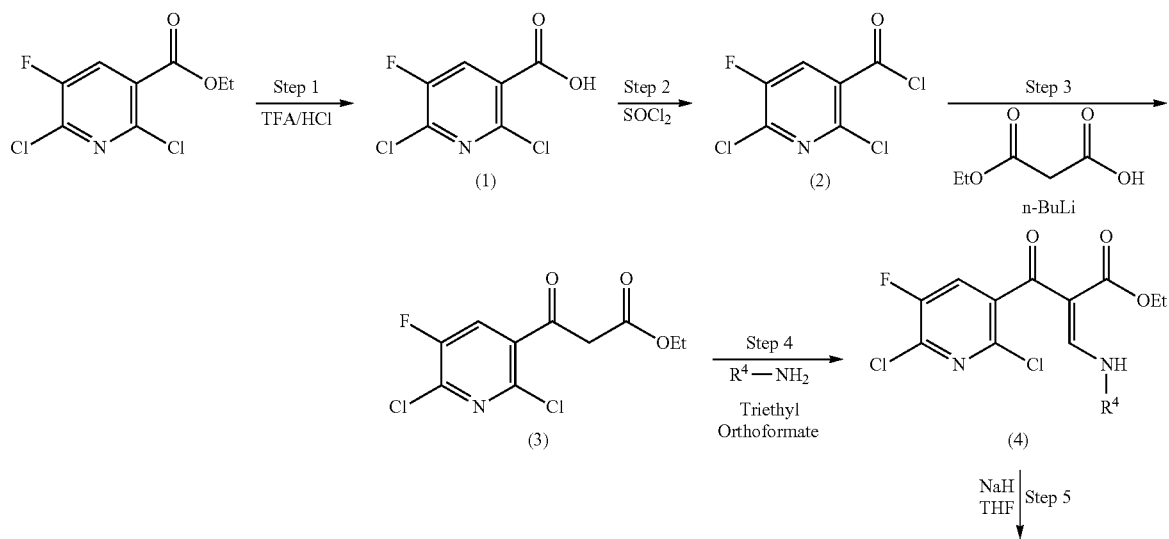

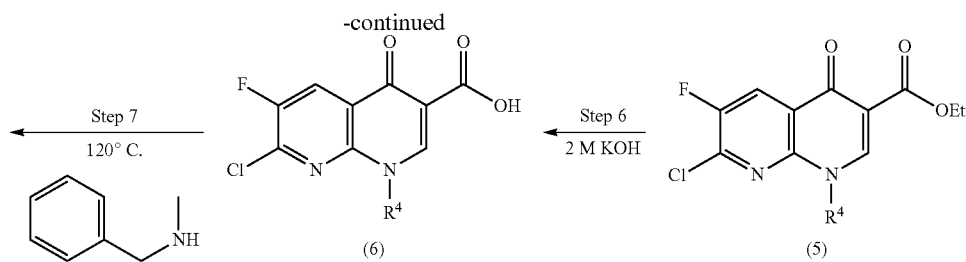
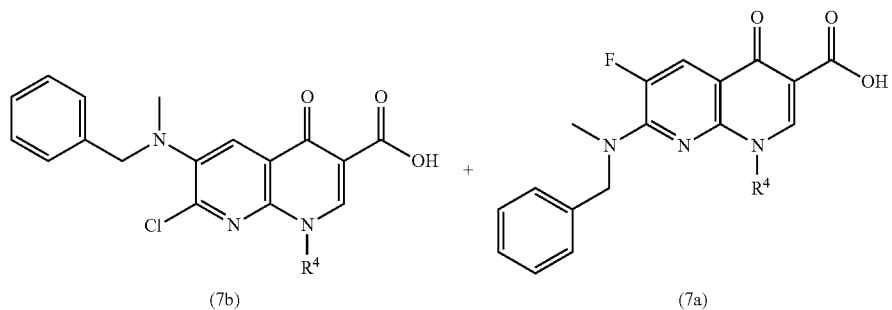
In Scheme 4, a general method is described for the preparation of certain pyrazopyridone compounds of Formula I, wherein the $R^4$ group is an alkyl, and $R^1$ group is hydrogen, fluorine, or optionally substituted carboxylic acid, carboxylic ester, carboxy amides, cyano, etc.
Scheme 4
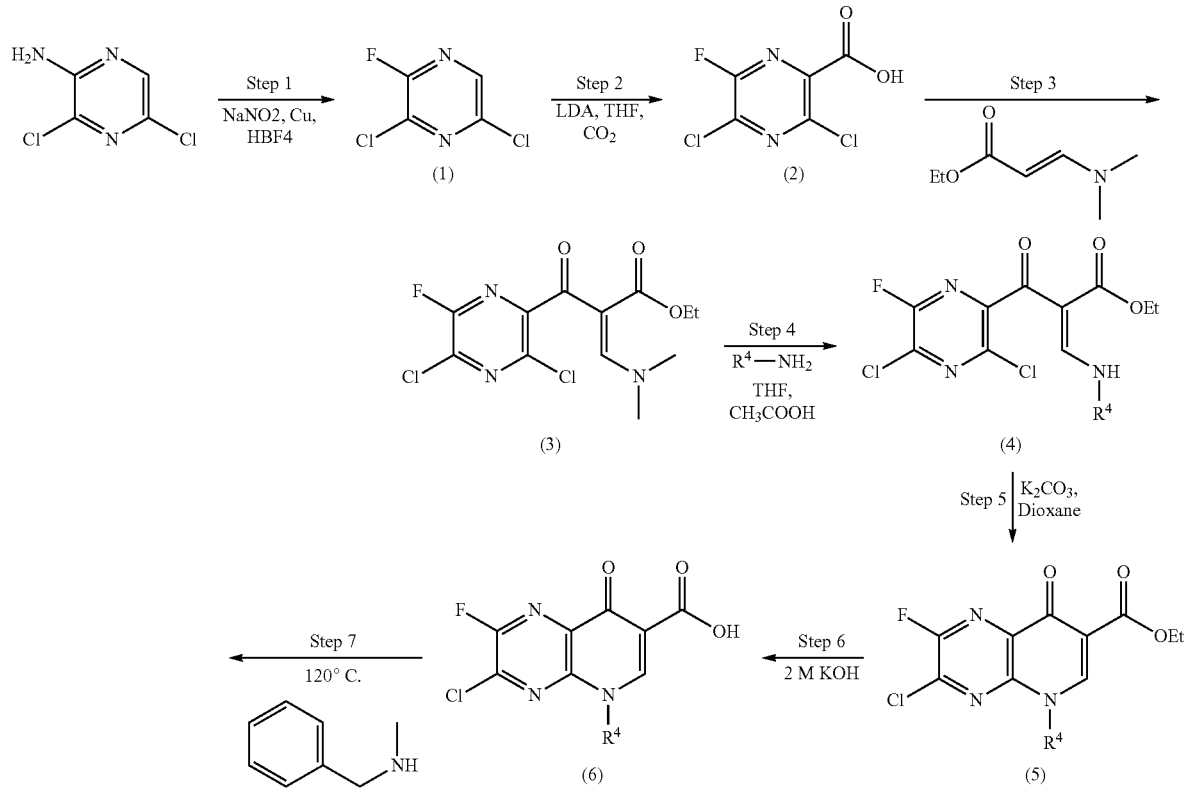

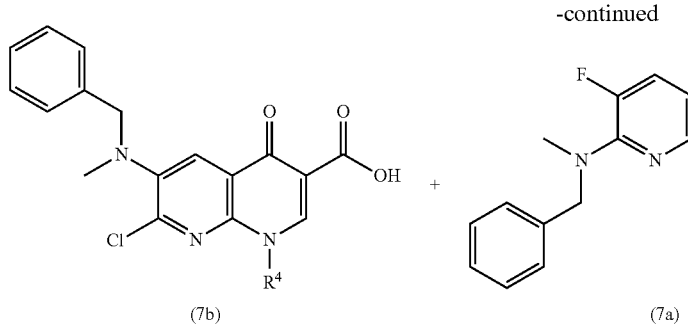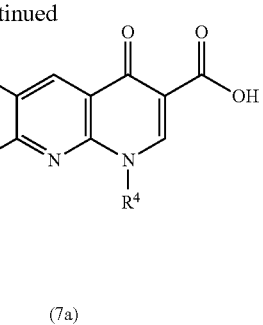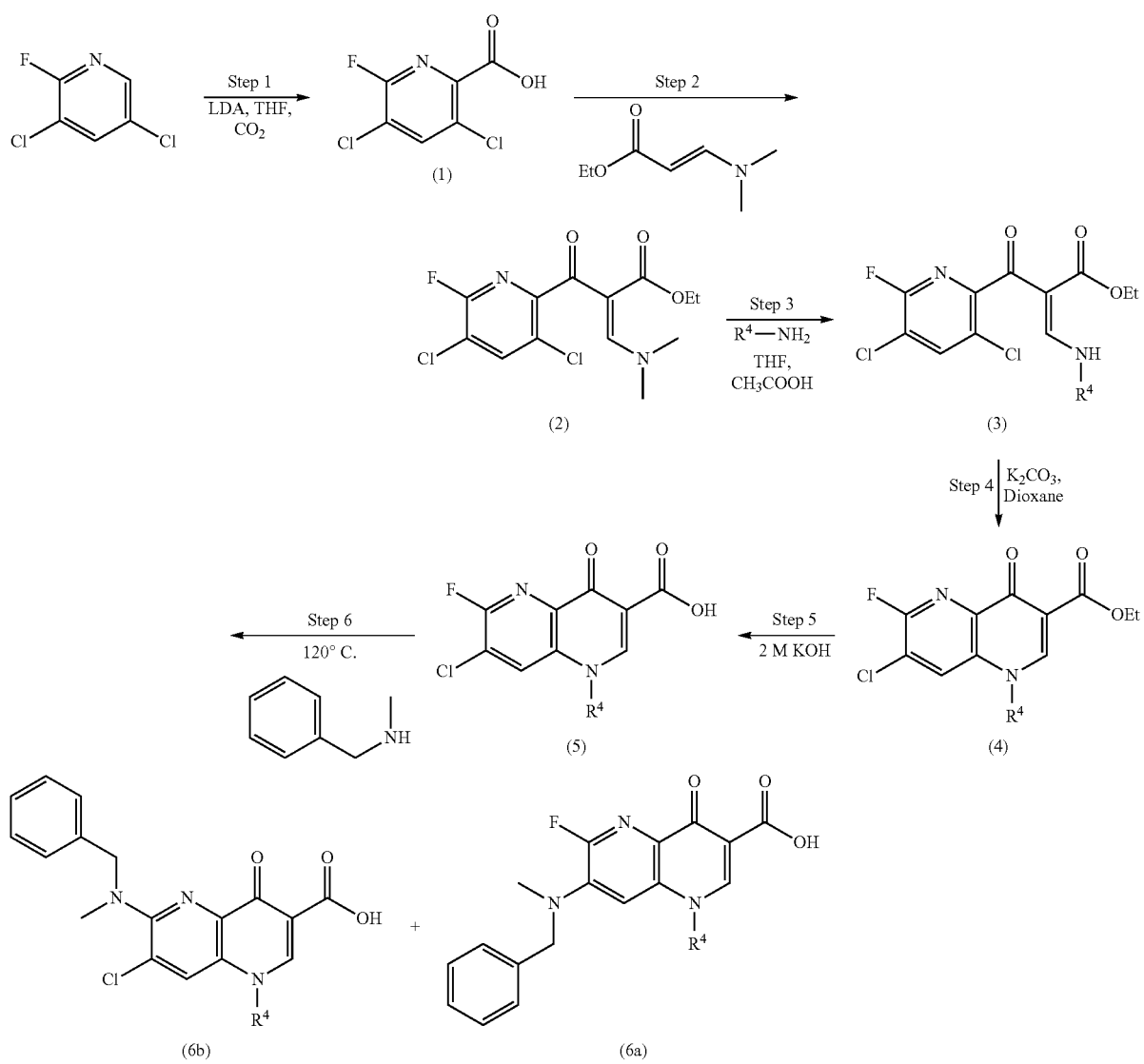

In a similar manner the following compounds were synthesized:

EXAMPLE 1

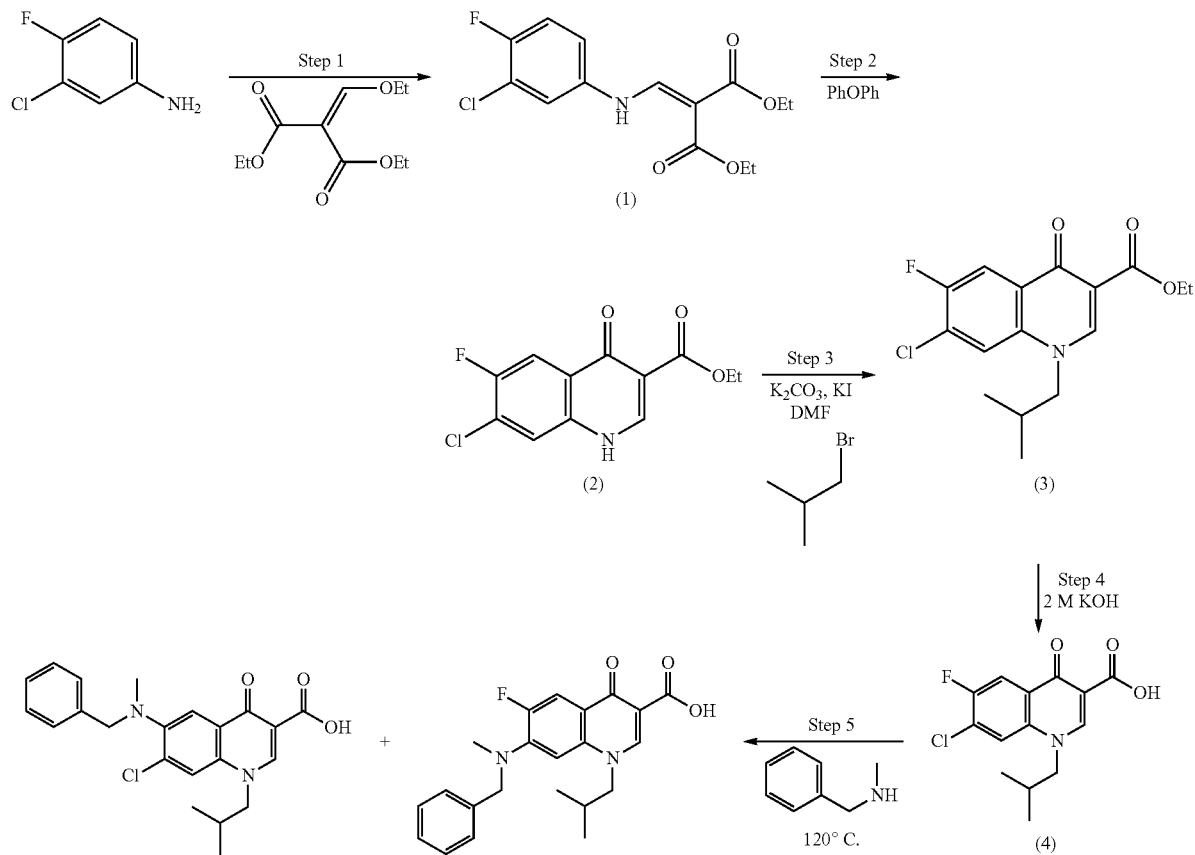

Step 1

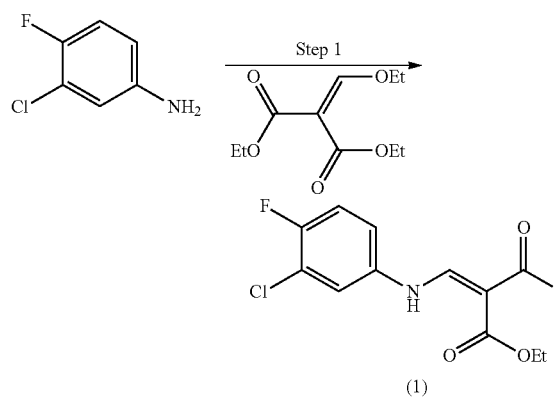

Procedure

In a 250 mL, 3-neck round-bottomed flask, 3-Chloro-4-fluoroaniline (20 g, 137.4 mmol) was added with toluene (100 mL). To this reaction mixture, diethyl-2-(ethoxymethylene) malonate (29.7 g, 137.4 mmol) was added at 25° C. The reaction mixture was heated at reflux under stirring for 1 h, then cooled to 30° C. and added water (150 mL). The mixture was extracted with EtOAc (30 mL×3). The combined organic layer was washed with brine solution, dried over anhydrous Na$_2$SO$_4$ and concentrated under reduced pressure to obtain 40 g of crude product which was triturated with minimum hexanes to obtain diethyl-2-((3-chloro-4-fluorophenylamino) methylene)malonate (1) 36 g; Yield (50.1%); 1H NMR (400 MHz, DMSO-d$_6$): δ 10.61 (d, J=12.8, 1H), 8.29 (d, J=13.6, 1H), 7.72-7.74 (m, 1H), 7.4-7.42 (m, 2H), 4.12-4.2 (m, 4H), 1.24-1.26 (m, 6H); MS (ESI): 316.1(M+H).

Step 2

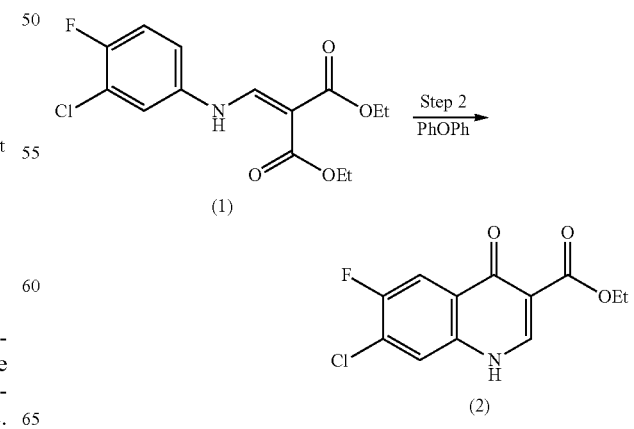

Procedure

In a 500 mL, 3-neck round-bottomed flask, diphenylether (200 mL) was heated up to 150° C. To this falsk, diethyl 2-{(3-chloro-4-fluorophenylamino)methylene}malonate (1) (36 g, 114.1 mmol) was added. The reaction mixture was stirred at that temperature for 4-5 h. The reaction mixture was then cooled to room temperature, and hexanes (1 L) was added to precipitate the compound. The solid obtain was filtered to obtain 16 g of crude compound. The crude product contained traces of regioisomer formed during cyclization. This product was used for the next step without further purification.

Step 3

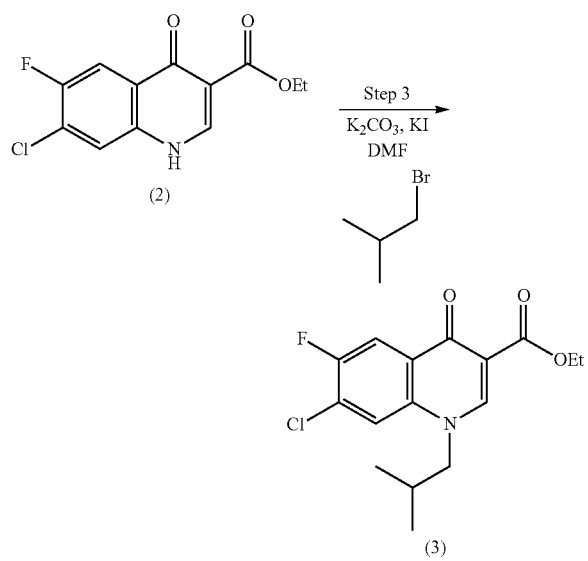

Procedure

In a 100 mL, 3-neck round-bottomed flask, ethyl 7-chloro-6-fluoro-4-oxo-1,4-dihydroquinoline-3-carboxylate (2) (3.8 g, 14.09 mmol) and K$_2$CO$_3$ (9.7 g, 70.45 mmol) were suspended in DMF (30 mL) and the reaction mixture was stirred for 15 min at room temperature. To this mixture, 1-bromo-2-methyl propane (11.6 g, 84.55 mmol) and potassium iodide (0.25 g, 1.409 mmol) were added and the resulting mixture was heated at 80° C. for 24 h. The reaction mixture was cooled and filtered, and the filtrate was evaporated under reduced pressure to obtain 5.3 g of the crude product. The crude product was purified by silica gel column chromatography to obtain 3.3 g of ethyl 7-chloro-6-fluoro-1-isobutyl-4-oxo-1,4-dihydroquinoline-3-carboxylate (3); Yield (71.9%); $^1$H NMR: (400 MHz, DMSO-d6): δ 8.66 (s, 1H), 8.21 (d, J=6, 1H), 8.04 (d, J=9.2, 1H), 4.21-4.27 (m, 4H), 2.10-2.13(m, 1H), 1.27-1.31 (m, 3H), 0.88-0.90 (m, 6H); MS (ESI): 326.2(M+H).

Step 4

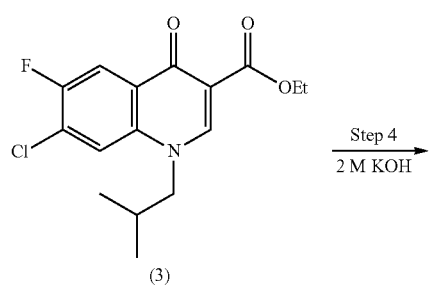

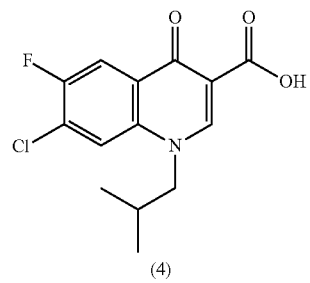

Procedure

In a 100 mL, 3-Neck round-bottomed flask, intermediate (3) (3.3 g, 10.13 mmol) was added with THF:Water (1:1) (10 mL). To this mixture, 2M KOH solution (20 mL) was added dropwise maintaining the temperature at 0° C. The resulting mixture was stirred at room temperature for 2 h and reaction completion was monitored by TLC. The mixture was cooled to 0° C. and acidified to pH 3-4 with 4N HCl. The solid compound obtain was filtered to obtain 2.1 g of the crude product. The product was extracted with EtOAc (50 mL×3) and the combined organic layer was washed with brine solution, dried over anhydrous Na$_2$SO$_4$ and concentrated under reduced pressure to obtain, after trituration with minimum hexane, 2 g of 7-chloro-6-fluoro-1-isobutyl-4-oxo-1,4-dihydroquinoline-3-carboxylic acid; Yield (66.6%); $^1$H NMR: (400 MHz, CDCl$_3$): δ 14.45 (br s, 1H), 8.69 (s, 1H), 8.26 (d, J=8.4, 1H), 7.65 (d, J=5.2, 1H), 4.07-4.09 (m, 2H), 2.25-2.32 (m, 1H), 1.02-1.05 (m, 6H); MS (ESI): 299.2(M+H).

Step 5

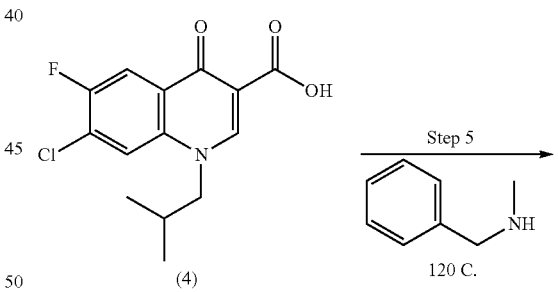

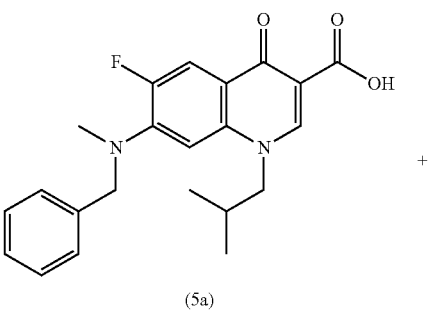

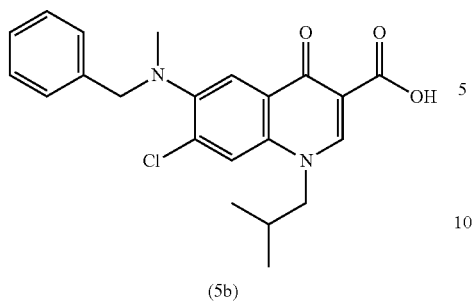

(5b)

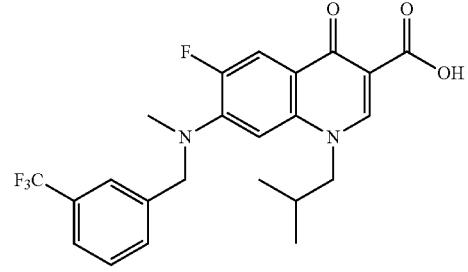

(5)

Procedure

In a 25 mL single neck round-bottomed flask, the intermediate 4 (0.5 g, 1.679 mmol) from Example 1 and N-methyl-1-(3-(trifluoromethyl)phenyl)methanamine (1.5 g, 8.39 mmol) were added and heated to 120° C. for 24 h. The reaction was monitored by TLC for completion followed by an aqueous worked up and acidified with 1N HCl to pH 3-4. The aqueous layer was extracted with EtOAc and the organic layer was dried over anhydrous $Na_2SO_4$. The solvent was evaporated under reduced pressure to obtain the crude product which was purified by silica gel column chromatography to provide pure 6-fluoro-1-isobutyl-7-(methyl(3-(trifluoromethyl)benzyl)amino)-4-oxo-1,4-dihydroquinoline-3-carboxylic acid (5), (25 mg); Yield; 3.3%; $^1$H NMR (400 MHz, DMSO-$d_6$): δ 15.5 (s, 1H), 6.83-8.71 (m, 7H), 4.75 (s, 2H), 4.20 (d, 2H), 3.13 (s, 3H), 1.83-1.86 (m, 1H), 0.74-0.76 (d, 6H); MS(ESI): 451.1(M+H); HPLC: 92.07%.

Procedure

In a 25 mL single neck flask, the product from step 4 (3.2 g, 10.77 mmol) and N-benzyl methyl amine (6.5 g, 53.87 mmol) were added and heated at 120° C. for 24 h. The reaction completion was monitored by TLC followed by aqueous work up. The resulting mixture was extracted with EtOAc (50 mL×3) and washed with 5N HCl solution (15 mL×2), dried over anhydrous $Na_2SO_4$ to obtain the crude product after solvent evaporation in vacuo. The product was recrystalized from EtOAc (10 vol) to obtain 1.5 g of pure 7-(benzyl(methyl)amino)-6-fluoro-1-isobutyl-4-oxo-1,4-dihydroquinoline-3-carboxylic acid (5a); Yield (36%); $^1$H NMR (400 MHz, DMSO-$d_6$): δ 15.45 (d, 1H), 6.84-7.90 (m, 8H), 4.70 (s, 2H), 4.25-4.26 (d, 2H), 3.17 (s, 3H), 1.85-1.88 (m, 1H), 0.76-0.78 (d, 6H); MS (ESI): 383.2 (M+H); HPLC: 95.2%.

EXAMPLE 2

Mother liquor remained from the synthesis of Example 1 was concentrated under reduced pressure to obtain the crude 5b. The product was purified by column chromatography (silica gel) to obtain 10 mg of pure 6-(benzyl(methyl)amino)-7-chloro-1-isobutyl-4-oxo-1,4-dihydroquinoline-3-carboxylic acid (5b): Yield, 5%; $^1$H NMR (400 MHz, DMSO-d6): δ 15.16 (d, 1H), 8.95 (s,1H), 7.28-8.27 (m, 7H), 4.41-4.43 (d, 2H), 4.3 (s, 2H), 2.74 (s, 3H), 2.1-2.2 (m, 1H), 0.88-0.90 (d, 6H); MS (ESI): 399(M+H); HPLC: 93.57%.

EXAMPLE 3

EXAMPLE 4

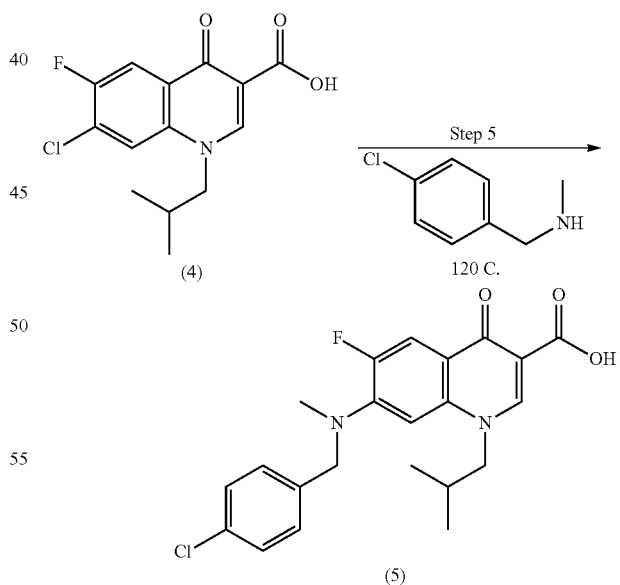

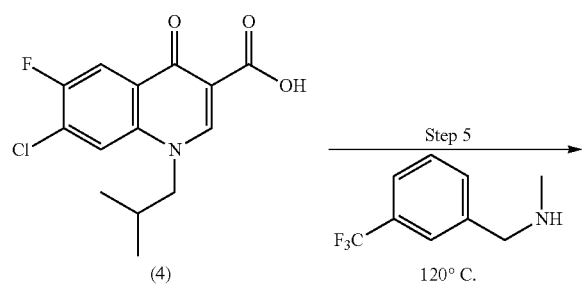

Procedure

In a 25 mL single neck round-bottomed flask, the intermediate 4 (1 g, 3.35 mmol) from Example 1 and N-(4-chlorobenzyl)-N-methylamine (2.6 g, 16.7 mmol) were added and the mixture was heated to 120° C. for 24 h. Reaction was monitored by TLC to completion and was added 10 mL water followed by acidification with dil. HCl to pH 3-4. The mixture was extracted with EtOAc (3×50 mL) and the combined organic layer was dried over Na$_2$SO$_4$. The sovent was evaporated under reduced pressure to obtain the crude product which was purified by column chromatography (silica gel) to provide the desired product, 7-((4-chlorobenzyl)(methyl)amino)-6-fluoro-1-isobutyl-4-oxo-1,4-dihydroquinoline-3-carboxylic acid (5), 50 mg; Yield (3.5%); $^1$H NMR (400 MHz, DMSO-d$_6$): δ 15.44 (s, 1H), 6.84-8.70 (m, 7H), 4.66 (s, 2H), 4.24-4.25 (d, 2H), 3.14 (s, 3H), 1.81-1.87 (m, 1H), 0.75-0.77 (d, 6H); MS (ESI): 417.2(M+H); HPLC: 96.35%.

EXAMPLE 5

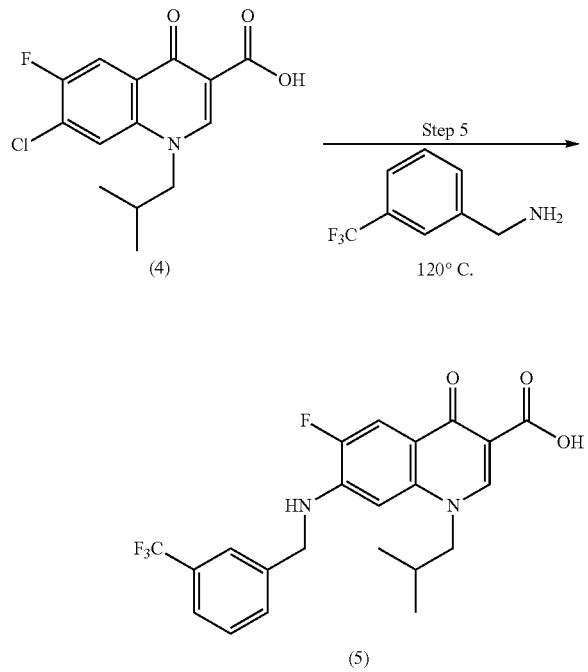 [SMILES: CC(C)Cn1cc(C(=O)O)c(=O)c2cc(F)c(Cl)cc21 ; NCc1cccc(C(F)(F)F)c1 ; CC(C)Cn1cc(C(=O)O)c(=O)c2cc(F)c(NCc3cccc(C(F)(F)F)c3)cc21]

Procedure

In a 25 mL single neck round-bottomed flask Intermediate 4 (0.5 g, 1.683 mmol) from Example 1 and 3-(trifluoromethyl)-N-benzyl amine (1.47 g, 1.42 mmol) were added and the mixture was heated to 120° C. for 24 h. Reaction was monitored by TLC for completion and the mixture was quenched with 15 mL of water and acidified with 4N HCl to pH 3-4. The aqueous layer was extracted with EtOAc (3×25 mL), and the combined organic layer was dried over anhydrous Na$_2$SO$_4$. The solvent was evaporated under reduced pressure to obtain the crude product which was purified by column chromatography (silica gel) to provide the desired product, 6-fluoro-1-isobutyl-4-oxo-7-(3-(trifluoromethyl) benzylamino)-1,4-dihydroquinoline-3-carboxylic acid (5), 25 mg; Yield: 4.0%; $^1$H NMR (400 MHz, DMSO-d$_6$): δ 15.68 (s, 1H), 7.58-7.87 (m, 7H), 6.51-6.53(d, 1H), 4.71-4.73 (d, 2H), 4.15-4.17 (d, 2H), 1.49 (m, 1H), 0.61-0.63 (d, 6H); MS(ESI): 437.1(M+H); HPLC: 97.48%.

EXAMPLE 6

Step 3

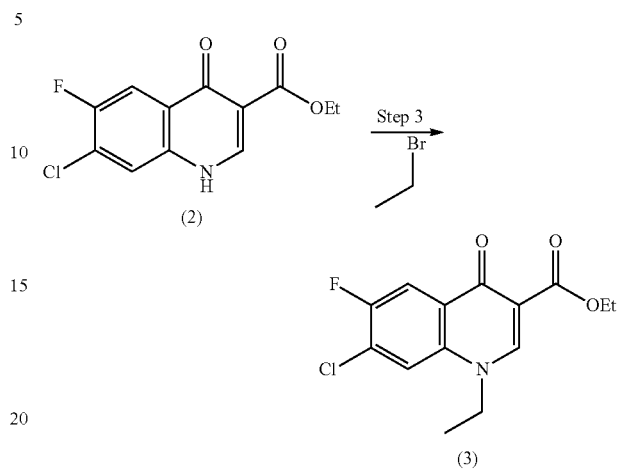

Procedure

In a closed system, ethyl 7-chloro-6-fluoro-1,4-dihydro-4-oxoquinoline-3-carboxylate (2) (1.4 g, 5.19 mmol) from Example 1 and K$_2$CO$_3$ (3.58 g, 25.92 mmol) were suspended in DMF (14 mL) and the reaction mixture was stirred for 15 min at room temperature. To this reaction mixture, bromoethane (3.39 g, 31.15 mmol) and KI (0.09 g, 0.52 mmol) were added, and the reaction mixture was heated at 80° C. for 24 h. The reaction mixture was then cooled and filtered. The filtrate was partitioned between ethyl acetate and brine solution, and the organic phase was separated and washed with brine solution, and the solvent was removed in vacuo to obtain the crude product which was purified by column chromatography (Silica gel). The fractions containing desired compound were collected together and concentrated under reduced pressure to obtain ethyl 7-chloro-1-ethyl-6-fluoro-1,4-dihydro-4-oxoquinoline-3-carboxylate (1.2 g); Yield: 77.57%; $^1$H NMR (400 MHz. CDCl3): δ 8.48 (s, 1H), 8.26 (d, J=9.2, 1H), 7.54 (d, J=5.6, 1H), 4.38-4.43 (m, 2H), 4.21-4.26 (m, 2H), 1.55-1.59 (m, 3H), 1.28-1.43 (m, 3H).

Step 4

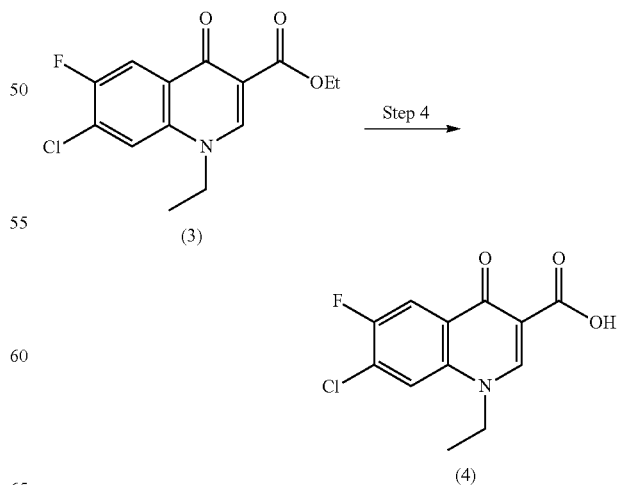

45

Procedure

In a 100 mL, 3-neck round-bottomed flask, the intermediate (3) (1.0 g, 3.36 mmol) from Example 6 was charged with THF: Water (4:1) (20 mL). To this reaction mixture, a 2M NaOH solution (6 mL) was added dropwise maintaining the temperature at room temperature. The reaction mixture was stirred at 80° C. for 2 h and then cooled to 0° C. followed by acidification to pH 3-4 by 4N HCl. The solid obtained was filtered to obtain the crude product. The crude product was extracted with ethyl acetate (50 mL×3). The combined organic layer was washed with brine solution, dried over anhydrous $Na_2SO_4$ and concentrated under reduced pressure. The resulting product was triturated with minimum hexane to obtain the desired product, 7-chloro-1-ethyl-6-fluoro-1,4-dihydro-4-oxoquinoline-3-carboxylic acid (0.65 g); Yield: 71.87%; $^1$H NMR(400 MHz, DMSO-d6): δ 14.79 (s, 1H), 9.08 (s, 1H), 8.45 (d, J=6.4, 1H), 8.22 (d, J=8.8, 1H), 4.60-4.65 (m, 2H), 1.38-1.42 (m, 3H).

Methods

Step 5

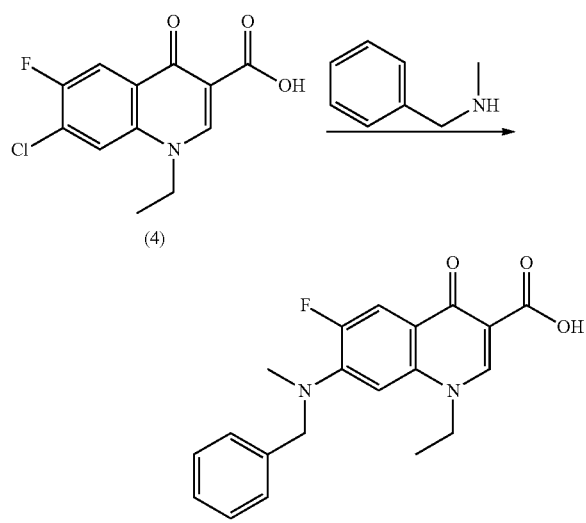

Procedure

In a 25 mL single neck flask, the intermediate 4 (0.5 g, 1.85 mmol) from Step 4, N-methyl(phenyl)methanamine (1.34 g, 11.11 mmol), CuI (0.04 g, 0.19 mmol) and 1-methylpyrrolidin-2-one (3 mL) were added and the resulting mixture was heated at 150° C. for 12 h and worked up. The reaction mixture was partitioned in dichloromethane/water and the organic layer was separated. The organic phase was dried over anhydrous $Na_2SO_4$, filtered and concentrated in vacuo. The residue was purified by prep-HPLC to obtain the pure 7-(N-benzyl-N-methylamino)-1-ethyl-6-fluoro-1,4-dihydro-4-oxoquinoline-3-carboxylic acid (23 mg); Yield: 5.48%; 1H NMR(400 MHz, CDCl$_3$): δ 15.24 (s, 1H), 8.59 (s, 1H), 8.05 (d, J=14, 1H), 7.26-7.38 (m, 5H), 6.61 (d, J=6.8, 1H), 4.64 (s, 2H), 4.16-4.18 (m, 2H), 3.15 (s, 3H), 1.38-1.41 (t, 3H); MS(ESI): 355.0(M+H); HPLC: 96.7%.

46

EXAMPLE 7

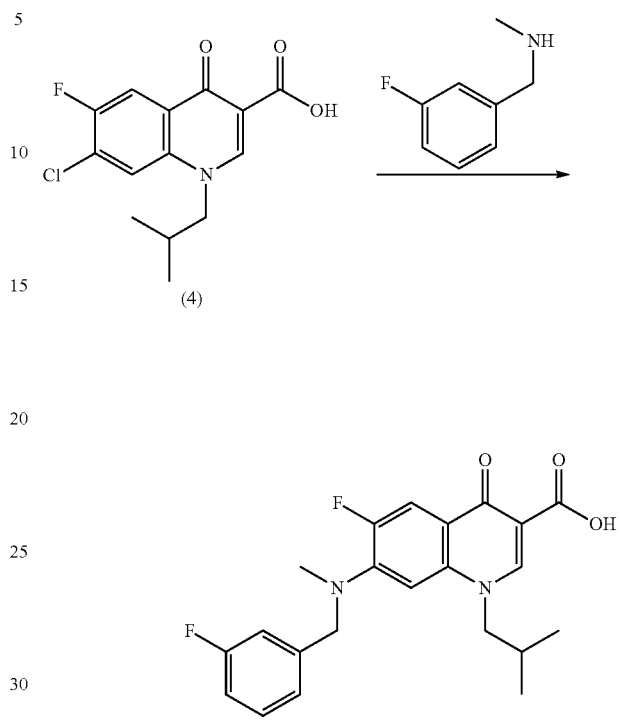

Procedure

In a 25 mL single neck flask, the intermediate 4 (0.55 g, 1.85 mmol) from Example 1, (3-fluorophenyl)-N-methylmethanamine (1.54 g, 11.11 mmol), CuI (0.04 g, 0.19 mmol) and 1-methylpyrrolidin-2-one (3 mL) were added and the resulting mixture was heated at 150° C. for 12 h and worked up. The reaction mixture was partitioned in dichloromethane/water and the organic layer was separated. The organic phase was dried over anhydrous $Na_2SO_4$, filtered and concentrated in vacuo. The residue was purified by prep-HPLC to obtain the pure 7-(N-(3-fluorobenzyl)-N-methylamino)-6-fluoro-1, 4-dihydro-1-isobutyl-4-oxoquinoline-3-carboxylic acid (25 mg); Yield: 3.38%; 1H NMR (400 MHz, CDCl3): δ 15.0 (s, 1H), 8.55 (s, 1H), 8.09 (d, J=14, 1H), 7.33-7.37 (m, 1H), 7.07-7.09 (m, 1H), 7.01-7.04 (m, 2H), 6.61 (d, J=7.2, 1H), 4.64 (s, 2H), 3.90-3.92 (m, 2H), 3.18-3.19 (m, 3H), 2.05-2.07 (m, 1H), 0.93-0.94 (m, 6H); MS(ESI): 401.0(M+H); HPLC: 95.2%.

Example 8

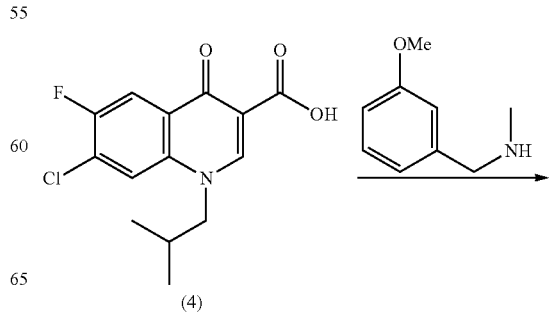

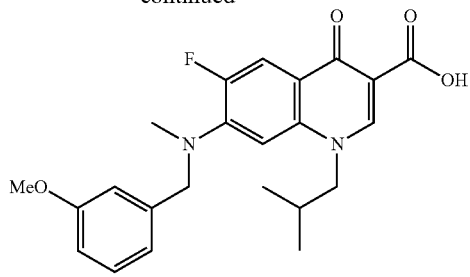

Procedure

In a 25 mL single neck flask, the intermediate 4 (0.55 g, 1.85 mmol) from Example 1, (3-methoxyphenyl)-N-methylmethanamine (1.67 g, 11.11 mmol), CuI (0.04 g, 0.19 mmol) and 1-methylpyrrolidin-2-one (3 mL) were added and the resulting mixture was heated at 150° C. for 12 h and worked up. The reaction mixture was partitioned in dichloromethane/water and the organic layer was separated. The organic phase was dried over anhydrous $Na_2SO_4$, filtered and concentrated in vacuo. The residue was purified by prep-HPLC to obtain the pure 7-(N-(3-methoxybenzyl)-N-methylamino)-6-fluoro-1,4-dihydro-1-isobutyl-4-oxoquinoline-3-carboxylic acid (25 mg); Yield: 3.29%; $^1$H NMR (400 MHz, $CDCl_3$): δ 8.52 (s,1H), 8.07 (d, J=14, 6H), 7.28-7.32 (t, 1H), 6.84-6.87 (t, 3H), 6.58 (d, J=7.2, 1H), 4.62 (s, 2H), 3.86 (d, J=7.6, 2H), 3.81(s, 3H), 3.22-3.23 (m, 3H), 1.99-2.06 (m, 1H), 0.89-0.91(m, 6H); MS(ESI): 413.0(M+H); HPLC: 96.5%.

EXAMPLE 9

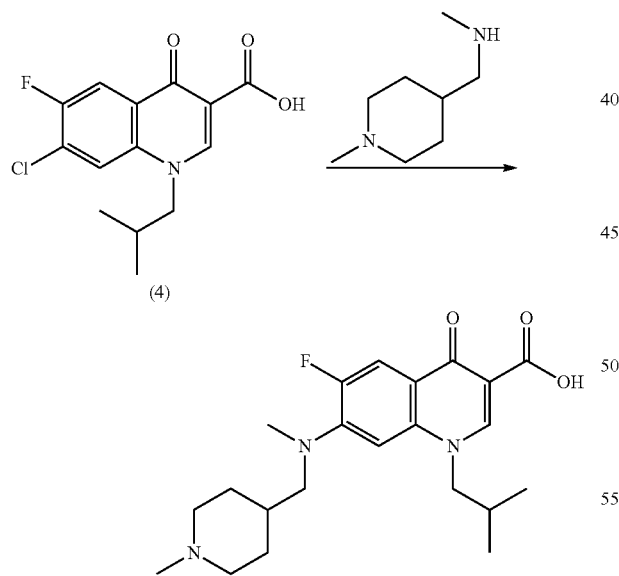

Procedure

In a 25 mL single neck flask, the intermediate 4 (0.45 g, 1.51 mmol) from Example 1, N-methyl(1-methylpiperidin-4-yl)methanamine (1.29 g, 9.06 mmol), CuI (0.03 g, 0.15 mmol) and 1-methylpyrrolidin-2-one (3 mL) were added and the resulting mixture was heated at 150° C. for 12 h and worked up. The reaction mixture was partitioned in dichloromethane/water and the organic layer was separated. The organic phase was dried over anhydrous $Na_2SO_4$, filtered and concentrated in vacuo. The residue was purified by prep-HPLC to obtain the pure 7-(N-methyl-N((1-methylpiperidin-4-yl) methyl) amino)-6-fluoro-1,4-dihydro-1-isobutyl-4-oxoquinoline-3-carboxylic acid (25 mg); Yield: 4.11%; $^1$H NMR (400 MHz, DMSO-d6): δ 9.02 (br s, 1H), 8.85 (s, 1H), 7.87 (d, J=14.4, 1H), 6.92 (d, J=7.6, 1H), 4.38-4.40 (m, 2H), 3.40-3.42 (m, 4H), 3.12 (s, 3H), 2.88-2.90 (m, 2H), 2.73 (s, 3H), 2.18-2.20 (m, 1H), 1.98 (s, 1H), 1.82-1.85 (m, 2H), 1.41-1.38 (m, 2H), 0.91-0.92 (m, 6H); MS(ESI): 404.0 (M+H); HPLC: 99.3%.

EXAMPLE 10

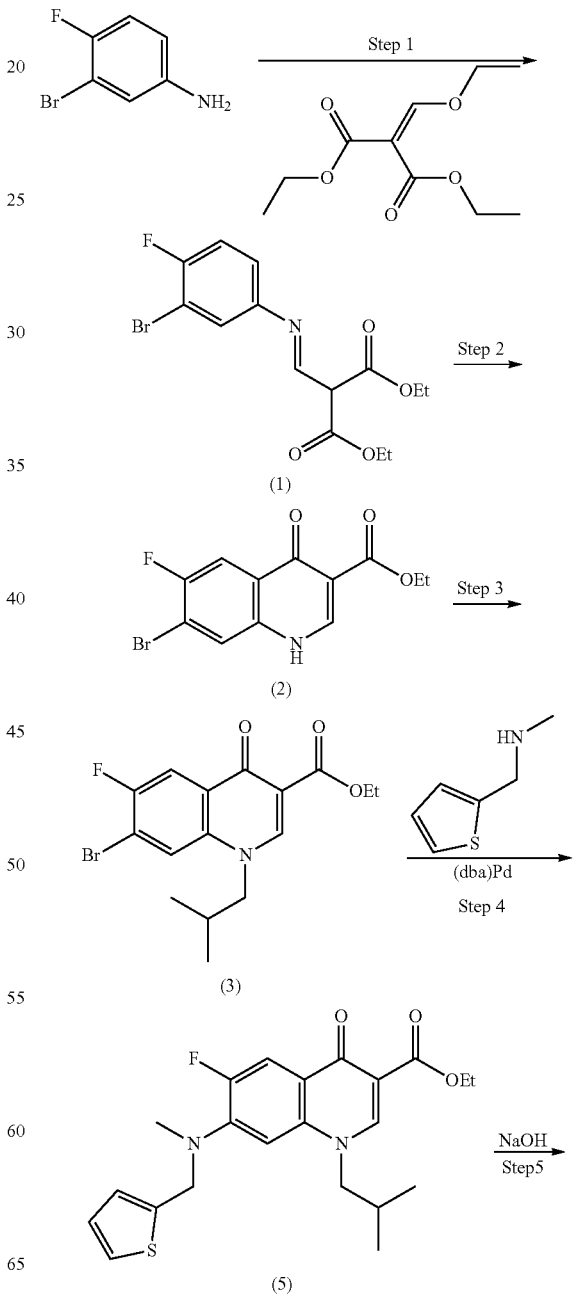

-continued

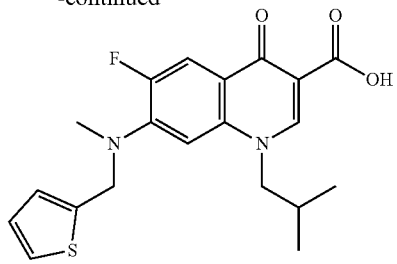

Step 1

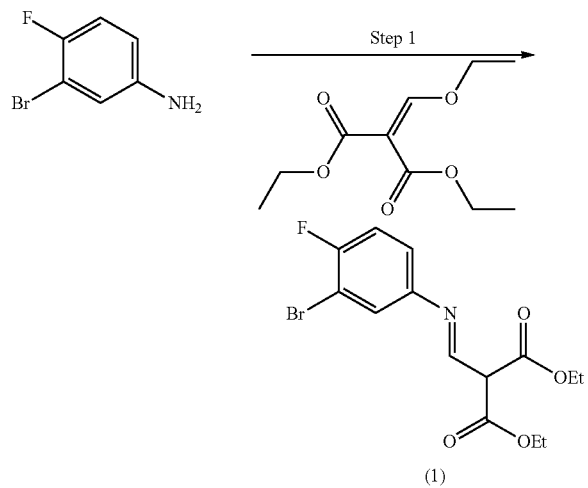

Procedure

A mixture of 3-chloro-4-fluoroaniline (20.8 g, 109.5 mmol) and diethyl ethoxymethylenemalonate (23.67 g, 109.5 mmol) was heated at 120-130° C. After 2 h, the resulting EtOH was evaporated off. The crude malonate was used in the successive reaction without further purification. The residue was recrystallized from n-hexane to obtain ethyl diethyl 2-((E)-(3-bromo-4-fluorophenylimino)methyl)malonate (35 g); Yield: 88.76%.

Step 2

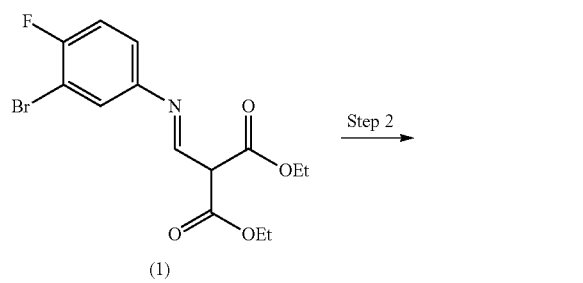

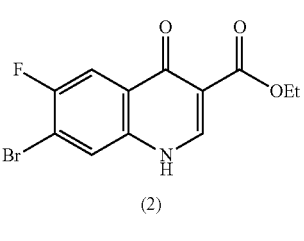

Procedure

In a 500 mL, 3-neck round-bottomed flask, the intermediate (1) (18 g, 49.975 mmol) and diphenyl ether (180 mL) were added and the resulting mixture was heated at 310° C. for 1 h. After the solution was cooled, the resulting precipitate was filtered off, washed with benzene, and dried. The solid was recrystallized from DMF to obtain the desired product, ethyl 7-bromo-6-fluoro-1,4-dihydro-4-oxoquinoline-3-carboxylate (9 g); Yield: 57.33%.

Step 3

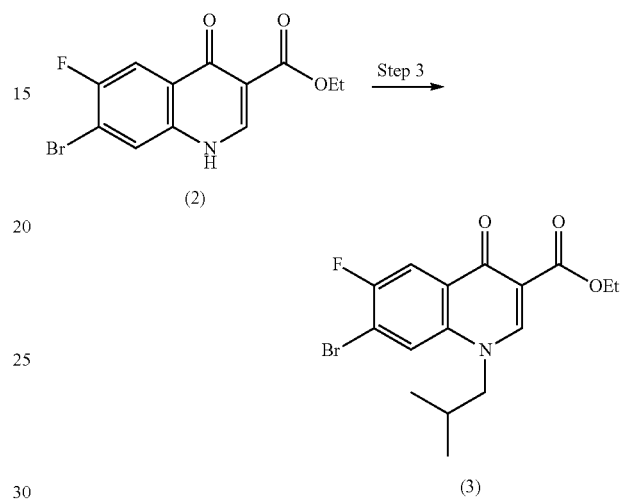

Procedure

In a closed system, ethyl 7-chloro-6-fluoro-1,4-dihydro-4-oxoquinoline-3-carboxylate (2) (5.0 g, 15.918 mmol) and $K_2CO_3$ (10.99 g, 79.59 mmol) were suspended in DMF (50 mL) and the reaction mixture was stirred for 15 min at room temperature. To this reaction mixture, 1-bromo-2-methylpropane (13.09 g, 95.508 mmol) and KI (0.26 g, 1.592 mmol) were added, and the reaction mixture was heated at 80° C. for 24 hrs. The reaction mixture was cooled and filtered. The filtrate was partitioned between ethyl acetate and brine solution, and the organic phase was separated, washed with brine solution, and dried over anhydrous $Na_2SO_4$ to obtain the crude product which was purified by column chromatography (Silica gel). The fractions containing desired compound were collected together and concentrated under reduced pressure to obtain ethyl 7-bromo-6-fluoro-1,4-dihydro-1-isobutyl-4-oxoquinoline-3-carboxylate (4.9 g); Yield: 83.17%; $^1$H-NMR (400 MHz, CDCl3): δ 8.39 (s, 1H), 8.22 (d, J=8.8, 1H), 7.64 (d, J=5.6, 1H), 4.37-4.43 (m, 2H), 3.93-3.96 (m, 2H), 2.23-2.28 (m, 1H), 1.39-1.43 (m, 3H), 1.00-1.04 (m, 6H).

Step 4

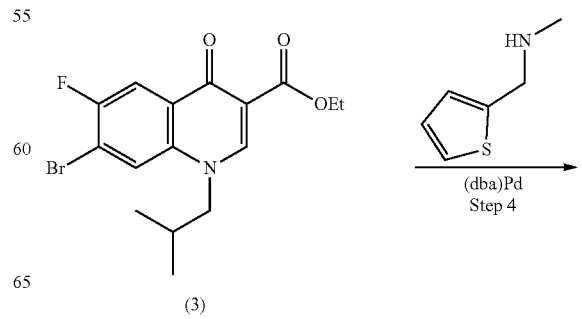

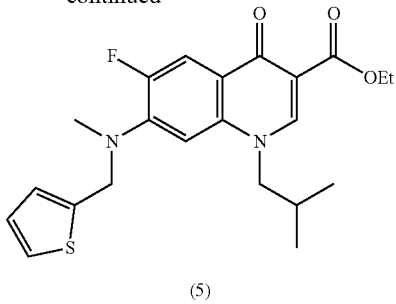

(5)

Procedure

In a 100 mL, 3-neck round-bottomed flask, the intermediate (3) (0.55 g, 1.486 mmol), N-methyl (thiophen-2-yl)methanamine (1.13 g, 8.916 mmol), (dba)Pd (0.06 g), K₂CO₃ (0.62 g, 4.458 mmol) and 1,4-dioxane (10mL) were added under N₂. The reaction mixture was stirred at 80° C. for 8 h and reaction completion was monitored by TLC. The mixture was added H₂O (500 mL) and extracted with EtOAc (500 mL×2). The combined organic layer was washed with brine and dried over anhydrous Na₂SO₄, concentrated in vacuo to afford a brown solid, which was then purified by silica gel column chromatography to obtain the desired product, ethyl 7-(N-methyl-N-((thiophen-2-yl)methyl)amino)-6-fluoro-1,4-dihydro-1-isobutyl-4-oxoquinoline-3-carboxylate (230 mg); Yield: 37.16%; MS (ESI): 417(M+H).

Step 5

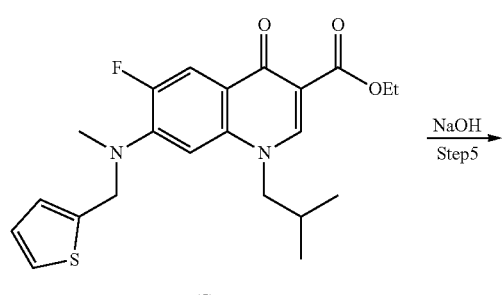

(5)

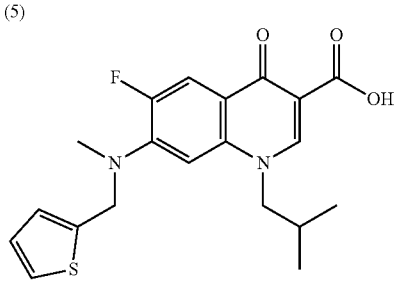

(5)

Procedure

In a 100 mL, 3-neck round-bottomed flask, the intermediate (5) (0.23 g, 0.552 mmol) was charged with THF: Water (2:1) (10 mL). To this reaction mixture, a 2M NaOH solution (4.4 mL) was added dropwise maintaining the temperature at 0° C. The reaction mixture was stirred at 80° C. for 2 h and the reaction completion was monitored by TLC. The mixture was cooled to 0° C. and acidified to pH 3-4 by 4N HCl. The solid obtained was filtered to obtain the crude product which was purified by silica gel column chromatography to provide 7-(N-methyl-N-((thiophen-2-yl)methyl) amino)-6-fluoro-1, 4-dihydro-1-isobutyl-4-oxoquinoline-3-carboxylic acid (25 mg); Yield: 8.25%; ¹HNNIR (400 MHz, DMSO-d6): δ 9.03 (s, 1H), 8.21 (d, J=6.4, 1H), 8.14-8.17 (m, 2H), 7.84 (d, J=3.6, 2H), 7.21 (d, J=3.2, 1H), 4.55-4.56 (m, 2H), 4.02 (s, 2H), 2.39 (s, 3H), 2.12-2.18 (m, 1H), 0.94 (m, 6H); MS(ESI): 389.0(M+H); HPLC: 96.9%.

EXAMPLE 11

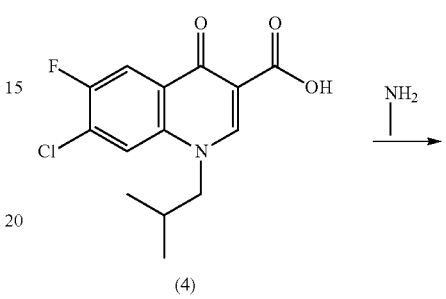

(4)

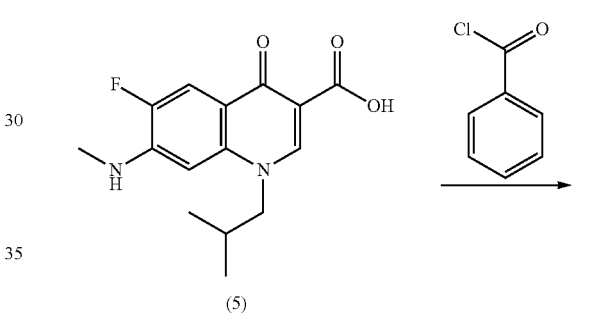

(5)

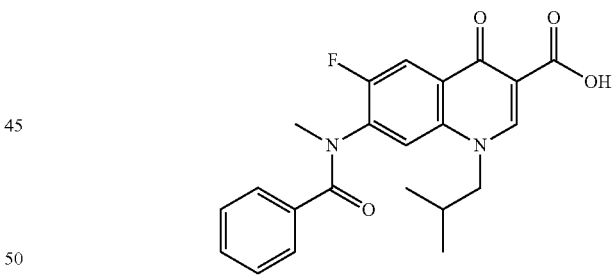

Step 1

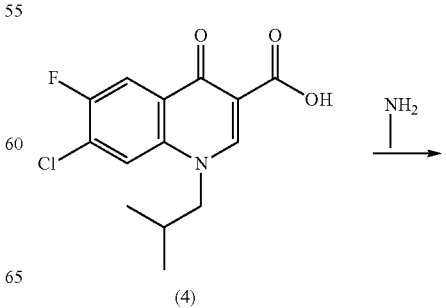

(4)

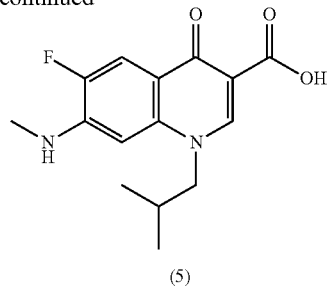

(5)

Procedure

In a 25 mL single neck flask, the intermediate 4 (1.36 g, 4.568 mmol) from Example 1, methanamine (0.85 g, 27.41 mmol), CuI (0.087 g, 0.46 mmol) and 1-methylpyrrolidin-2-one (5 mL) were added and the resulting mixture was heated at 150° C. for 12 h and worked up. The reaction mixture was partitioned in dichloromethane/water and the organic layer was separated. The organic phase was dried over anhydrous Na$_2$SO$_4$, filtered and concentrated in vacuo. The residue was purified by prep-HPLC to obtain the pure 6-fluoro-1,4-dihydro-1-isobutyl-7-(methylamino)-4-oxo-quinoline-3-carboxylic acid (70 mg); Yield: 5.25%; $^1$H NMR (400 MHz, CDCl3): δ 15.39 (s, 1H), 8.55 (s, 1H), 8.02 (d, J=11.6, 1H), 6.42-5.43 (t, 1H), 4.88-4.90 (t, 1H), 4.01-4.03 (m, 2H), 3.03-3.04 (m, 3H), 2.30-2.35 (m, 1H), 1.00-1.04 (m, 6H).

Step 2

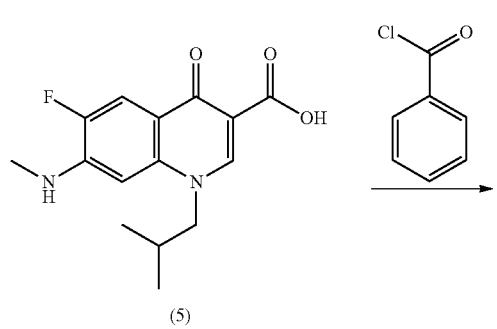

(5)

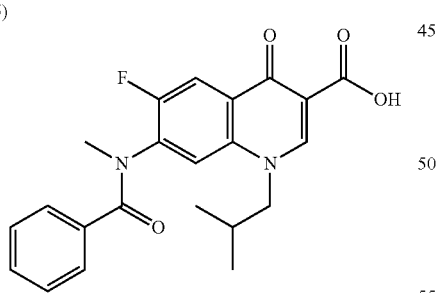

Procedure

In a 25 mL single neck flask, the intermediate 5 (93 mg, 0.32 mmol), benzoyl chloride (1.67 g, 11.11 mmol), toluene (10 mL) were added and the resulting mixture was heated at 120° C. for 12 h and worked up. The reaction mixture was partitioned in dichloromethane/water and the organic layer was separated. The organic phase was dried over anhydrous Na$_2$SO$_4$, filtered and concentrated in vacuo. The residue was purified by prep-HPLC to obtain the pure 7-(N-methylbenzamido)-6-fluoro-1,4-dihydro-1-isobutyl-4-oxoquinoline-3-carboxylic acid (25 mg); Yield: 19.73%; $^1$H NMR (400 MHz, DMSO-d6): δ 15.0 (s, 1H), 8.66 (s, 1H), 8.26 (d, J=8.0, 2H), 7.32 (s, 3H), 7.24-7.27 (m, 2H), 7.13 (s, 1H), 3.86 (s, 2H), 3.55 (s, 3H), 1.26 (s, 1H), 0.75-0.76 (m, 6H); MS(ESI): 397.0(M+H); HPLC: 95.2%.

EXAMPLE 12

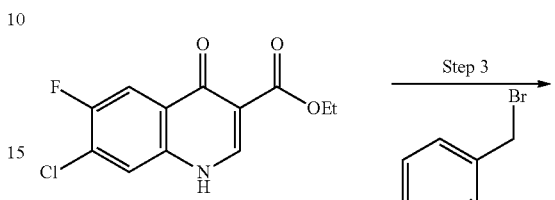

(2)

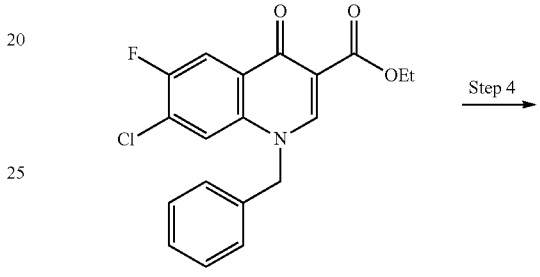

(3)

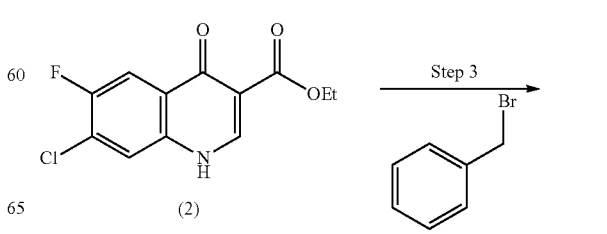

(2)

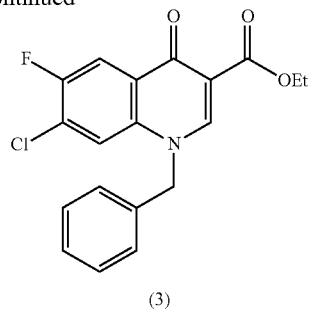

(3)

Procedure

In a closed system, ethyl 7-chloro-6-fluoro-1,4-dihydro-4-oxoquinoline-3-carboxylate (2) (1.5 g, 5.562 mmol) and K₂CO₃ (3.843 g, 27.809 mmol) were suspended in DMF (15 mL) and the reaction mixture was stirred for 15 min at room temperature. To this reaction mixture, 1-(bromomethyl) benzene (5.707 g, 33.37 mmol) and KI (0.092 g, 0.556 mmol) were added, and the reaction mixture was heated at 80° C. for 24 h. The reaction mixture was then cooled and filtered. The filtrate was partitioned between ethyl acetate and brine solution, and the organic phase was separated, washed with brine solution, and solvent was removed under reduced pressure to obtain the crude product which was purified by column chromatography (Silica gel).. The fractions containing desired compound were collected together and concentrated in vacuo to obtain ethyl 1-benzyl-7-chloro-6-fluoro-1,4-dihydro-4-oxoquinoline-3-carboxylate (1.1 g); Yield: 54.94%.

Step 4

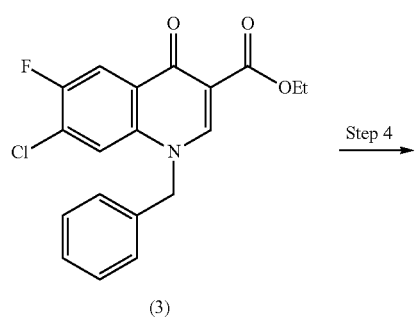

(3)

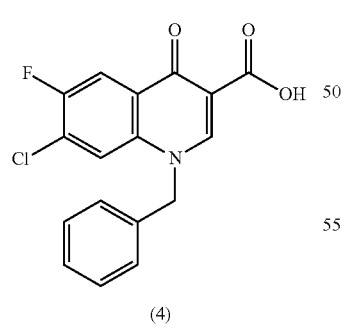

(4)

Procedure

In a 100 mL, 3-neck round-bottomed flask, the intermediate (3) (1.1 g, 3.06 mmol) was charged with THF: Water (2:1) (8 mL). To this reaction mixture, a 2M NaOH solution (6.12 mL) was added dropwise maintaining the temperature at 0° C. The reaction mixture was stirred at 80° C. for 2 h, cooled to 0° C. and acidified to pH 3-4 by 4N HCl. The solid obtained was filtered to obtain the crude product, 1-benzyl-7-chloro-6-fluoro-1,4-dihydro-4-oxoquinoline-3-carboxylic acid (0.9 g); Yield: 88.86%; ¹H NMR (400 MHz, DMSO_d6): δ 14.68 (s, 1H), 9.27 (d, J=3.2, 1H), 8.21-8.24 (t, 1H), 7.27-7.40 (m, 5H), 5.88-5.90 (m, 2H).

Step 5

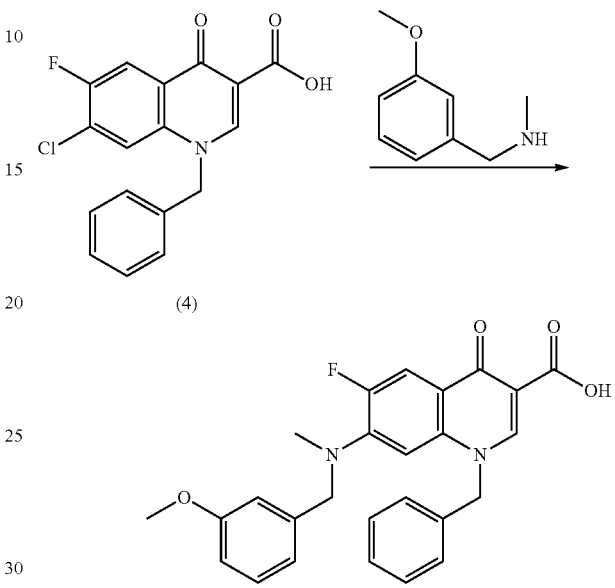

In a 25 mL single neck flask, the intermediate 4 (0.4 g, 1.21 mmol), (3-methoxyphenyl)-N-methylmethanamine (1.09 g, 7.23 mmol), CuI (0.023 g, 0.12 mmol) and 1-methylpyrrolidin-2-one (3 mL) were added and the resulting mixture was heated at 150° C. for 12 h and worked up. The reaction mixture was partitioned in dichloromethane/water and the organic layer was separated. The organic phase was dried over anhydrous Na₂SO₄, filtered and concentrated in vacuo. The residue was purified by prep-HPLC to obtain the pure 7-(N-(3-methoxybenzyl)-N-methylamino)-1-benzyl-6-fluoro-1, 4-dihydro-4-oxoquinoline-3-carboxylic acid (25 mg); Yield: 4.63%; ¹H NMR (400 MHz, CDCl₃): δ 15.0 (s, 1H), 8.77 (s, 1H), 8.01 (d, J=14, 1H), 7.33 (s, 3H), 7.22-7.26 (t, 1H), 7.04 (d, J=18.4, 2H), 6.82 (d, J=7.2, 1H), 6.70-6.74 (m, 2H), 6.52 (d, J=5.6, 1H), 5.30 (s, 2H), 4.43 (s, 2H), 3.71-7.76 (m, 3H), 2.92(s, 3H); MS(ESI): 447.0(M+H); HPLC: 98.0%.

EXAMPLE 13

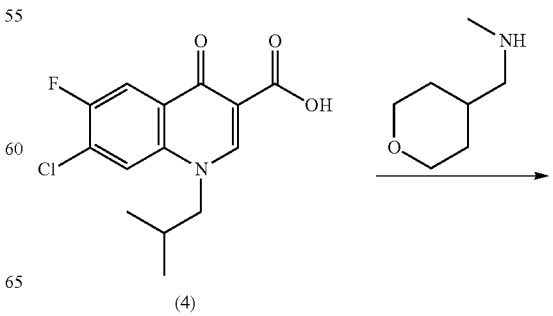

(4)

-continued

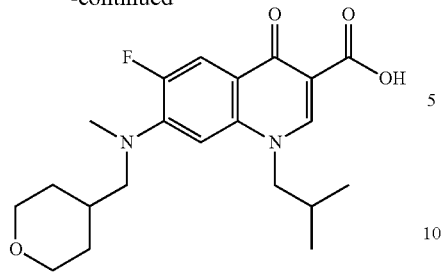

Procedure

In a 25 mL single neck flask, the intermediate 4 (0.45 g, 1.51 mmol) from Example 1, (tetrahydro-2H-pyran-4-yl)-N-methylmethanamine (1.17 g, 9.06 mmol), CuI (0.03 g, 0.15 mmol) and 1-methylpyrrolidin-2-one (3 mL) were added and the resulting mixture was heated at 150° C. for 12 h and worked up. The reaction mixture was partitioned in dichloromethane/water, and the organic layer was separated. The organic phase was dried over anhydrous $Na_2SO_4$, filtered and concentrated in vacuo. The residue was purified by prep-HPLC to obtain the pure 7-(N-((tetrahydro-2H-pyran-4-yl) methyl)-N-methylamino)-6-fluoro-1,4-dihydro-1-isobutyl-4-oxoquinoline-3-carboxylic acid (28 mg); Yield: 4.74%; $^1$H NMR (400 MHz, $CDCl_3$): δ 15.0 (s, 1H), 8.54 (s, 1H), 7.01 (d, J=14.4, 1H), 6.59 (d, J=7.2, 1H), 3.97-4.01 (m, 4H), 3.34-3.41 (m, 4H), 3.13 (s, 3H), 2.27-2.30 (m, 1H), 2.01 (s, 1H), 1.59-1.62 (m, 2H), 1.35-1.43 (m, 2H), 1.03-1.04 (m, 6H); MS(ESI): 391.0(M+H); HPLC: 98.8%.

EXAMPLE 15

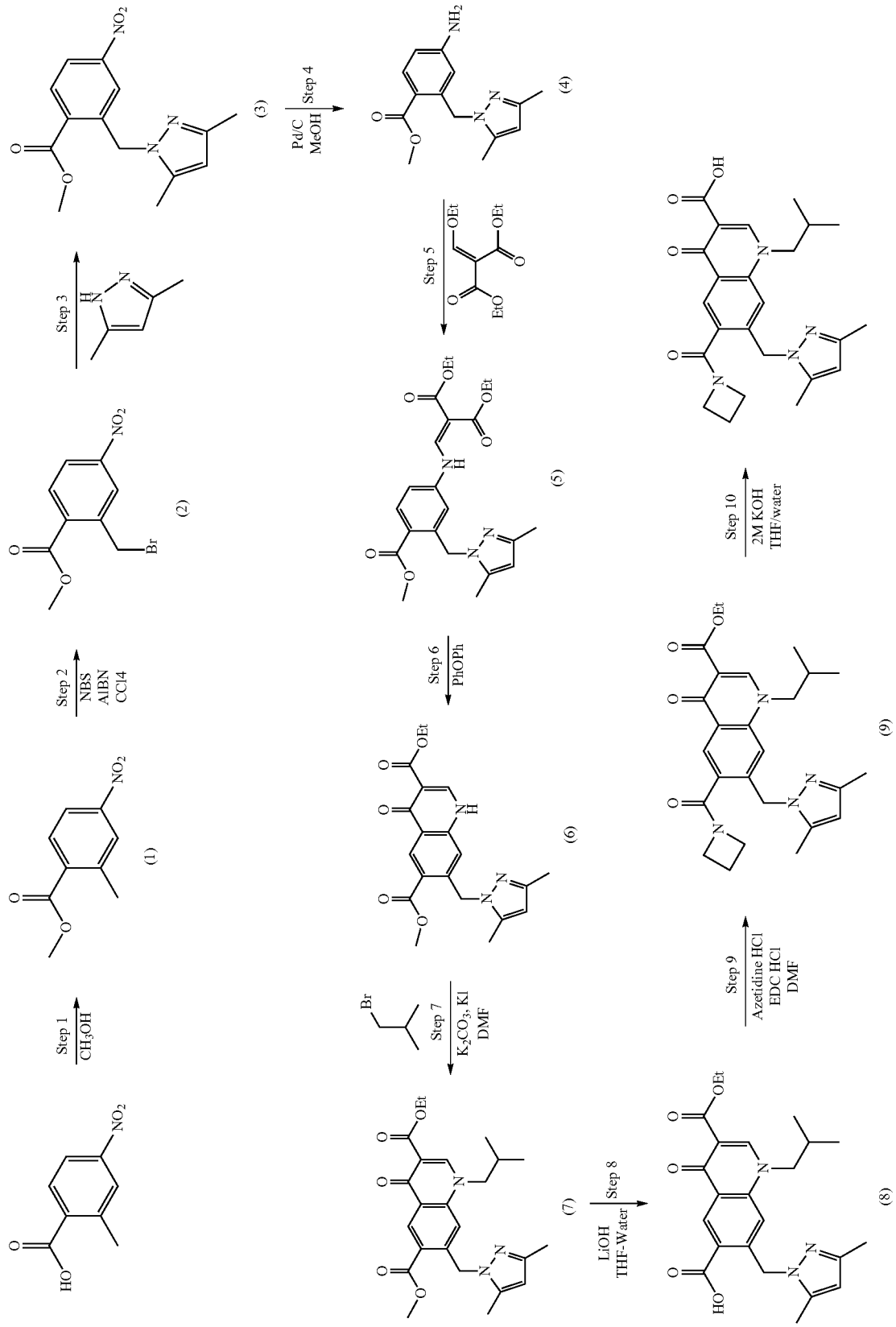

Step 1

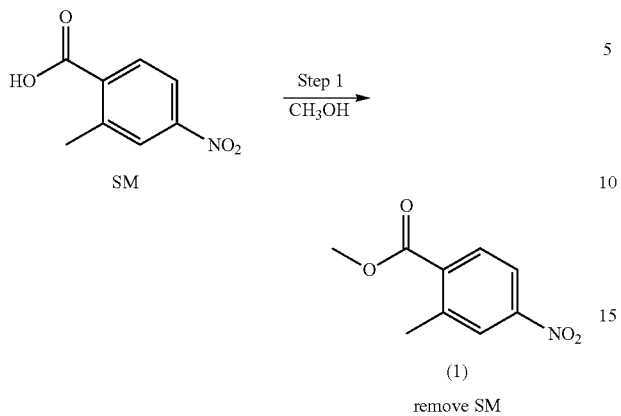

remove SM

Procedure

In a 250 mL, 3-neck round-bottomed flask, 2-methyl-4-nitrobenzoic acid (20 g, 93.8 mmol) was charged with methanol (100 mL) and sulfuric acid (4 mL). The reaction mixture was refluxed for 15 h. After completion, the reaction mixture was concentrated to obtain the crude product which was added water (200 mL) and basified to pH 7-8 with aqueous $NaHCO_3$ solution. Aqueous solution was extracted with dichloromethane (250 mL×3), the organic layer was washed with saturated brine solution followed by drying over anhydrous sodium sulphate. The solvent was removed to obtain methyl 2-methyl-4-nitrobenzoate (1), 20 g; Yield: 94.65%.

Step 2

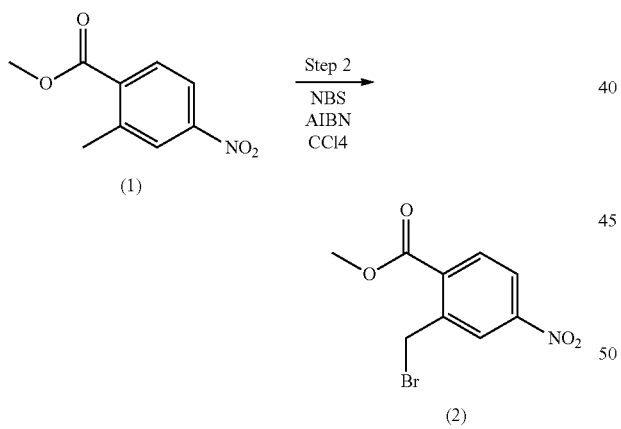

Procedure

In a 500 mL, 3-neck round-bottomed flask, the intermediate (1) (20 g, 88.01 mmol) was charged with $CCl_4$ (100 mL). N-bromosuccinimide (39.16g, 220.03 mmol) and AIBN (2.16 g, 13.20 mmol) were added and the resulting mixture was refluxed for 20 h. The reaction mixture was quenched with water (500 mL), extracted with dichloromethane (200 mL×3), and the combined organic layer was washed with saturated brine solution followed by drying over anhydrous sodium sulphate. The organic layer was evaporated under reduced pressure and the crude product obtained was purified by silica gel column chromatography to obtain pure methyl 2-(bromomethyl)-4-nitrobenzoate (2), 19 g; Yield: 78.7%; $^1$H NMR (400 MHz, DMSO-$d_6$): δ 8.52 (s, 1H), 8.27-8.3(dd, 1H), 8.07-8.1(d, 1H), 5.1 (s, 2H), 3.94 (s, 1H).

Step 3

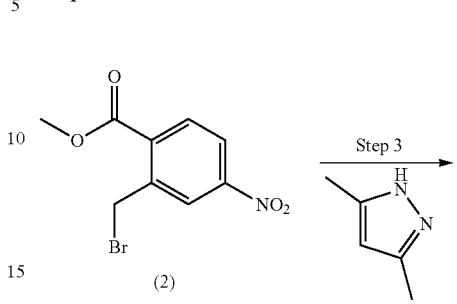

Procedure

In a 100 mL, 3-neck round-bottomed flask, 2,5-dimethyl-1H-pyrazole (5.26 g, 54.73 mmol) and $K_2CO_3$ (7.97 g, 54.73 mmol) were suspended in DMF (100 mL) and the reaction mixture was stirred for 15 min at room temperature. To this reaction mixture, the intermediate (2) (10 g, 36.48 mmol) was added and the resulting mixture was stirred at 60° C. for 6 h. The reaction mixture was cooled, filtered and the filtrate was evaporated under reduced pressure. The crude product was purified by silica gel column chromatography to obtain methyl 2-((3,5-dimethyl-1H-pyrazol-1-yl)methyl)-4-nitrobenzoate(3), 6 g; Yield: 56.78%; MS(ESI): 290.4(M+H).

Step 4

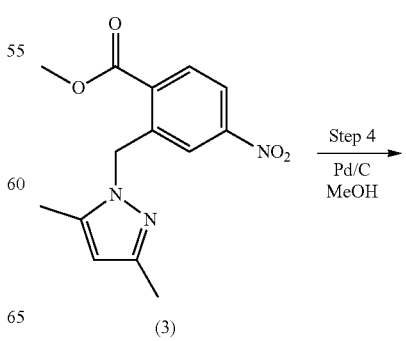

-continued

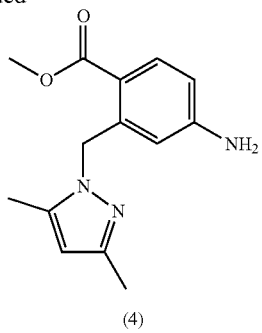

(4)

Procedure

The intermediate (3) (10 g, 20.74 mmol), palladium on carbon (5%) (1.2 g) and methanol (60 mL) were charged in a hydrogenator. The reaction mixture was stirred at 10 bar pressure of hydrogen pressure at room temperature for 6 h. After completion, reaction mixture was filtered through celite bed and filtrate was evaporated under reduced pressure. The crude product obtained was purified by triturating with hexanes to obtain methyl 4-amino-2-((3, 5-dimethyl-1H-pyrazol-1-yl) methyl)benzoate (4), 5 g; Yield: 93.17%; MS(ESI): 260.3(M+1).

Step 5

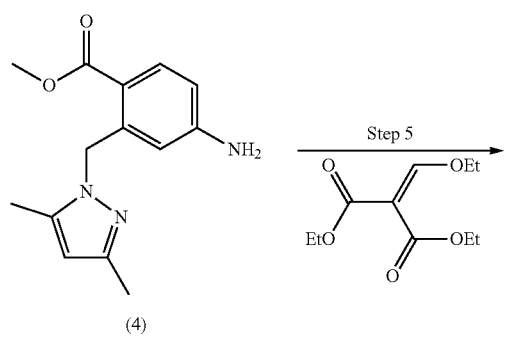

Procedure

In a 250 mL, 3-neck round-bottomed flask, the intermediate (4) (5 g, 19.28 mmol) was charged with toluene (100 mL) and diethyl-2-(ethoxymethylene) malonate (4.16 g, 19.28 mmol) was added at 25° C. The reaction mixture was refluxed for 1 h. The reaction mixture was then cooled to room temperature and hexane was added to precipitate the compound. The solid thus obtained was filtered to obtain diethyl-2-((3-((3,5-dimethyl-1H-pyrazol-1-yl)methyl)-4-(methoxycarbonyl)phenylamino) methylene)malonate (5), 5 g; Yield: 60.97%; MS(ESI): 430.1(M+1).

Step 6

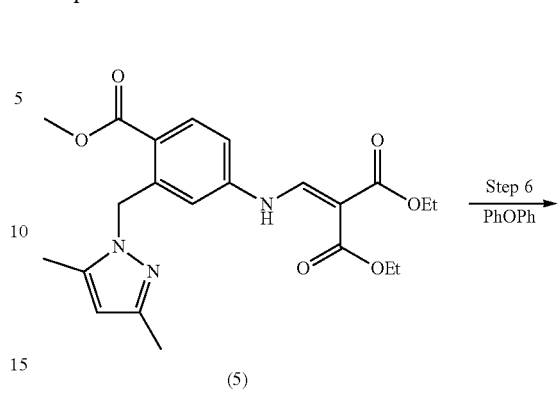

(5)

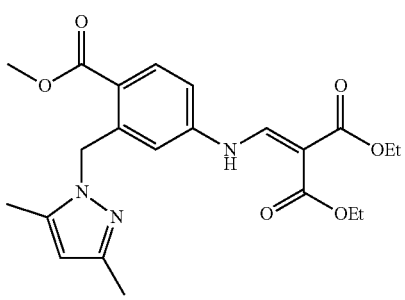

(6)

Procedure

In a 100 mL, 3-neck round-bottomed flask, diphenylether (200 mL) was heated upto 150° C. The intermediate (5) (5 g, 11.87 mmol) was added to the reaction mixture and stirred at that temperature for 4 h. The reaction mixture was then cooled to room temperature, and hexanes (300 mL) was added to precipitate the compound. The solid obtain was filtered to obtain 0.7 g of 3-ethyl 6-methyl 7-((3,5-dimethyl-1H-pyrazol-1-yl)methyl)-4-oxo-1,4-dihydroquinoline-3,6-dicarboxylate(6); Yield: 15.69%. The crude product contained traces of regioisomer formed during cyclization. This product was used for the next step without further purification.

Step 7

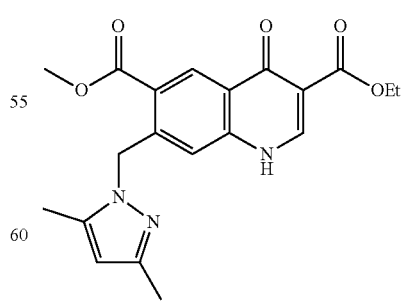

(6)

-continued

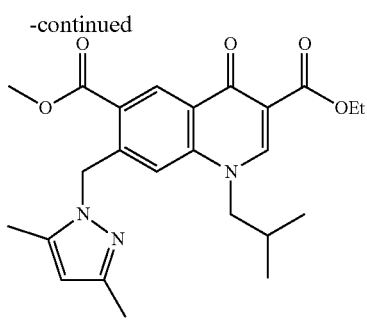

(7)

Procedure

In a 100 mL, 3-neck round-bottomed flask, the intermediate (6) (0.7 g, 1.82 mmol) and $K_2CO_3$ (1.2 g, 9.1 mmol) were suspended in DMF (10 mL), and the reaction mixture was stirred for 15 min at room temperature. To this reaction mixture, were added 1-bromo-2-methyl propane (1.5 g, 10.95 mmol) and KI (0.030 g, 0.18 mmol) and the resulting mixture was heated at 80° C. for 6 h. The reaction mixture was cooled and quenched with water, and was extracted with EtOAc. The organic layer was washed with brine and dried over anhydrous sodium sulphate. The solvent was evaporated under reduced pressure to obtain the crude compound which was purified by silica gel column chromatography to provide 3 -ethyl-6-methyl 7-((3,5-dimethyl-1H-pyrazol-1-yl)methyl)-1-isobutyl-4-oxo-1,4-dihydro-quinoline-3,6-dicarboxylate (7), 0.34 g; Yield: 42.5%; MS(ESI): 440.2(M+1). Step 8

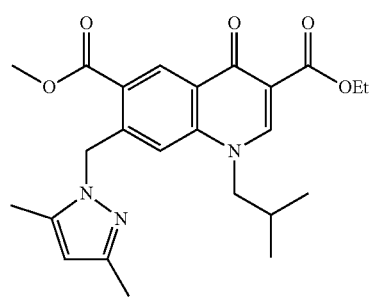

(7)

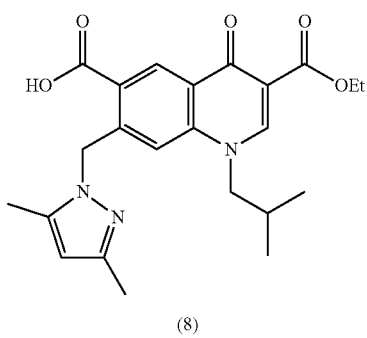

(8)

Procedure

In a 25 mL single neck round bottom flask, the intermediate (7) (0.3 g, 0.682 mmol) was charged with THF/Water (1:1) (5 mL) at 0° C. and LiOH (0.028 g, 0.681 mmol) was added to the the mixture. The resulting mixture was stirred at 0° C. for 30-50 min. The reaction was closely monitored for selective mono hydrolysis by mass spectroscopy and TLC. After completion, the mixture was acidified to pH 2 by 4 N HCl and the product was extracted with dichloromethane (50 mL×3). The combined organic layer was washed with saturated brine solution followed by drying over anhydrous sodium sulphate to obtain the crude product. The crude product was purified by silica gel column chromatographyto obtain 7-((3,5-dimethyl-1H-pyrazol-1-yl)methyl)-3-(ethoxycarbonyl)-1-isobutyl-4-oxo-1,4-dihydroquinoline-6-carboxylic acid (8), 0.2 g; Yield: 69.96%; MS(ESI): 425.8(M+H), 440.2(M+15).

Step 9

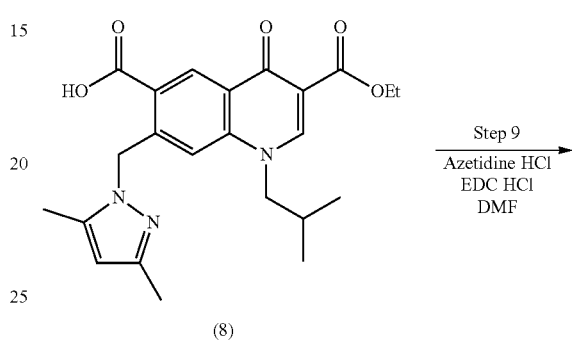

(8)

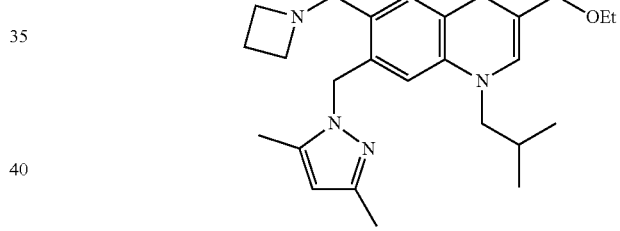

(9)

Procedure

In a 25 mL single neck round-bottomed flask, the intermediate (8) (0.2 g, 0.47 mmol) was charged with DMF (2 mL). To this reaction mixture, were added azetidine HCl (0.043 g, 0.47 mmol), EDC.HCl (0.094 g, 0.611 mmol) and DMAP (5 mg, 0.047 mmol) and the resulting mixture was stirred for 2 h at room temperature. After completion, the reaction was quenched with water and extracted with EtOAc (50 mL×3). The combined organic layer was washed with brine (20 mL) and dried over anhydrous sodium sulphate. The solvent was evaporated under reduced pressure to obtain the crude product which was purified by silica gel column chromatography to provide ethyl 6-(azetidine-1-carbonyl)-7-((3,5-dimethyl-1H-pyrazol-1-yl)methyl)-1-isobutyl-4-oxo-1,4-dihydroquinoline-3-carboxylate (9), 0.14 g; Yield: 58.33%; MS(ESI): 465.1(M+H).

Step 10

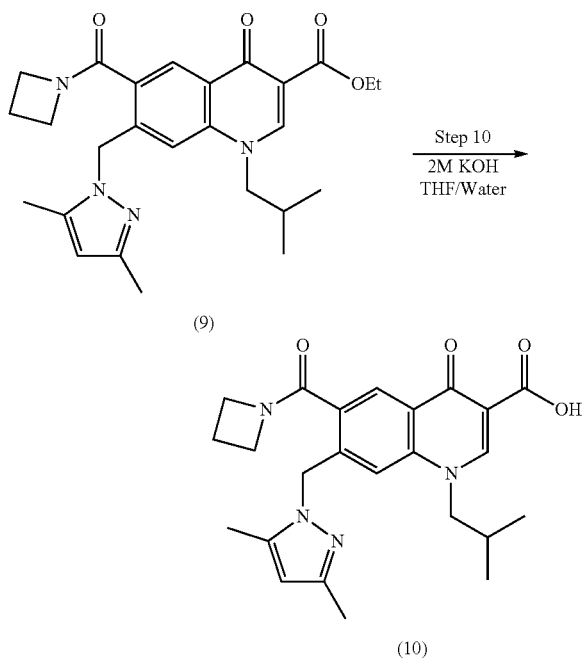

(9) → Step 10, 2M KOH, THF/Water → (10)

Procedure

In a 100 mL, 3-neck round-bottomed flask, the intermediate (9) (0.14 g) was added with THF: Water (1:1) (3 mL). To this reaction mixture, was added 2M KOH solution (1 mL) dropwise at 0° C. and the resulting mixture was stirred at room temperature for 2 h. The reaction mixture was cooled to 0° C. and acidified to pH 3-4 with 4 N HCl. The crude product was extracted with EtOAc (30 mL×3) and the combined organic layer was washed with brine solution, dried over anhydrous $Na_2SO_4$ and concentrated under reduced pressure to obtain the crude product. The crude product was purified by silica gel column chromatography to obtain 6-(azetidine-1-carbonyl)-7-((3,5-dimethyl-1H-pyrazol-1-yl)methyl)-1-isobutyl-4-oxo-1,4-dihydroquinoline-3-carboxylic acid (10), 40 mg; Yield: 30.7%.; $^1$H NMR (400 MHz, DMSO-$d_6$): δ 14.92 (s, 1H), 7.27-8.21 (m, 3H), 5.91 (s, 1H), 5.44 (s, 2H), 3.83-4.2 (m, 2H×3), 2.1-2.2 (m, 3H×2), 2.2 (m, 2H), 0.83-0.85 (d, 6H); MS(ESI): 437.3(M+H); HPLC: 97.24%.

EXAMPLE 16

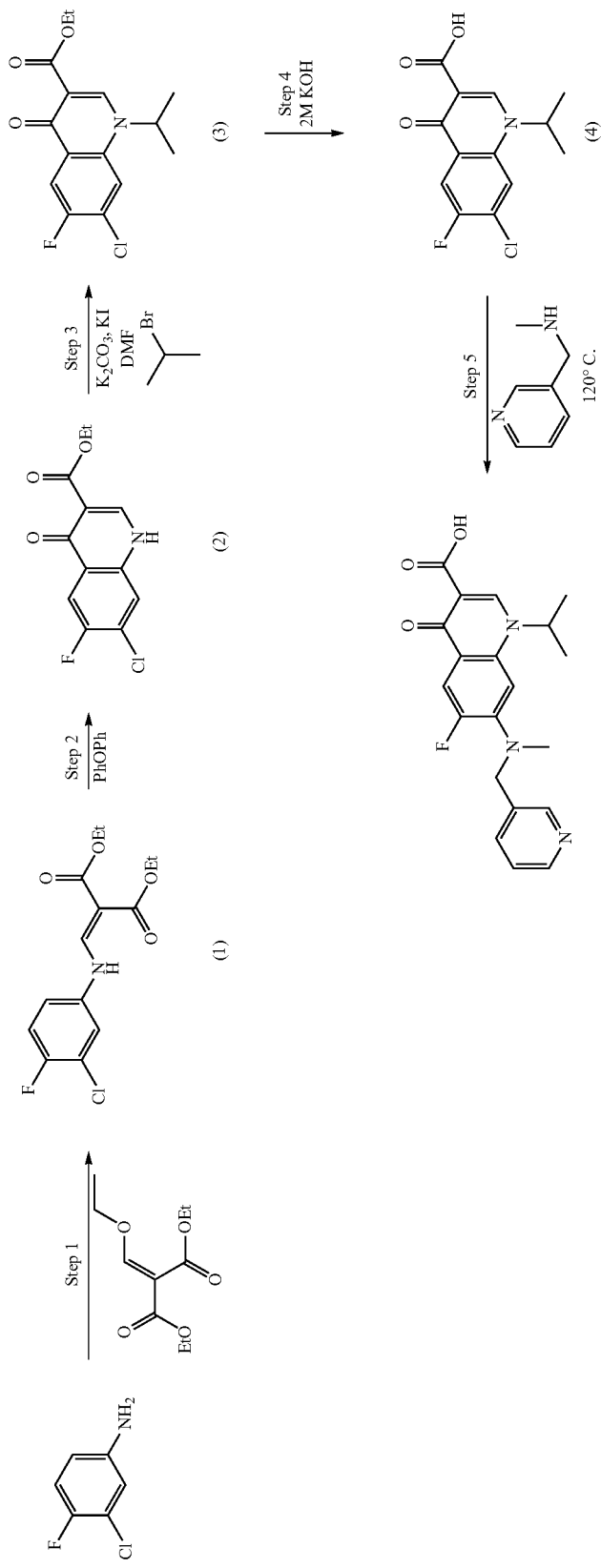

Step 3

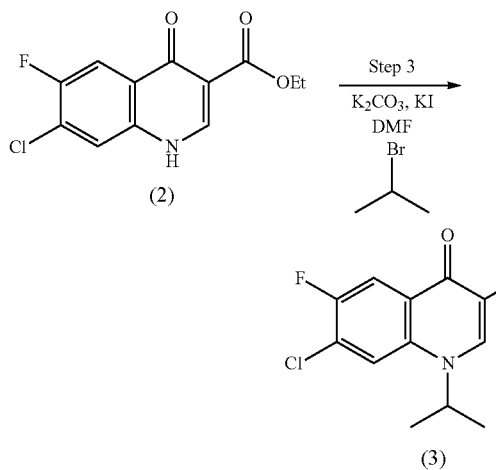

Procedure

In a closed system, ethyl-7-chloro-6-fluoro-4-oxo-1,4-dihydroquinoline-3-carboxylate (2) (2 g, 0.743 mmol) and K₂CO₃ (0.51 g, 3.715 mmol) were suspended in DMF (20 mL) and the reaction mixture was stirred for 15 min at room temperature. To this reaction mixture, isopropyl bromide (0.54 g, 4.46 mmol) and KI (0.012 g, 0.074 mmol) were added and the mixture was heated at 80° C. for 24 h. The reaction mixture was cooled and filtered. The obtained filtrate was partitioned between EtOAc and brine solution, and the organic phase was separated and washed with brine solution to obtain crude ethyl-7-chloro-6-fluoro-1-isopropyl-4-oxo-1,4-dihydroquinoline-3-carboxylate. The crude product was purified by column chromatography (Silica gel) and the solvent was removed in vacuo to obtain ethyl 7-chloro-6-fluoro-1-isopropyl-4-oxo-1,4-dihydroquinoline-3-carboxylate (3), 0.5g; Yield: 21.74%.

Step 4

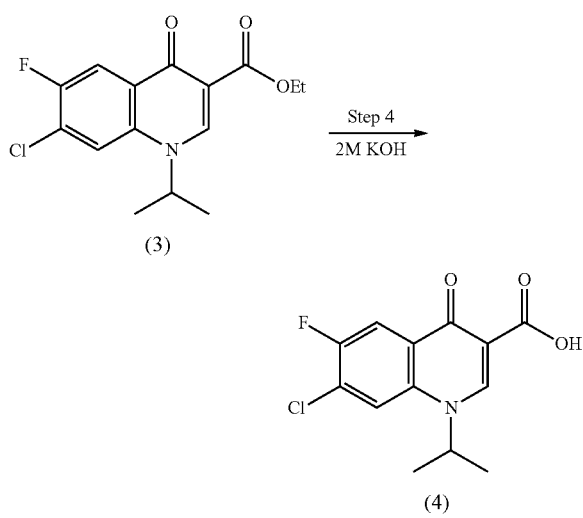

Procedure

In 100 mL, 3-neck round-bottomed flask, the intermediate (3) (0.4 g, 1.28 mmol) was charged with THF: Water (1:1) (5 mL). To this reaction mixture, 2 M KOH solutions (5 mL) was added dropwise maintaining temperature at 0° C. The resulting mixture was stirred at room temperature for 2 h, cooled to 0° C. and acidified to pH 3-4 by aqueous 4N HCl. The solid obtained was filtered to obtain the crude 7-chloro-6-fluoro-1-isopropyl-4-oxo-1,4-dihydroquinoline-3-carboxylic acid which was extracted with EtOAc (50 mL×3). The combined organic layer was washed with brine solution, dried over anhydrous Na₂SO₄ and concentrated in vacuo, triturated with minimum hexane to obtain 7-chloro-6-fluoro-1-isopropyl-4-oxo-1,4-dihydroquinoline-3-carboxylic acid (0.3 g); Yield: 83.33%.

Step 5

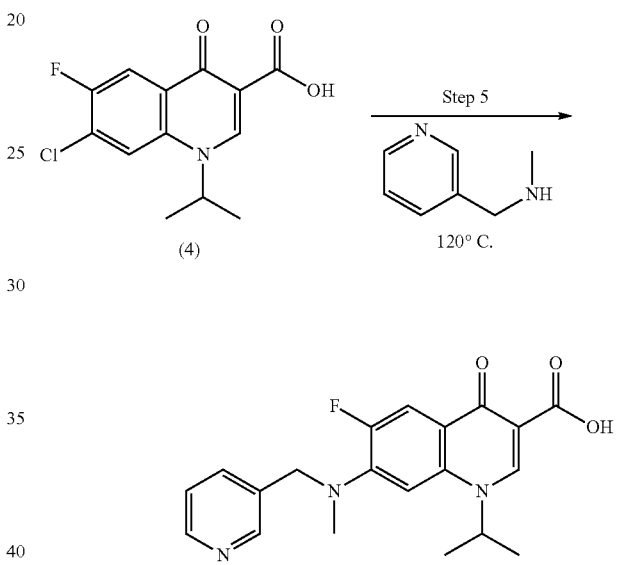

Procedure

In 25 mL single neck flask, the intermediate (4) (0.2 g, 0.70 mmol) and N-methyl-1-(pyridin-3-yl)methanamine (0.43 g, 3.42 mmol) were added, and the reaction mixture was heated at 120° C. for 24 h and worked up. The reaction mixture was partitioned in dichloromethane/water and the organic layer was separated. The organic layer was washed with 30% HCl solution, dried over anhydrous Na₂SO₄, and the solvent was removed in vacuo to obtain the crude product. The crude product was treated with EtOAc: hexane (50:50) (10 Vol) and heated at 60° C. for 15 min. Then the reaction was brought to room temperature, and the solid was filtered. The filtrate was concentrated to obtain crude solid which was triturated with ether to obtain the pure 6-fluoro-1-isopropyl-7-(methyl(pyridin-3-ylmethyl)amino)-4-oxo-1,4-dihydroquinoline-3-carboxylic acid (30 mg); Yield: 11.5%; ¹H NMR (400 MHz, DMSO-d6): δ 15.45 (s, 1H), 8.73 (s,1H), 7.14-8.55 (m, 6H), 5.18-5.22 (m, 1H), 4.72 (s, 2H), 3.12 (s, 3H), 1.48-1.56 (d, J=6.4, 6H); MS(ESI): 370(M+H); HPLC: 96.4%.

EXAMPLE 17

Step 5

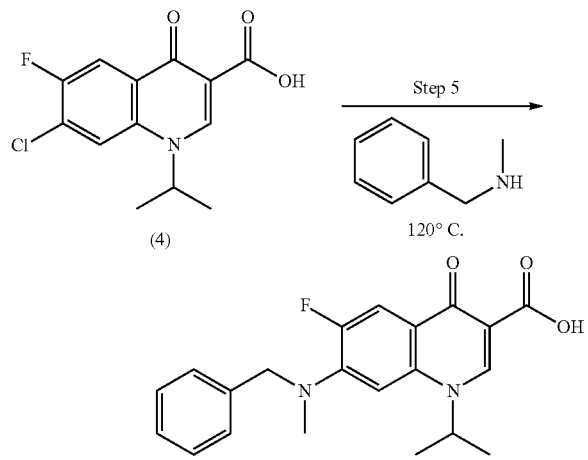

(4)

Procedure

In 25 mL single neck flask, the intermediate (4) (1.4 g, 4.94 mmol) from Example 16 and N-benzyl methylamine (2.9 g, 24.7 mmol) were added, and the reaction mixture was heated at 120° C. for 24 h and worked up. The reaction mixture was partitioned in dichloromethane/water and the organic layer was separated. The organic layer was washed with aqueous 4N HCl solution, dried over anhydrous $Na_2SO_4$, and the solvent was removed in vacuo to obtain the crude product. The crude product was treated with EtOAc:hexane (50:50) (10 Vol) and heated at 60° C. for 15 min. Then the reaction was brought to room temperature, and the solid was filtered. The filtrate was concentrated to obtain crude solid which was triturated with ether to obtain the pure 6-fluoro-1-isopropyl-7-(methyl(pyridin-3-ylmethyl)amino)-4-oxo-1,4-dihydroquinoline-3-carboxylic acid (20 mg); Yield: 1.1%; $^1$H NMR (400 MHz, DMSO-d6): δ 15.50 (s, 1H), 8.72 (s,1H), 7.10-7.93 (m, 6H), 5.16 (m, 1H), 4.69 (s, 2H), 3.12 (s, 3H), 1.46-1.48 (d, 6H); MS(ESI): 368.6(M+H); HPLC: 94.64%.

EXAMPLE 18

Step 5

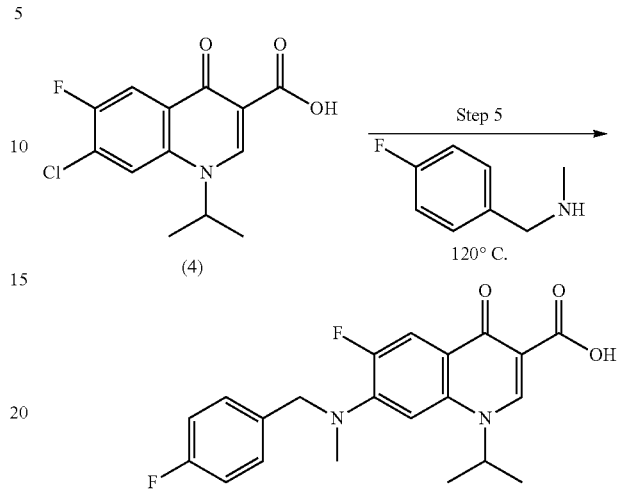

(4)

Procedure

In 25 mL single neck flask the intermediate 4 (1.4 g, 4.94 mmol) from Example 16 and 1-(4-fluorophenyl)-N-methyl-methanamine (3.4 g, 24.73 mmol) were added and heated at 120° C. for 24 h and worked up. The reaction mixture was partitioned in dichloromethane/water mixture and the organic layer was separated. The organic phase was washed with aqueous 4N HCl, dried over anhydrous $Na_2SO_4$, and the solvent was evapremoved in vacuo to obtain the crude product. The crude product was washed with hot EtOAc:Hexane (50:50) (10 Vol) and heated at 60° C. for 15 min. The solid obtained was washed with ether to obtain 0.2 g of pure 6-fluoro-7-((4-fluorobenzyl)(methyl)amino)-1-isopropyl-4-oxo-1,4-dihydroquinoline-3-carboxylic acid); Yield: 10.52%; $^1$-EINMR (400 MHz, DMSO-d6): δ 15.47 (s, 1H), 8.72 (s,1H), 7.93-7.10 (m, 6H), 5.19 (m, 1H), 4.66 (s, 2H), 3.10 (s, 3H), 1.49-1.47 (d, 6H), MS(ESI): 386.9(M+H); HPLC:98.48%.

TABLE 1

| Example | Structure | Name | Lactate Inhibition Cytotoxicity [EC50] |
|---|---|---|---|
| 1 | 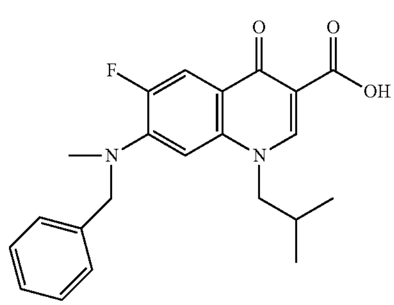 [SMILES: CC(C)Cn1cc(C(=O)O)c(=O)c2cc(F)c(N(C)Cc3ccccc3)cc21] | 7-(benzyl(methyl)amino)-6-fluoro-1-isobutyl-4-oxo-1,4-dihydroquinoline-3-carboxylic acid | A |

TABLE 1-continued

| Example | Structure | Name | Lactate Inhibition Cytotoxicity [EC50] |
|---|---|---|---|
| 3 | 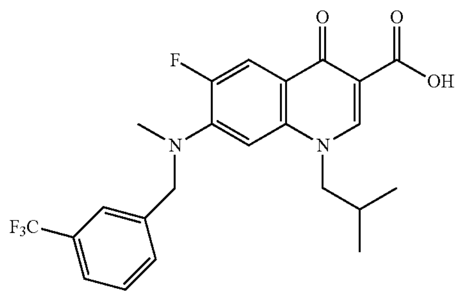 [SMILES: CC(C)Cn1cc(C(=O)O)c(=O)c2cc(F)c(N(C)Cc3cccc(C(F)(F)F)c3)cc21] | 6-fluoro-1-isobutyl-7-(methyl(3-(trifluoromethyl)benzyl)amino)-4-oxo-1,4-dihydroquinoline-3-carboxylic acid | A |
| 4 | 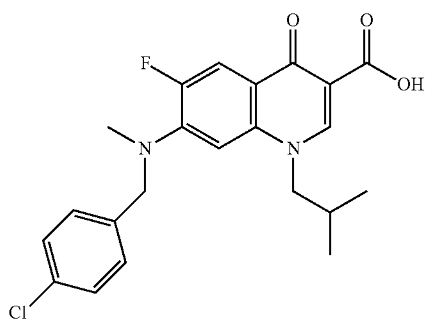 [SMILES: CC(C)Cn1cc(C(=O)O)c(=O)c2cc(F)c(N(C)Cc3ccc(Cl)cc3)cc21] | 7-((4-chlorobenzyl)(methyl)amino)-6-fluoro-1-isobutyl-4-oxo-1,4-dihydroquinoline-3-carboxylic acid | A |
| 5 | 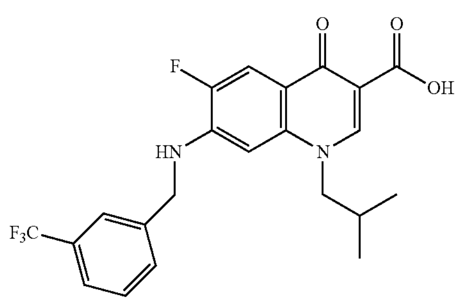 [SMILES: CC(C)Cn1cc(C(=O)O)c(=O)c2cc(F)c(NCc3cccc(C(F)(F)F)c3)cc21] | 6-fluoro-1-isobutyl-4-oxo-7-((3-(trifluoromethyl)benzyl)amino)-1,4-dihydroquinoline-3-carboxylic acid | A |
| 6 | 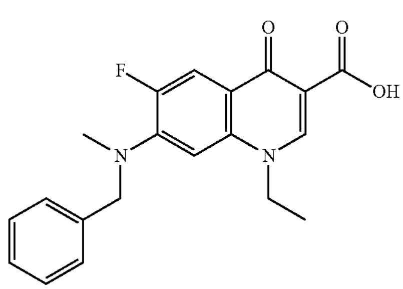 [SMILES: CCn1cc(C(=O)O)c(=O)c2cc(F)c(N(C)Cc3ccccc3)cc21] | 7-(benzyl(methyl)amino)-1-ethyl-6-fluoro-4-oxo-1,4-dihydroquinoline-3-carboxylic acid | A |
| 7 | 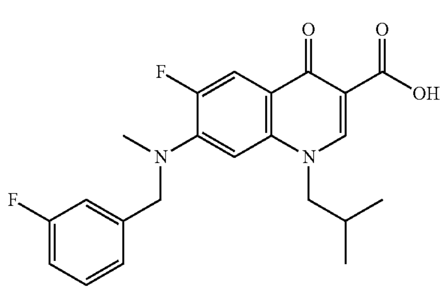 [SMILES: CC(C)Cn1cc(C(=O)O)c(=O)c2cc(F)c(N(C)Cc3cccc(F)c3)cc21] | 6-fluoro-7-((3-fluorobenzyl)(methyl)amino)-1-isobutyl-4-oxo-1,4-dihydroquinoline-3-carboxylic acid | A |

TABLE 1-continued

| Example | Structure | Name | Lactate Inhibition Cytotoxicity [EC50] |
|---|---|---|---|
| 8 | 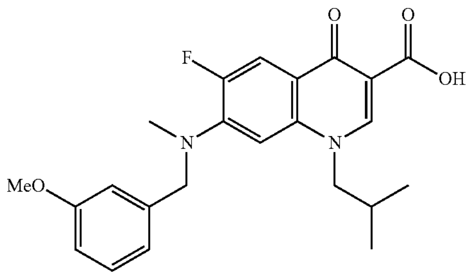 [SMILES: COc1cccc(CN(C)c2cc3c(cc2F)c(=O)c(C(=O)O)cn3CC(C)C)c1] | 6-fluoro-1-isobutyl-7-((3-methoxybenzyl)(methyl)amino)-4-oxo-1,4-dihydroquinoline-3-carboxylic acid | A |
| 9 | 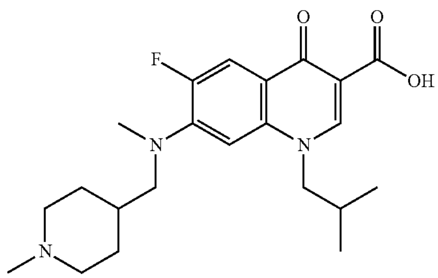 [SMILES: CC(C)Cn1cc(C(=O)O)c(=O)c2cc(F)c(N(C)CC3CCN(C)CC3)cc21] | 6-fluoro-1-isobutyl-7-(methyl((1-methyl-piperidin-4-yl)methyl)amino)-4-oxo-1,4-dihydroquinoline-3-carboxylic acid | A |
| 10 | 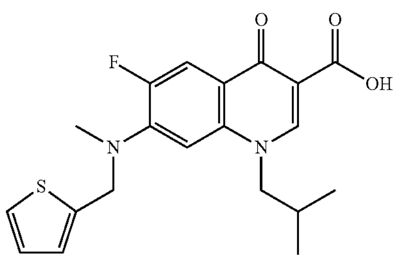 [SMILES: CC(C)Cn1cc(C(=O)O)c(=O)c2cc(F)c(N(C)Cc3cccs3)cc21] | 6-fluoro-1-isobutyl-7-(methyl(thiophen-2-ylmethyl)amino)-4-oxo-1,4-dihydro-quinoline-3-carboxylic acid | A |
| 11 | 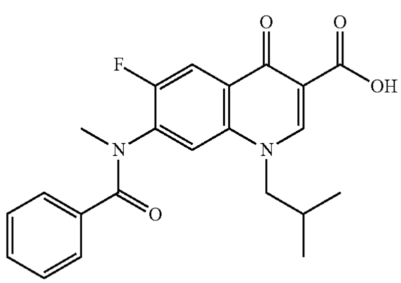 [SMILES: CC(C)Cn1cc(C(=O)O)c(=O)c2cc(F)c(N(C)C(=O)c3ccccc3)cc21] | 6-fluoro-1-isobutyl-7-(N-methylbenzamido)-4-oxo-1,4-dihydro-quinoline-3-carboxylic acid | A |
| 12 | 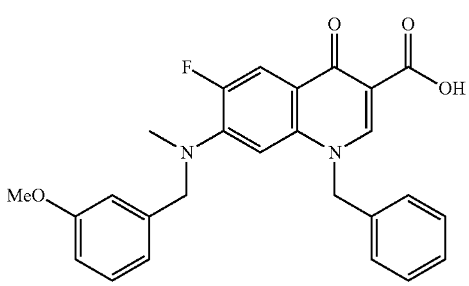 [SMILES: COc1cccc(CN(C)c2cc3c(cc2F)c(=O)c(C(=O)O)cn3Cc2ccccc2)c1] | 1-benzyl-6-fluoro-7-((3-methoxybenzyl)(methyl)amino)-4-oxo-1,4-dihydroquinoline-3-carboxylic acid | A |

TABLE 1-continued

| Example | Structure | Name | Lactate Inhibition Cytotoxicity [EC50] |
|---|---|---|---|
| 13 | 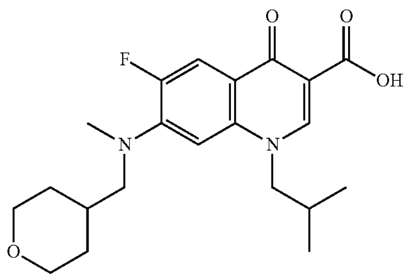 [SMILES: CC(C)Cn1cc(C(=O)O)c(=O)c2cc(F)c(N(C)CC3CCOCC3)cc21] | 6-fluoro-1-isobutyl-7-(methyl((tetrahydro-2H-pyran-4-yl)methyl)amino)-4-oxo-1,4-dihydroquinoline-3-carboxylic acid | NT |
| 15 | 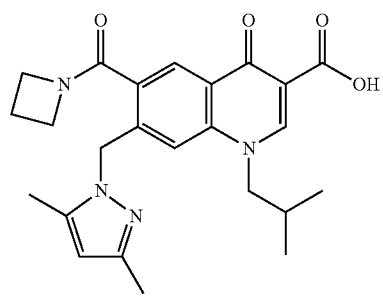 [SMILES: Cc1cc(C)n(Cc2cc3c(cc2C(=O)N2CCC2)c(=O)c(C(=O)O)cn3CC(C)C)n1] | 6-(azetidine-1-carbonyl)-7-((3,5-dimethyl-1H-pyrazol-1-yl)methyl)-1-isobutyl-4-oxo-1,4-dihydroquinoline-3-carboxylic acid | A |
| 16 | 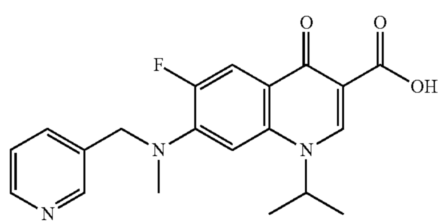 [SMILES: CC(C)n1cc(C(=O)O)c(=O)c2cc(F)c(N(C)Cc3cccnc3)cc21] | 6-fluoro-1-isopropyl-7-(methyl(pyridin-3-ylmethyl)amino)-4-oxo-1,4-dihydroquinoline-3-carboxylic acid | A |
| 17 | 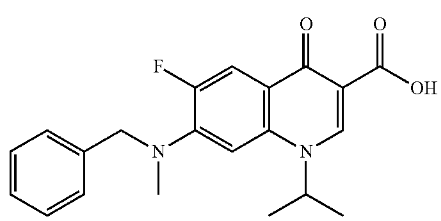 [SMILES: CC(C)n1cc(C(=O)O)c(=O)c2cc(F)c(N(C)Cc3ccccc3)cc21] | 7-(benzyl(methyl)amino)-6-fluoro-1-isopropyl-4-oxo-1,4-dihydroquinoline-3-carboxylic acid | A |
| 18 | 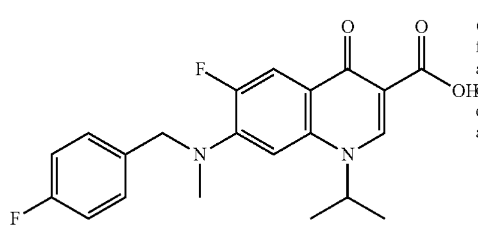 [SMILES: CC(C)n1cc(C(=O)O)c(=O)c2cc(F)c(N(C)Cc3ccc(F)cc3)cc21] | 6-fluoro-7-((4-fluorobenzyl)(methyl)amino)-1-isopropyl-4-oxo-1,4-dihydroquinoline-3-carboxylic acid | A |
| 19 | 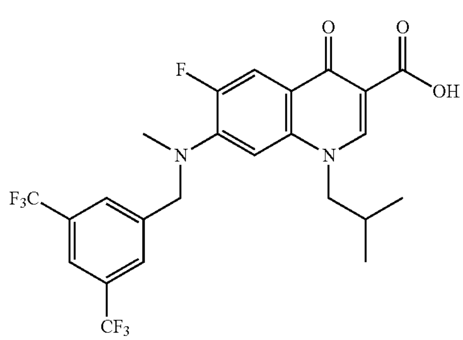 [SMILES: CC(C)Cn1cc(C(=O)O)c(=O)c2cc(F)c(N(C)Cc3cc(C(F)(F)F)cc(C(F)(F)F)c3)cc21] | bis(trifluoromethyl)benzyl)(methyl)amino)-6-fluoro-1-isobutyl-4-oxo-1,4-dihydroquinoline-3-carboxylic acid | NT |

TABLE 1-continued

| Example | Structure | Name | Lactate Inhibition Cytotoxicity [EC50] |
|---|---|---|---|
| 20 | 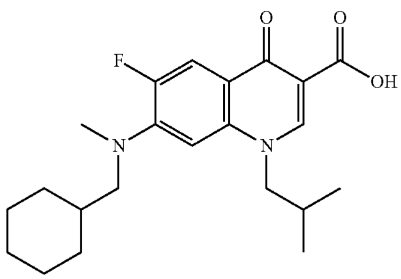 [SMILES: CC(C)Cn1cc(C(=O)O)c(=O)c2cc(F)c(N(C)CC3CCCCC3)cc21] | 7-((cyclohexylmethyl)(methyl)amino)-6-fluoro-1-isobutyl-4-oxo-1,4-dihydro-quinoline-3-carboxylic acid | NT |
| 21 | 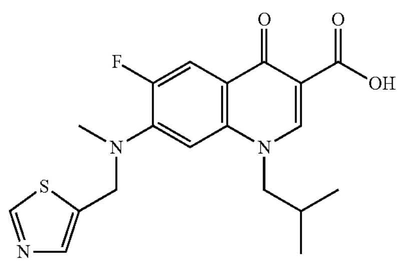 [SMILES: CC(C)Cn1cc(C(=O)O)c(=O)c2cc(F)c(N(C)Cc3cncs3)cc21] | 6-fluoro-1-isobutyl-7-(methyl(thiazol-5-ylmethyl)amino)-4-oxo-1,4-dihydro-quinoline-3-carboxylic acid | NT |
| 22 | 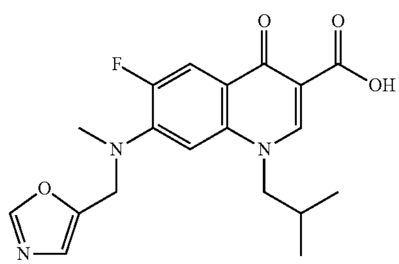 [SMILES: CC(C)Cn1cc(C(=O)O)c(=O)c2cc(F)c(N(C)Cc3cnco3)cc21] | 6-fluoro-1-isobutyl-7-(methyl(oxazol-5-ylmethyl)amino)-4-oxo-1,4-dihydro-quinoline-3-carboxylic acid | NT |
| 23 | 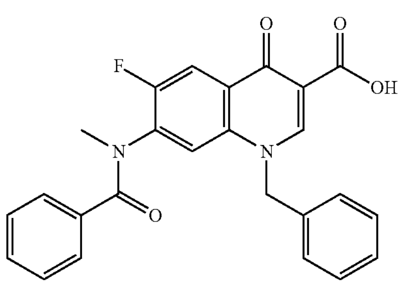 [SMILES: CN(C(=O)c1ccccc1)c1cc2c(cc1F)c(=O)c(C(=O)O)cn2Cc1ccccc1] | 1-benzyl-6-fluoro-7-(N-methylbenzamido)-4-oxo-1,4-dihydro-quinoline-3-carboxylic acid | NT |
| 24 | 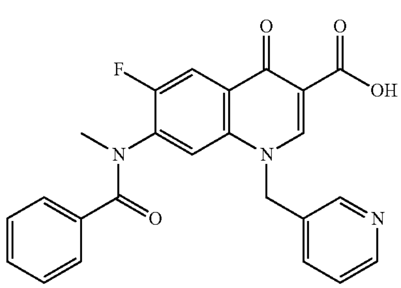 [SMILES: CN(C(=O)c1ccccc1)c1cc2c(cc1F)c(=O)c(C(=O)O)cn2Cc1cccnc1] | 6-fluoro-7-(N-methyl-benzamido)-4-oxo-1-(pyridin-3-ylmethyl)-1,4-dihydroquinoline-3-carboxylic acid | NT |

TABLE 1-continued

| Example | Structure | Name | Lactate Inhibition Cytotoxicity [EC50] |
|---|---|---|---|
| 25 | 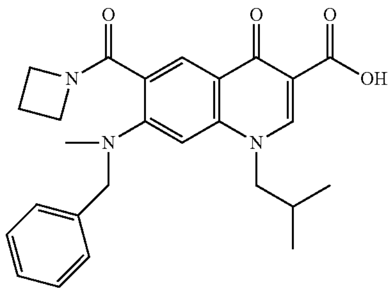 [SMILES: CC(C)Cn1cc(C(=O)O)c(=O)c2cc(C(=O)N3CCC3)c(N(C)Cc3ccccc3)cc21] | 6-(azetidine-1-carbonyl)-7-(benzyl(methyl)amino)-1-isobutyl-4-oxo-1,4-dihydroquinoline-3-carboxylic acid | NT |
| 26 | 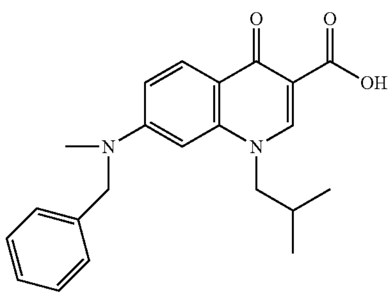 [SMILES: CC(C)Cn1cc(C(=O)O)c(=O)c2ccc(N(C)Cc3ccccc3)cc21] | 7-(benzyl(methyl)amino)-1-isobutyl-4-oxo-1,4-dihydroquinoline-3-carboxylic acid | NT |
| 27 | 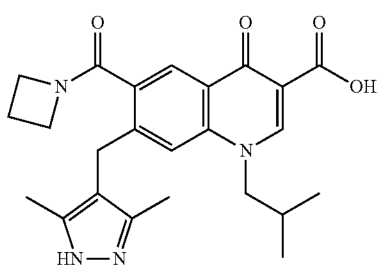 [SMILES: Cc1n[nH]c(C)c1Cc1cc2c(cc1C(=O)N1CCC1)c(=O)c(C(=O)O)cn2CC(C)C] | 6-(azetidine-1-carbonyl)-7-((3,5-dimethyl-1H-pyrazol-4-yl)methyl)-1-isobutyl-4-oxo-1,4-dihydroquinoline-3-carboxylic acid | NT |
| 28 | 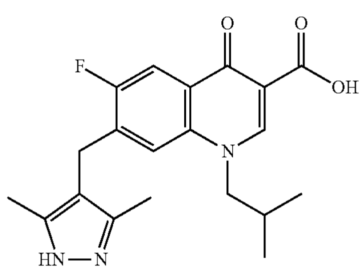 [SMILES: Cc1n[nH]c(C)c1Cc1cc2c(cc1F)c(=O)c(C(=O)O)cn2CC(C)C] | 7-((3,5-dimethyl-1H-pyrazol-4-yl)methyl)-6-fluoro-1-isobutyl-4-oxo-1,4-dihydroquinoline-3-carboxylic acid | NT |
| 29 | 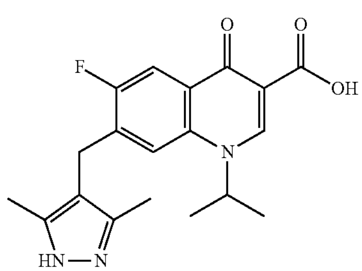 [SMILES: Cc1n[nH]c(C)c1Cc1cc2c(cc1F)c(=O)c(C(=O)O)cn2C(C)C] | 7-((3,5-dimethyl-1H-pyrazol-4-yl)methyl)-6-fluoro-1-isopropyl-4-oxo-1,4-dihydroquinoline-3-carboxylic acid | NT |

TABLE 1-continued

| Example | Structure | Name | Lactate Inhibition Cytotoxicity [EC50] |
|---|---|---|---|
| 30 | 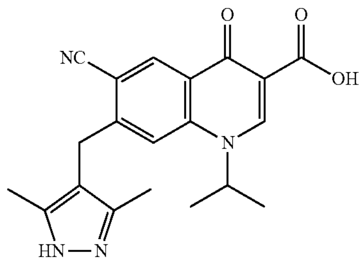 [SMILES: Cc1n[nH]c(C)c1Cc1cc2c(cc1C#N)c(=O)c(C(=O)O)cn2C(C)C] | 6-cyano-7-((3,5-dimethyl-1H-pyrazol-4-yl)methyl)-1-isopropyl-4-oxo-1,4-dihydroquinoline-3-carboxylic acid | NT |
| 31 | 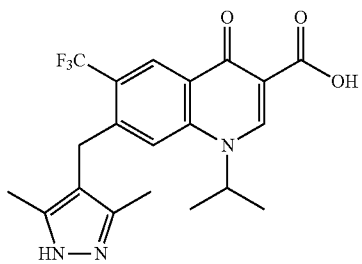 [SMILES: Cc1n[nH]c(C)c1Cc1cc2c(cc1C(F)(F)F)c(=O)c(C(=O)O)cn2C(C)C] | 7-((3,5-dimethyl-1H-pyrazol-4-yl)methyl)-1-isopropyl-4-oxo-6-(trifluoromethyl)-1,4-dihydroquinoline-3-carboxylic acid | NT |
| 32 | 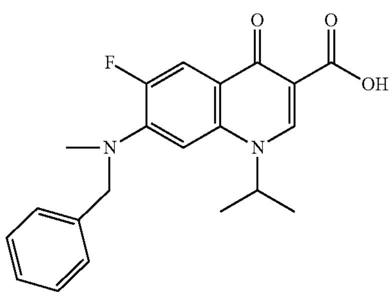 [SMILES: CC(C)n1cc(C(=O)O)c(=O)c2cc(F)c(N(C)Cc3ccccc3)cc21] | 7-(benzyl(methyl)amino)-6-fluoro-1-isopropyl-4-oxo-1,4-dihydro-quinoline-3-carboxylic acid | NT |
| 33 | 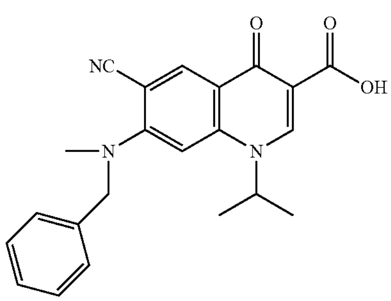 [SMILES: CC(C)n1cc(C(=O)O)c(=O)c2cc(C#N)c(N(C)Cc3ccccc3)cc21] | 7-(benzyl(methyl)amino)-6-cyano-1-isopropyl-4-oxo-1,4-dihydro-quinoline-3-carboxylic acid | NT |
| 34 | 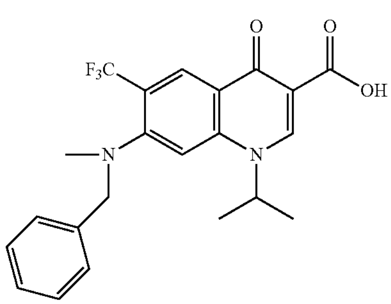 [SMILES: CC(C)n1cc(C(=O)O)c(=O)c2cc(C(F)(F)F)c(N(C)Cc3ccccc3)cc21] | 7-(benzyl(methyl)amino)-1-isopropyl-4-oxo-6-(trifluoromethyl)-1,4-dihydroquinoline-3-carboxylic acid | NT |

TABLE 1-continued

| Example | Structure | Name | Lactate Inhibition Cytotoxicity [EC50] |
|---|---|---|---|
| 35 | 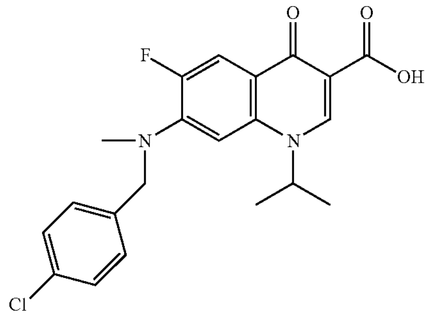 [SMILES: CC(C)n1cc(C(=O)O)c(=O)c2cc(F)c(N(C)Cc3ccc(Cl)cc3)cc21] | 7-((4-chlorobenzyl)(methyl)amino)-6-fluoro-1-isopropyl-4-oxo-1,4-dihydroquinoline-3-carboxylic acid | NT |
| 37 | 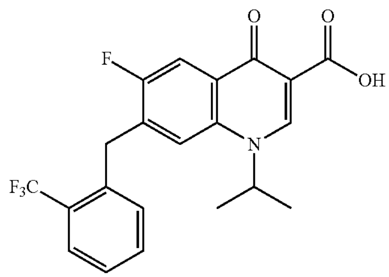 [SMILES: CC(C)n1cc(C(=O)O)c(=O)c2cc(F)c(Cc3ccccc3C(F)(F)F)cc21] | 6-fluoro-1-isopropyl-4-oxo-7-(2-(trifluoromethyl)benzyl)-1,4-dihydroquinoline-3-carboxylic acid | NT |
| 38 | 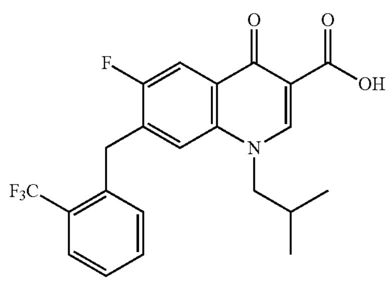 [SMILES: CC(C)Cn1cc(C(=O)O)c(=O)c2cc(F)c(Cc3ccccc3C(F)(F)F)cc21] | 6-fluoro-1-isobutyl-4-oxo-7-(2-(trifluoromethyl)benzyl)-1,4-dihydroquinoline-3-carboxylic acid | NT |
| 39 | 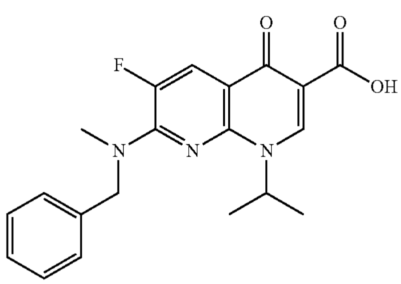 [SMILES: CC(C)n1cc(C(=O)O)c(=O)c2cc(F)c(N(C)Cc3ccccc3)nc21] | 7-(benzyl(methyl)amino)-6-fluoro-1-isopropyl-4-oxo-1,4-dihydro-1,8-naphthyridine-3-carboxylic acid | NT |
| 41 | 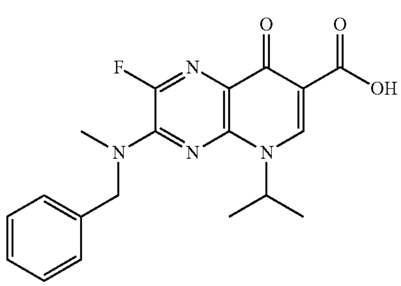 [SMILES: CC(C)n1cc(C(=O)O)c(=O)c2nc(F)c(N(C)Cc3ccccc3)nc21] | 3-(benzyl(methyl)amino)-2-fluoro-5-isopropyl-8-oxo-5,8-dihydropyrido[2,3-b]pyrazine-7-carboxylic acid | NT |

TABLE 1-continued

| Example | Structure | Name | Lactate Inhibition Cytotoxicity [EC50] |
|---|---|---|---|
| 43 | (structure) | 7-(benzyl(methyl)amino)-6-fluoro-1-isopropyl-4-oxo-1,4-dihydro-1,5-naphthyridine-3-carboxylic acid | NT |

A = <1 uM;
B = 1-10 uM;
C = >10 uM;
NT = Not Tested

TABLE II

| Example | Structure | Lactate Consumption (%)/[IC50][14C labeled] | Lactate Consumption [Lactate Kit] (%)/[IC50] |
|---|---|---|---|
| 1 | (structure) | A | 86% |

MTS or MTT Cell Proliferation Assay

Cytotoxicity of the inhibition of monocarboxylate transporters of the invention was determined and are shown in Table 1. The anti-proliferation effect of MCT inhibition was investigated across a panel of solid and haemotological tumor cell lines. Cells were routinely cultured in their appropriate growth medium. On day 1, between 5,000-10,000 cells/well were plated into 96-well plates. 100 μL of phosphate buffered saline solution was added to the external wells to prevent media evaporation. Plates were incubated overnight at 37° C. in the presence of 5% $CO_2$. On day 2, dry weight compound stocks were dissolved to a concentration of 20 mM in 100% DMSO. Compounds were further diluted in either growth medium or 10 mM lactate medium (For SiHa cell lines; Basic DMEM, 10% FBS, 10 mM Na-Lactate, 2.2 g/L $NaHCO_3$, no glutamine) to generate a final dose range of 10 nM to 100 μM. Plates were then incubated at at 37° C. in the presence of 5% $CO_2$ for a further 72 hours post-dosing. On day 5, 20 μL of CellTiter 96 AQ MTS reagent or MTT was added to each well and the plate was returned to the incubator for 2-4 hours. In case of lactate medium, the medium was replaced by 100 μL of growth medium and 20 μL of CellTiter 96 AQ MTS reagent or replaced the media in cells with 100 uL of growth media containing 10% MTT solution,. MTS or MTT is bioreduced by NADPH or NADH produced by dehydrogenase enzymes in metabolically active cells into a coloured formazan product that is soluble in tissue culture medium. The amount of coloured formazan product is directly proportional to the number of living cells in culture. In the case of MTT, after 4 hr incubation, the media was removed from the plates and the plate was air-dried. Then, 100 uL of DMSO was added to each well, and incubated for 30 mins at room temperature with mild shaking. The absorbance of the plates was read on a Synergy H4 plate reader using 490 nM or 540 nm measurement wavelength. Dose response curves were plotted and $IC_{50}$ values were calculated using Prism. The $IC_{50}$ value is equivalent to the concentration of compound that causes 50% inhibition of growth calculated from the compound treated signal to the vehicle treated signal.

Lactate Consumption Assay in Tumor Cell Lines.

The inhibition of monocarboxylate transporters of the invention was determined and data are shown in Table II. Cells are maintained in their appropriate growth medium (DMEM medium with 4.5 g/L glucose, 4 mM L-glutamine supplemented with 10% FBS and P/S (growth medium). Cells (500,000 cells/well) were seeded in 24-well plate in growth medium for 6 hours. Replace the growth medium with 1 mL lactate medium (10 mM lactate in base DMEM without sodium pyruvate) for overnight. Cells were treated with compounds in 1 mL lactate medium for 24 hours. The culture medium was collected and centrifuged at 12,000 rpm for 5 minutes at 4° C. to get rid of any cell debris. An aliquot of 0.5 mL of the supernatant was loaded to a deproteinizing column, centrifuged at 12,000 rpm for 15 minutes at 4° C. The flow-through was collected and stored at -80° C. for future analysis. The amount of lactate in the supernatant was analyzed by enzymatic L-Lactate Kit II (Eton Bioscience Inc.). Briefly, 50 μL of 10 times diluted sample was mixed with 50 μL reaction mixture. Lactic acid is oxidized by enzyme reactions to yield color product, which can be measured in dual modes, either at 570 nm for colorimetric assay or with Ex 530-560/Em 570-595 nm fluorescence assay. And the color or fluorescence intensity is proportional to lactic acid concentrations, therefore the sample lactic acid concentration can be accurately calculated based on the lactic acid standards. The signal was read on a Synergy H4 plate reader using 570 nM measurement wavelength, and the lactate consumption was calculated by medium lactate concentration at start point (10 mM) subtracted the end point.

Measuring Lactate Uptake by $^{14}$C-lactate Labeling Assay.

The inhibition of monocarboxylate transporters of the invention was determined using $^{14}$CLactate, and the data are shown in Table II. Cells are maintained in their appropriate growth medium (DMEM medium with 4.5 g/L glucose, 4 mM L-glutamine supplemented with 10% FBS and P/S (growth medium). Cell culture surface of 24-well cell culture plates (BD Bioscience) were aseptically coated with 80 µL poly-lysine (1 mg/mL, Sigma) for 5 mins, then rinsed with sterile cell culture grade water, air-dried for at least 2 hours before introducing cells and medium. SiHa cells were seeded in poly-lysine coated 24-well plate at 500,000 cells/ well in growth medium for 6 hours. Replace the growth medium with 1 mL lactate medium (10 mM lactate in base DMEM without sodium pyruvate) for overnight. Cells were rinsed with modified Kreb solution (containing 10 µM L-lactate, without glucose) and then treated with vehicle or increasing concentrations of compounds (0.1, 1, 10, 100 µM) at 37° C. in 1 mL modified Kreb solution (containing 10 µM L-lactate, 0.25% BSA) for one hour. Cells were labeled with 2 µM $^{14}$C-lacate in modified Kreb solution for 12 minutes, rinsed with ice-cold D-lactate containing Kreb solution (10 µM D-lactate, without glucose), and lysed with 0.1 M NaOH. An aliquot of sample was taken to measure protein concentration by Bradford reagent, and the rest of sample was incubated with liquid scintillation solution. After one hour agitation, the radioactivity was measured using Microbeta TriLux. CPM value was recorded and normalized to protein concentration.

We claim:

1. A compound having the formula:

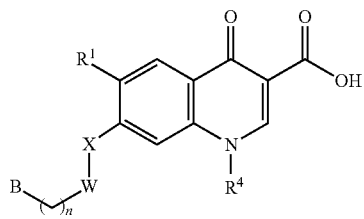

I or a pharmaceutically acceptable salt thereof, wherein:

1) n is 0; W is a bond; X is CH$_2$; and
   B is selected from:

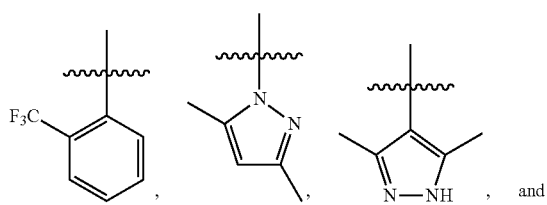

or 2) n is 1; W is a bond; X is —NCH$_3$; and
   B is selected from:

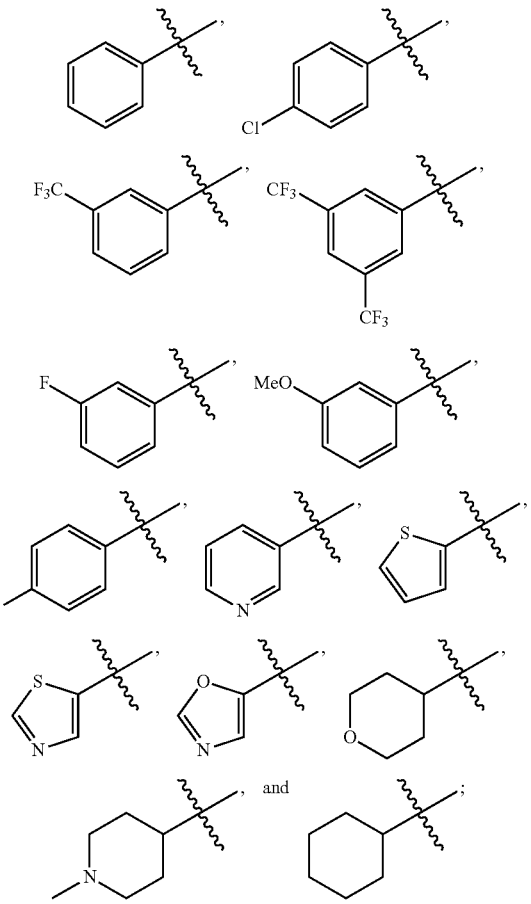

R$^1$ is selected from the group consisting of halogen, —CHF$_2$, —CF$_3$, —NO$_2$, —CN, —C(O)R", —C(O)OR", —SO$_2$R", —C(O)NR"$_2$, —C(O)N(OR")R" and

—C≡CH;

R$^4$ is selected from the group consisting of
(a) —C(O)R", —O(CH$_2$)$_{0-4}$R", —(CH$_2$)$_{0-4}$C(O)R", —(CH$_2$)$_{0-4}$C(O)OR", —NR"$_2$, —(CH$_2$)$_{0-4}$C(O)NR"$_2$, —(CH$_2$)$_{0-4}$S(O)R", —(CH$_2$)$_{0-4}$S(O)$_2$R", or —N(OR") R"; and (b) a group selected from
(1)

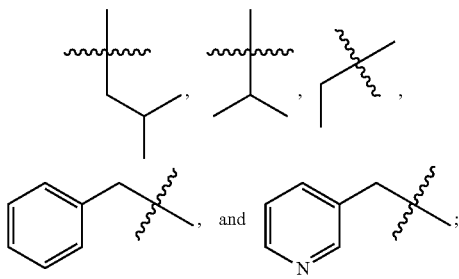

(2) a 3-8 membered saturated or partially unsaturated cycloalkyl ring,
(3) a 3-8 membered saturated or partially unsaturated heterocycloalkyl ring having 1-2 heteroatoms independently selected from nitrogen, oxygen, and sulfur,
(4) phenyl, and
(5) a 5-6 membered heteroaryl ring having 1-4 heteroatoms independently selected from nitrogen, oxygen, and sulfur; and R" is hydrogen or an optionally substituted group selected from:
(a) $C_{1-6}$ alkyl or $C_{3-6}$ cycloalkyl;
(b) a 3-8 membered saturated or partially unsaturated cycloalkyl ring formed from two R";
(c) a 3-8 membered saturated or partially unsaturated heterocycloalkyl ring formed from two R" having 1-2 heteroatoms independently selected from nitrogen, oxygen, and sulfur;
(d) phenyl; and
(e) a 5-6 membered heteroaryl ring having 1-4 heteroatoms independently selected from nitrogen, oxygen, and sulfur,
or
3) n is 0; W is C(O);

X is —$NR^5$— or —$CH_2$—, wherein $R^5$ is hydrogen or $C_1$-$C_3$ alkyl;
B is selected from the group consisting of phenyl; phenyl substituted with halogen, $C_1$-$C_3$ alkoxy, and trifluoromethyl; cyclohexyl; thiazolyl; oxazolyl; di($C_1$-$C_3$ alkyl)pyrazolyl; thiophenyl; tetrahydropyranyl; pyridinyl; and N-($C_1$-$C_3$ alkyl)piperidinyl;
$R^1$ is halogen, trifluoromethyl, cyano, or

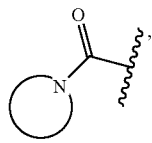 [SMILES: *C(N)=O]

wherein

represents azetidinyl, pyrrolidinyl, piperidinyl or azepinyl; and $R^4$ is selected from the group consisting of:

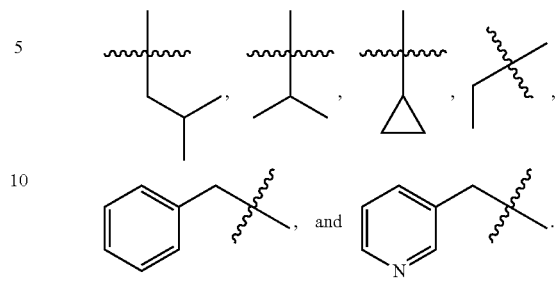

2. A compound according to claim 1, wherein $R^4$ is selected from:

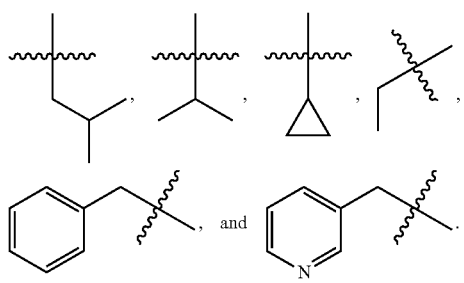

3. A compound according to claim 2, wherein $R^1$ is —F or

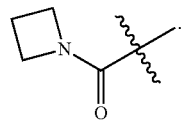 [SMILES: *C(=O)N1CCC1]

4. A compound according to claim 1, wherein n is 1; W is a bond; X is —$NCH_3$; B is selected from:

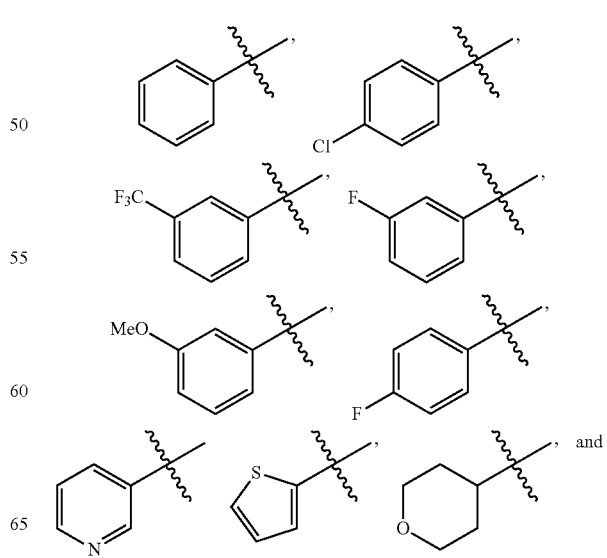

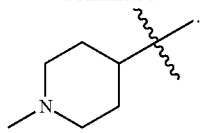

5. A compound according to claim 4, wherein, R⁴ is selected from:

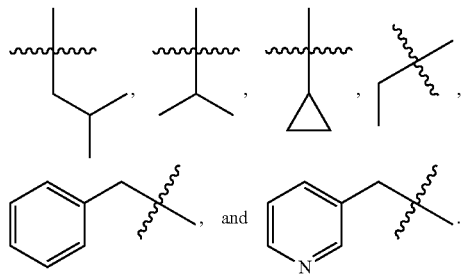

6. A compound according to claim 5, wherein R¹ is —F or

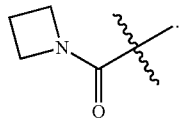

7. A compound according to claim 1, wherein the compound has the formula

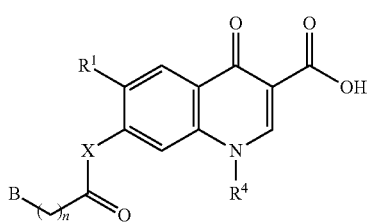

wherein:
X is —N(C₁-C₃ alkyl)— or —CH₂—;
R¹ is halogen, trifluoromethyl, cyano, or

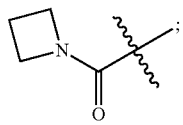 [SMILES: *C(=O)N1CCC1]

and
B is slected from:

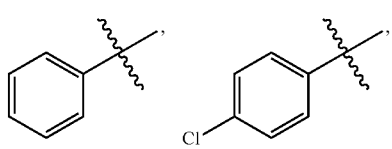

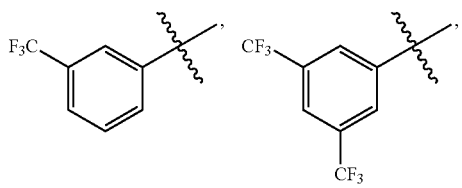

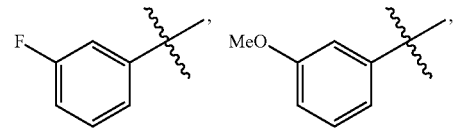

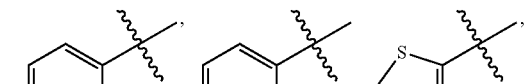

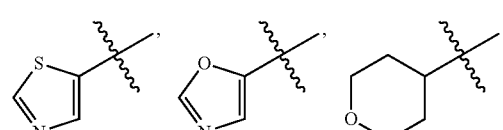

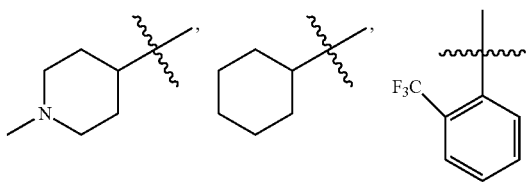

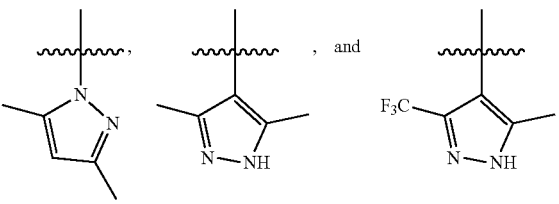

8. A compound according to claim 7 wherein the compound has the formula

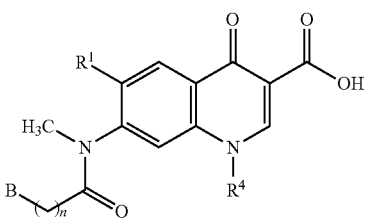

wherein
R¹ F; and
B is selected from:

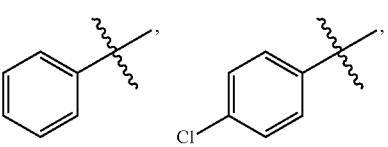

-continued
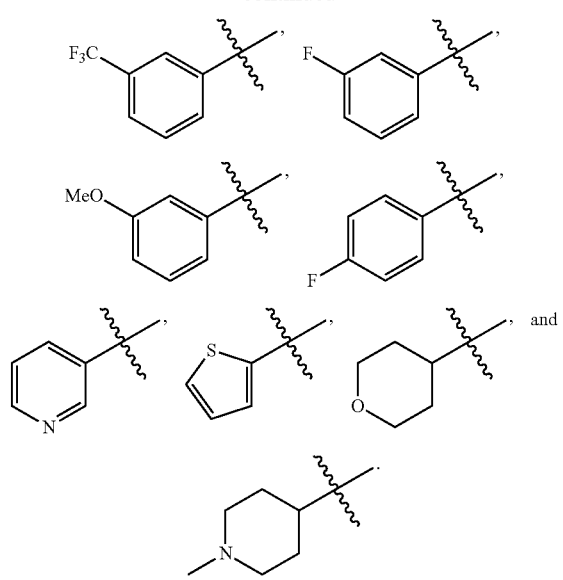
9. A compound according to claim 1, selected from the group consisting of:
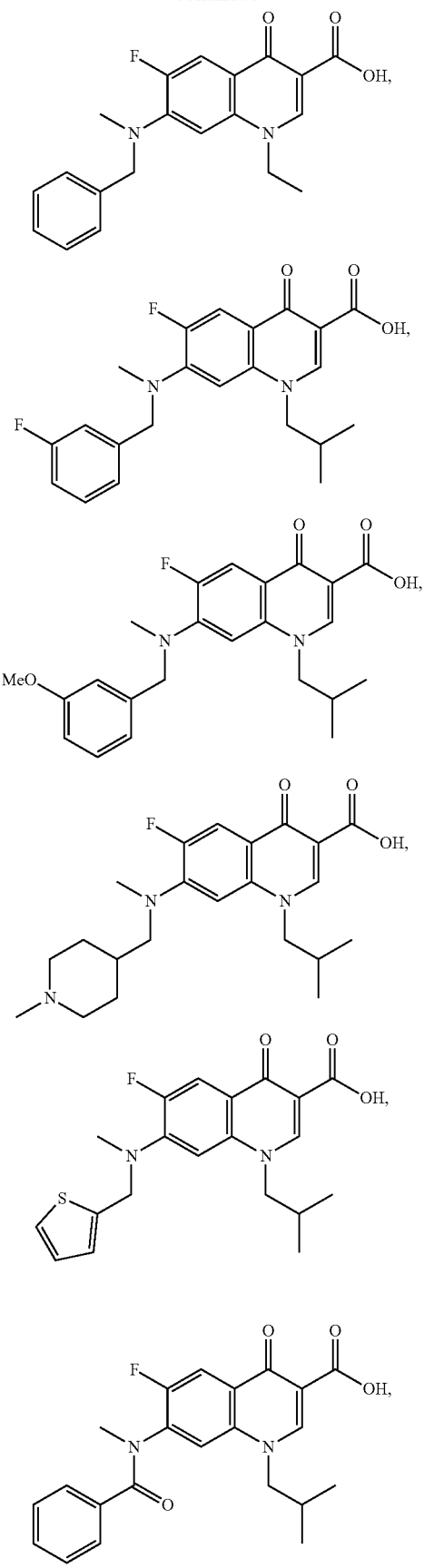

99
-continued
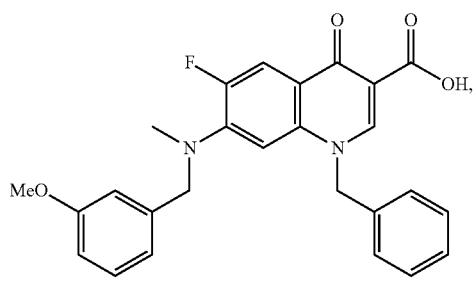
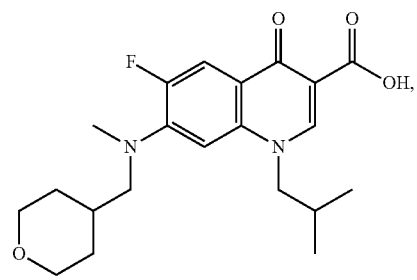
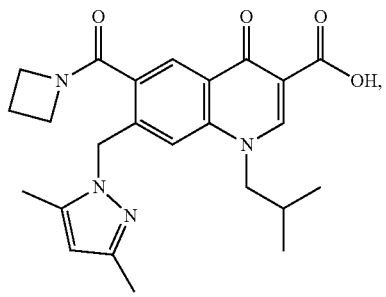
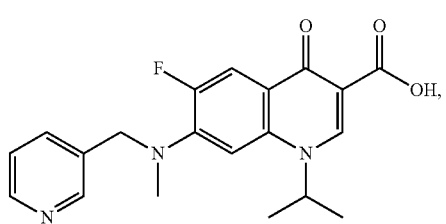
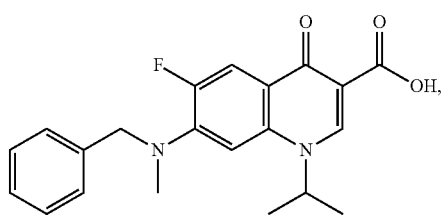
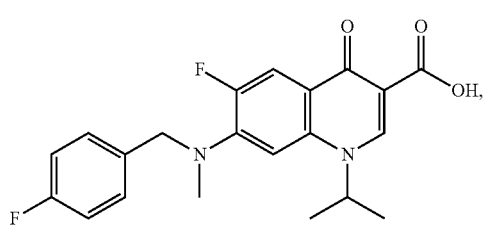
100
-continued
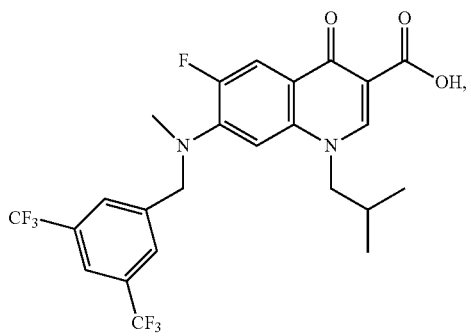
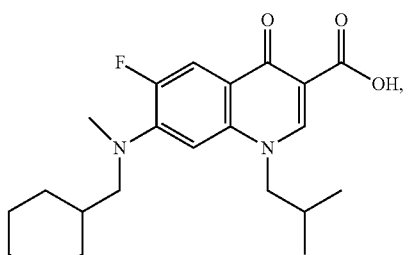
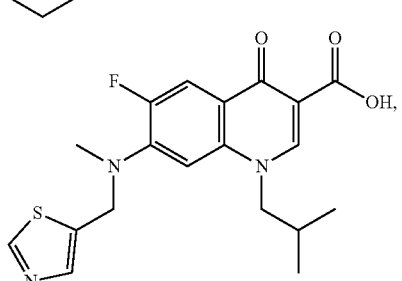
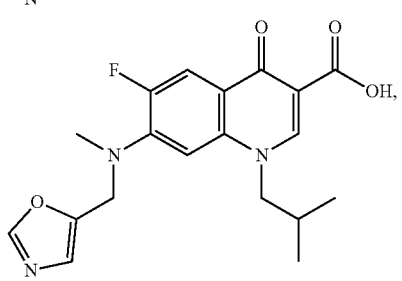
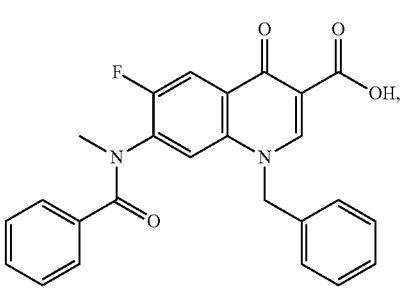
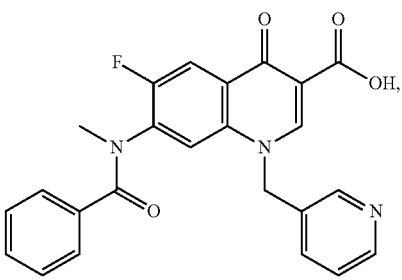

101
-continued
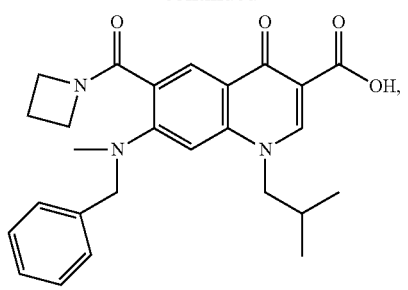
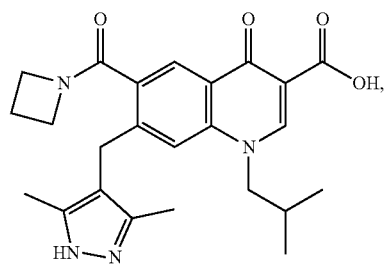
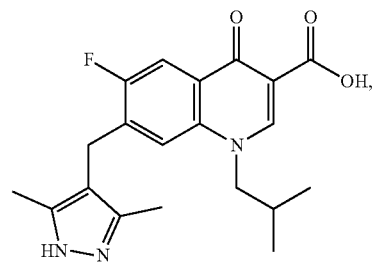
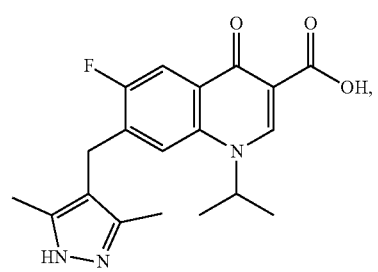
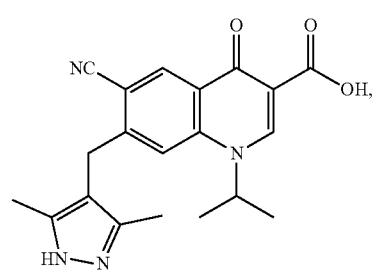
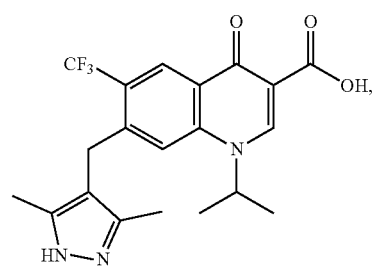
102
-continued
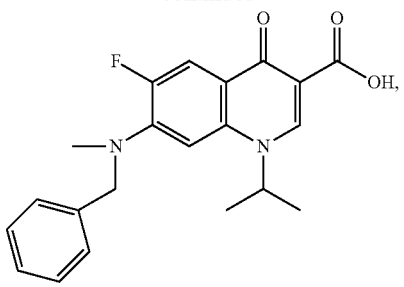
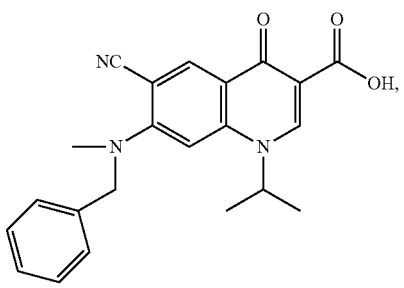
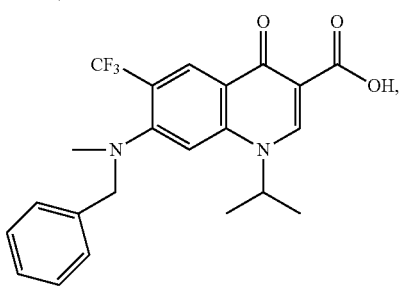
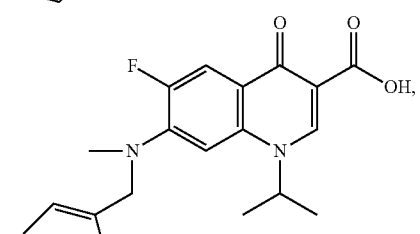
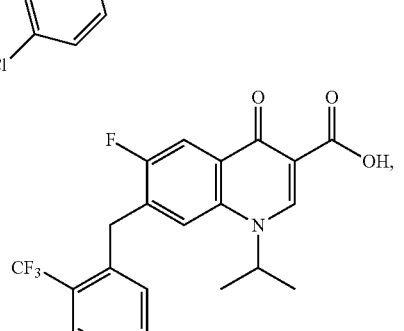
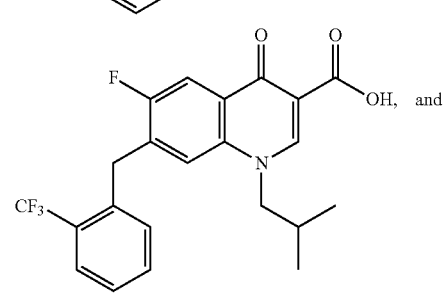

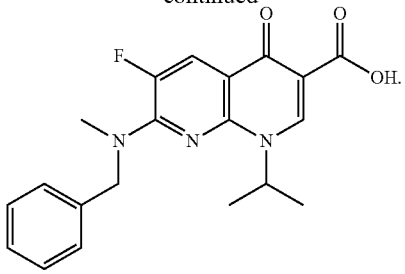

10. A method for inhibiting monocarboxylate transport comprising contacting a monocarboxylate transporter with an effective amount of a compound according to claim 1.

11. A method for treating a disorder associated with monocarboxylate transport comprising administering a therapeutically effective amount of a compound according to claim 1.

12. A method according to claim 11, wherein the disorder is chosen from cancer and other neoplastic disorders, inflammatory diseases, disorders of abnormal tissue growth, metabolic disorders, diabetes, obesity, malaria, and tissue and organ rejection.

* * * * *